(12) United States Patent
Lerchen et al.

(10) Patent No.: US 8,741,834 B2
(45) Date of Patent: Jun. 3, 2014

(54) DIPEPTOID PRODRUGS AND THE USE THEREOF

(75) Inventors: Hans-Georg Lerchen, Leverkusen (DE); Daniel Meibom, Leverkusen (DE); Alexandros Vakalopoulos, Hilden (DE); Barbara Albrecht-Küpper, Wülfrath (DE); Joerg Keldenich, Wuppertal (DE); Katja Zimmermann, Düsseldorf (DE); Peter Nell, Woodside, CA (US); Ursula Krenz, Leichlingen (DE)

(73) Assignee: Bayer Intellectual Property GmbH, Monheim (DE)

( * ) Notice: Subject to any disclaimer, the term of this patent is extended or adjusted under 35 U.S.C. 154(b) by 379 days.

(21) Appl. No.: 13/132,991

(22) PCT Filed: Dec. 3, 2009

(86) PCT No.: PCT/EP2009/008617
§ 371 (c)(1),
(2), (4) Date: Aug. 23, 2011

(87) PCT Pub. No.: WO2010/072314
PCT Pub. Date: Jul. 1, 2010

(65) Prior Publication Data
US 2011/0294719 A1 Dec. 1, 2011

(30) Foreign Application Priority Data
Dec. 16, 2008 (DE) .......................... 10 2008 062 567

(51) Int. Cl.
A61K 38/00 (2006.01)
A61K 47/00 (2006.01)
C07D 413/00 (2006.01)

(52) U.S. Cl.
USPC ........................................ 514/1.3; 546/271.4

(58) Field of Classification Search
CPC ............. A61K 31/4439; C07D 413/12; C07K 5/0202; C07K 5/0205
See application file for complete search history.

(56) References Cited

U.S. PATENT DOCUMENTS

| | | | |
|---|---|---|---|
| 4,052,510 A | 10/1977 | Simpson et al. |
| 5,670,525 A | 9/1997 | Urbahns et al. |
| 5,889,002 A | 3/1999 | Nielsen et al. |
| 6,191,280 B1 | 2/2001 | Hamprecht et al. |
| 6,586,441 B2 | 7/2003 | Borroni et al. |
| 6,632,823 B1 | 10/2003 | Vernier et al. |
| 6,693,102 B2 | 2/2004 | Stasch et al. |
| 6,706,717 B2 | 3/2004 | Barrish et al. |
| 6,743,798 B1 | 6/2004 | Straub et al. |
| 6,833,364 B1 | 12/2004 | Straub et al. |
| 6,864,287 B1 | 3/2005 | Alonso-Alija et al. |
| 7,045,631 B2 | 5/2006 | Rosentreter et al. |
| 7,078,417 B2 | 7/2006 | Rosentreter et al. |
| 7,109,218 B2 | 9/2006 | Rosentreter et al. |
| 7,129,255 B2 | 10/2006 | Rosentreter et al. |
| 7,135,486 B1 | 11/2006 | Rosentreter et al. |
| 7,173,036 B2 | 2/2007 | Sircar et al. |
| 7,173,037 B2 | 2/2007 | Alonso-Alija et al. |
| 7,186,716 B2 | 3/2007 | Wei et al. |
| 7,674,825 B2 | 3/2010 | Alonso-Alija et al. |
| 7,692,017 B2 | 4/2010 | Dinsmore et al. |
| 7,705,043 B2 | 4/2010 | Alonso-Alija et al. |
| 7,709,504 B2 | 5/2010 | Krahn et al. |
| 7,781,470 B2 | 8/2010 | Alonso-Alija et al. |
| 7,825,255 B2 | 11/2010 | Rosentreter et al. |
| 7,855,219 B2 | 12/2010 | Rosentreter et al. |
| 7,932,259 B2 | 4/2011 | Nakazato et al. |
| 7,951,811 B2 | 5/2011 | Nakazato et al. |
| 8,242,281 B2 | 8/2012 | Rosentreter et al. |
| 8,304,412 B2 | 11/2012 | Nell et al. |
| 8,420,825 B2 | 4/2013 | Vakalopoulos et al. |
| 8,426,602 B2 | 4/2013 | Meibom et al. |
| 8,440,700 B2 | 5/2013 | Nell et al. |
| 2003/0232860 A1 | 12/2003 | Harada et al. |
| 2004/0162427 A1 | 8/2004 | Rosentreter et al. |
| 2004/0176446 A1 | 9/2004 | Alonso-Alija et al. |
| 2005/0182105 A1 | 8/2005 | Nirschi et al. |
| 2005/0227972 A1 | 10/2005 | Rosentreter et al. |
| 2005/0250774 A1 | 11/2005 | Ono et al. |
| 2006/0264432 A1 | 11/2006 | Rosentreter et al. |

(Continued)

FOREIGN PATENT DOCUMENTS

CA 2698170 2/2009
EP 0 608 565 A1 12/1993

(Continued)

OTHER PUBLICATIONS

Yu, et al.:"Physical Characterization of Polymorphic Drugs: An Integrated Characterization Strategy," Pharmaceutical Science & Technology Today, Jun. 1998, 1(3):118-127.
Zhu, G. et al., "Design and synthesis of pyridine-pyrazolopyridine-based inhibitors of protein kinase B/Akt," Bioorg. Med. Chem. 2007, 15 (6), 2441-2452.
Elzein, et al.:"A1 Adenosine Receptor Agonists and their Potential Theraputic Applications," Expert Opin. Investig. Drugs, 2008, 17(12):1901-1910.
Inotek Pharmaceuticals Press Release, "Inotek Pharmaceuticals Presents Preclinical Data in Support of Novel Glaucoma Candidate, INO-8875 at ARVO. INO-8875 currently in Phase 1/2 clinical trial, results anticipated mid-2009," May 6, 2009.
Martyn, et al.:"Obesity-induced Insulin Resistance and Hypoglycemia: Etiologic Factors and Molecular Mechanisms," Anesthesiology, 2008, 109:137-148.

(Continued)

*Primary Examiner* — Marcela M Cordero Garcia
(74) *Attorney, Agent, or Firm* — Karen B. King; Thomas C. Blankinship

(57) ABSTRACT

The present application relates to dipeptide-like prodrug derivatives of 2-amino-6-({[2-(4-chlorophenyl)-1,3-oxazol-4-yl]methyl}sulfanyl)-4-(4-{[2,3-dihydroxypropyl]oxy}phenyl)pyridine-3,5-dicarbonitrile, processes for their preparation, their use for the treatment and/or prophylaxis of diseases, and their use for the manufacture of medicaments for the treatment and/or prophylaxis of diseases, especially of cardiovascular disorders.

8 Claims, No Drawings

(56) References Cited

U.S. PATENT DOCUMENTS

| | | |
|---|---|---|
| 2007/0066630 A1 | 3/2007 | Palani et al. |
| 2007/0293670 A1 | 12/2007 | Nakazato et al. |
| 2008/0167321 A1 | 7/2008 | Kamboj et al. |
| 2008/0269300 A1 | 10/2008 | Erguden et al. |
| 2009/0221649 A1 | 9/2009 | Krahn et al. |
| 2010/0009973 A1 | 1/2010 | Rhodes et al. |
| 2010/0048641 A1 | 2/2010 | Nell et al. |
| 2010/0069363 A1 | 3/2010 | Nell et al. |
| 2010/0093728 A1 | 4/2010 | Nell et al. |
| 2010/0279970 A1 | 11/2010 | Barman et al. |
| 2011/0136871 A1 | 6/2011 | Hübsch et al. |
| 2011/0237629 A1 | 9/2011 | Meibom et al. |
| 2011/0294718 A1* | 12/2011 | Lerchen et al. .......... 514/1.3 |
| 2013/0267700 A1* | 10/2013 | Vakalopoulos et al. ...... 540/597 |

FOREIGN PATENT DOCUMENTS

| | | |
|---|---|---|
| JP | 09-132529 | 5/1997 |
| JP | 10-324687 | 12/1998 |
| JP | 2003-183254 | 7/2003 |
| WO | 95/34563 | 12/1995 |
| WO | 97/27177 A2 | 7/1997 |
| WO | 99/03861 A1 | 1/1999 |
| WO | 02/48115 A2 | 6/2002 |
| WO | 02/50071 A1 | 6/2002 |
| WO | 03/091246 | 11/2003 |
| WO | 2004/014372 A1 | 2/2004 |
| WO | 2004/054505 A2 | 7/2004 |
| WO | 2005/007647 | 1/2005 |
| WO | 2007/073855 | 7/2007 |
| WO | 2008/008059 | 1/2008 |

OTHER PUBLICATIONS

Arndt, et al, "Diazo-methan and o-Nitroveerbindungen, II: N-Oxyistatin aus o-Ntro-benzolychorid.",Eistert et al., Ber. Dtsch. Chem. Ges., 60, 1364-1370 (1927).

Ellenbogen et al, "Trial to evaluate the management of paroxysmal superventricular tachycardia during an electrophysiology study with tecadenoson," Circulation, 2005, 111:3202-3208.

U.S. Appl. No. 11/661,820, filed Mar. 10, 2008 published as US 2008-0269300.

U.S. Appl. No. 12/516,939, filed Nov. 24, 2009 published as US 2010-0069363.

U.S. Appl. No. 12/440,423, filed Dec. 23, 2009 published as US 2010-0093728.

U.S. Appl. No. 12/671,694, filed Jul. 27, 2011, published as US 2011-0294718.

U.S. Appl. No. 12/995,028, filed Feb. 16, 2011 published as US 2011-0207698.

U.S. Appl. No. 12/697,000, filed Jan. 29, 2010, published as US 2010-0197609—now 8,420,825.

U.S. Appl. No. 13/805,653, filed Dec. 19, 2012.

Anand, et al.:"Novel Dipeptide Prodrugs of Acyclovir for Ocular Herpes Infections: Bioreversion, Antiviral Activity and Transport Across Rabbit Cornea," Current Eye Research, Mar. 2003, 26 (3-4):151-163.

Avila, et al.: A1-, A2A- and A3-subtype adenosine receptors modulate intraocular pressure in the mouse, British Journal of Pharmacology, 2001, 134:241-245.

Barnaby, et al.:"Structure-Activity Relationship Study of Prion Inhibition by 2-Aminopyridine-3,5-dicarbonitrile-Based Compounds: Parallel Synthesis, Bioactivity, and in Vitro Pharmacokinetics," J. Med. Chem., 2007, 50:65-73.

Barton et al.,:"Homologation of Acids via Carbon Radicals Generated from the Acyl Derivatives of N-Hydroxy-2-Thiopyrodine. (The Two-Carbon Problem)," Tetrahedron Letters, 1991, 32(28): 3309-3312.

Bauman:"Updating the Evidence that Physical Activity is Good for Health: An Epidemiological Review 2000-2003," J. Sci. Med. Sport, Apr. 2004, 7(1): Suppl:6-19.

Beaumont, et al.:"Design of Ester Prodrugs to Enhance Oral Absorption of Poorly Permeable Compounds: Challenges to the Discovery Scientist," Current Drug Metabolism, 2003, 4(6):461-485.

Beukers, et al.:"New, Non-Adenosine, High-Potency Agonists for the Human Adenosine A2B Receptor with an Improved Selectivity Profile Compared to the Reference Agonist N-Ethylcarboxamidoadenosine," Journal of Medicinal Chemistry, Jul. 15, 2004, 47(15): 3707-3709.

Bundgaard:"Design of Prodrugs: Bioreversible Derivatives for Various Functional Groups and Chemical Entities," Elsevier Science Publishers B.V., 1985, pp. 1092.

Castedo, et al.:"Synthesis and Pharmacological Activity of Some Nitrofuraldehyde Cyanopyridine Derivatives," Eur. J. Med. Chem., 1984, 19(6):555-557, abstract retrieved from CAPLUS Accession No. 1985:437337, EPO Document XP002202946.

Cesar, et al.:"Trimethylsilyldiazomethane in the Preparation of Diazoketonesvia Mixed Anhydride and Coupling Reagent Methods:A New Approach to the Arndt-Eistert Synthesis," Tetrahedron Letters, 2001, 42: 7099-7102.

Crosson: "Intraoccular Pressure Responses to the Adenosine Agonist Cyclohexyladenosine: Evidence for a Dual Mechanism of Action," IOVS, Jul. 2001, 42(8): 1837-1840.

Dhalla, et al.:"Pharmacology and Theraputic Applications of A1 Adenosine Receptor Ligands," Current Topics in Medicinal Chemisty, 2003, 3:369-385.

Dyachenko, et al.:"Single Stage Synthesis of 2-Alkylthio(seleno)-4-Hetaryl-3-cyano-5,6,7,8-Tetrahydroquinolines," Chemistry of Heterocyclic Compounds, 1997, 33(10): 1203-1208.

Dyachenko, et al.:"New Route to 6-Amino-4-aryl-3,5-dicyano-pyridine-2(1H)-thiones," Russian Journal of Organic Chemistry,1997, 33(7):1014-1017.

Dyachenko, et al.:"Michael Reaction in SyntheSis of 6-Amino-4-(4-Butoxyphenyl)-3,5-Dicyanopyridine-2(1H)-thionene," Chemistry of Heterocyclic Compounds, 1998, 34(2):188-194.

Dyachenko:"Cyclohexanecarbaldehyde in Multicomponent Syntheses of Functionalized Cyclohexyl-Substituted Acrylonitriles, 4H-Chalcogenopyrans, 1,4-Dihydropyridines, and Pyridines," Russian Journal of General Chemistry, 2006, 76(2):282-291.

Dyachenko, et al.,:"Synthesis and Recyclization of 4-Aryl-2,6-diamino-3,5-dicyano-4H-thiopyrans," Russian Journal of Organic Chemistry, 1998, 34(4): 557-563.

Eissa, et al.:"Synthesis and Biological Evaluation of Pyrido[2,3-d]pyrimidine as Antitumor Effect," Egypt. J. Chem., 2006, 49(6):761-774.

Elnagdi, et al.:"Studies with Polyfunctionally Substituted Heterocycles: Synthesis of New Pyridines, Naphtho[1,2-b] pyrans, Pyrazolo[3,4]pyridines and Pyrazolo[1,5-a]pyrimidines," Z. Naturforsch, 1992, 47b:572-578.

El-Torgoman, et al.:"Nitriles in Heterocyclic Synthesis: The reaction of 2-Thiocarbamoyl Cinnamonitriles with Active Methylene Reagents," Z. Naturforsch., 1987, 42b:107-111.

Ettmayer, et al.:"Lessons Learned from Marketed and Investigational Prodrugs," J. Med. Chem., May 6, 2004, 47(10) 2393-2404.

Fuentes, et al.:"Heterocycle Synthesis. XVI. Reaction of Malononitrile with Benzylidenemalononitriles in Presence of Amines." An. Quim., Ser. C., 1980, 76(1): 68-69, English language abstract retrieved from CAPLUS Accession No. 1981:139574, EPO Document No. XP002202947.

Goto, et al.:"Studies on Azole Compounds.III.1 Reactions of Oxazole N-Oxides with Phosphoryl Chloride and Acetic Anhydride 2", Chem. Pharm. Bull. 1971, 19: 2050-2057.

Ibrahim, et al.:"Synthesis and Biological Activity of Some New Heterocyclic Quinoline Derivatives," Phosphorus, Sulfer, and Silicon, 1991, 57: 293-301.

Jacobson, et al,:"Adenosine Receptors as Theraputic Targets," Nat. Rev. Drug Discover.,2005, 5:247-264.

Jacobson, et al.:"Adenosine Receptor Ligands: Differences with Acute Versus Chronic Treatment," Trends in Pharmacological Sciences, Mar. 1996, 17(3):108-113.

Kambe, et al.:"Synthetic Studies Using a,β-Unsaturated Nitriles: Facile Synthesis of Pyridine Derivatives," Synthesis Communications, Jul. 1981, pp: 531-533.

(56) References Cited

OTHER PUBLICATIONS

Klotz, et al.:"Comparative Pharmacology of Human Adenosine Receptor Subtypescharacterization of Stably Transfected Receptors in CHO Cells," Naunyn-Schmiedeberg's Arch Pharmacol, 1998, 357:1-9.
Klotz:"Adenosine Receptors and their Ligands," Naunyn-Schmiedeberg's Arch. Pharmacol., 2000, 362: 382-391.
Müller, et al.:"Adenosine Receptor Antagonists: Structures and Potential Therapeutic Applications," Current Pharmaceutical Design, 1996, 2:501-530.
Müller:"Adenosine Receptor Ligands-Recent Developments Part I. Agonists," Current Medicinal Chemistry, 2000, 7:1269-1288.
Müller:"Review. Cardiovascular & Renal. A1-Adenosine Receptor Antagonists," Exp. Opin. Ther. Patents, 1997, 7 (5):419-440.
Inotek Pharmaceuticals Press Release, "Inotek Pharmaceuticals Initiates Multiple-Dose Phase 2 Clinical Trial of INO-8875 in Patients with Glaucoma," Jun. 17, 2010.
Olah, et al.,"Cloning, Expression, and Characterization of the Unique Bovine A1 Adenosine Receptor," Journal of Biological Chemistry, May 25, 1992, 267(15):10764-10770.
Patani, et al.: "Bioisosterism: A Rational Approach in Drug Design," Chem. Rev., 1996, 96:3147-3176.
Pflueger, et al.:"Role of Adenosine in Contrast Media-Induced Acute Renal Failure in Diabetes Mellitus," Mayo Clin Proc., Dec. 2000, 75(12):1275-1283.
Poulsen, et al.:"Adenosine Receptors: New Opportunities for Future Drugs," Bioorganic & Medicinal Chemistry, Jan. 8, 1998, 6(6): 619-641.
Quintela, et al.:"Reactivity of Heterocyclic Compounds. V. Behavior of 6-alkoxy-2-amino-(or chloro)-4-aryl-3,5-dicyanopyridines in the Presence of Nucleophiles," Anales de Quimica, Serie C: Quimica Organica y Bioquimica, 1984, 80(3):268-72, English language abstract retrieved from CAPLUS Accession No. 1985:437345, CAPLUS Document No. 103:37345, EPO Document No. XP002202945.
Quintela, et al.:"Synthesis, Antihistaminic and Cytotoxic Activity of Pyridothieno- and Pyridodithienotriazines", Eur. J. Med. Chem, 1998, 33:887-897.
Rodinovskaya, et al.:"Substituted 4-(3-Cyanopyridin-2-ylthio)acetoacetates: New Convenient Reagents for the Synthesis of Heterocycles," Synthesis, 2006, (14): 2357-2370.
Rosenman:"Do Environmental Effects on Human Emotions Cause Cardiovascular Disorders?," Acta Physiologica Scandinavica, Supplement,1997, 161/640 (133-136), abstract retrieved from EMBASE Accession No. 97358868.
Ruhe, et al.:"Use of Antioxidant Nutrients in the Prevention and Treatment of Type 2 Diabetes," Journal of the American College of Nutrition, 2001, 20(5): 363S-369S.
Shams, et al.:"Nitriles in Organic Synthesis. New Routes for Synthesis of Pyridines and Azinothiopyrans," Journal fuer Praktische Chemie (Leipzig), 1988, 330(5):817-13, abstract retrieved from CAPLUS Accession No. 1989:497050.
Sheridan:"The Most Common Chemical Replacements in Drug-Like Compounds," J Chem. Inf. Comput. Sci., 2002, 42:103-108.
Suttner, et al.:"The Heart in the Elderly Critically Ill Patient," Curr. Opin. Crit. Care, Oct. 2002, 8(5):389-94, abstract retrieved from MEDLINE Accession No. 2002495386, PubMed ID: 12357105.
Szydlowski, et al.:"Biological Role of Chromium," Diabetologia Polska, 2003, 10(3):365-370, English language abstract retrieved from EMBASE Accession No. 2004016455.
Vasudevan A. et al., "Aminopiperidine indazoles as orally efficacious melanin concentrating hormone receptoer-1 antagonists," Bioorg. Med. Chem. Lett. 2005, 15 (23), 5293-5297.
Vippagunta, et al.:"Dystalline Solids," Advanced Drug Delivery Reviews, May 16, 2001, 48(1):3-26.
West:"Solid State Chemistry and its Applications," Wiley, New York, 1988, pp. 358 & 365.
Ye, et al.:Organic Synthesis with α-Diazocarbonyl Compounds, Chem. Rev. 1994, 94:1091-1160.

\* cited by examiner

DIPEPTOID PRODRUGS AND THE USE THEREOF

The present application relates to dipeptide-like prodrug derivatives of 2-amino-6-({[2-(4-chlorophenyl)-1,3-oxazol-4-yl]methyl}sulfanyl)-4-(4-{[2,3-dihydroxypropyl]oxy}phenyl)-pyridine-3,5-dicarbonitrile, processes for their preparation, their use for the treatment and/or prophylaxis of diseases, and their use for the manufacture of medicaments for the treatment and/or prophylaxis of diseases, especially of cardiovascular disorders. Prodrugs are derivatives of an active ingredient which undergo in vivo an enzymatic and/or chemical biotransformation in one or more stages before the actual active ingredient is liberated. A prodrug residue is ordinarily used in order to improve the profile of properties of the underlying active ingredient [P. Ettmayer et al., *J. Med. Chem.* 47, 2393-2404 (2004)]. In order to achieve an optimal profile of effects, it is necessary, in this connection, for the design of the prodrug residue, as well as the desired mechanism of liberation, to conform very accurately with the individual active ingredient, the indication, the site of action, and the administration route. A large number of medicaments are administered as prodrugs which exhibit an improved bioavailability by comparison with the underlying active ingredient, for example achieved by improving the physicochemical profile, specifically the solubility, the active or passive absorption properties or the tissue-specific distribution. An example which may be mentioned from the wide-ranging literature on prodrugs is: H. Bundgaard (Ed.), *Design of Prodrugs: Bioreversible derivatives for various functional groups and chemical entities*, Elsevier Science Publishers B.V., 1985.

Adenosine, a purine nucleoside, is present in all cells and is released under a large number of physiological and pathophysiological stimuli. Adenosine is produced inside cells on degradation of adenosine 5'-monophosphate (AMP) and S-adenosylhomocysteine as intermediate, but can be released from the cell and then exerts, by binding to specific receptors, effects as hormone-light substance or neurotransmitter. To date, the receptor subtypes A1, A2a, A2b and A3 are known [cf. K. A. Jacobson and Z.-G. Gao, *Nat. Rev. Drug Discover.* 5, 247-264 (2006)]. The activation of A1 receptors by specific A1 agonists leads in humans to a frequency-dependent lowering of the heart rate, without having an effect on the blood pressure. Selective A1 agonists could therefore be suitable, among other things, for the treatment of angina pectoris and atrial fibrillation.

The activation of A2b receptors by adenosine or specific A2b agonists leads to a lowering of blood pressure via the expansion of vessels. The lowering of blood pressure is accompanied by a reflectory increase in heart rate. The increase in heart rate can be reduced by the activation of A1 receptors by specific A1 agonists.

The combined effect of selective A1/A2b agonists on the vascular system and the heart rate therefore results in a systemic lowering of blood pressure without a relevant increase in heart rate. With a pharmacological profile of this kind, dual A1/A2b agonists could be used to treat, for example, hypertension in humans.

The compound 2-amino-6-({[2-(4-chlorophenyl)-1,3-oxazol-4-yl]methyl}sulfanyl)-4-(4-{[2,3-dihydroxypropyl]oxy}phenyl)pyridine-3,5-dicarbonitrile of the formula (A)

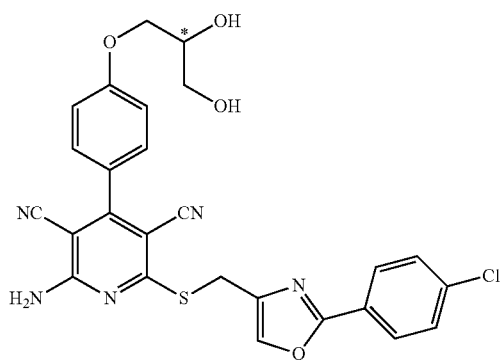

is a potent and selective adenosine A1 receptor agonist with a certain dual, A2b-agonist component to its action (see PCT application WO 2009/015776-A1). The substance is presently undergoing in-depth investigation as a possible new active pharmaceutical ingredient for the prevention and therapy of, in particular, cardiovascular disorders. Of particular significance in this context is the enantiomerically pure form of the compound (A), which on the C* carbon atom of the propane-1,2-diol group possesses an R-configuration.

However, the compound (A) has only a limited solubility in water, physiological media and organic solvents, and an only low bioavailability after oral administration of a suspension of crystalline material. On the one hand, this allows intravenous administration of the active ingredient only in very low dosages; infusion solutions based on physiological saline solutions can be produced only with difficulty with conventional solubilizers. On the other hand formulation in tablet form is difficult.

It was therefore an object of the present invention to identify derivatives or prodrugs of compound (A) which have an improved solubility in the media mentioned and/or an improved bioavailability after oral administration and, at the same time, make it possible to have controlled liberation of the active ingredient (A) in the patient's body after administration. In addition, further areas of therapeutic use of this active ingredient could be opened up by an improved possibility of intravenous administration.

A review of prodrug derivatives based on carboxylic esters and possible properties of such compounds is given for example in K. Beaumont et al., *Curr. Drug Metab.* 4, 461-485 (2003).

The present invention relates to compounds of the general formula (I)

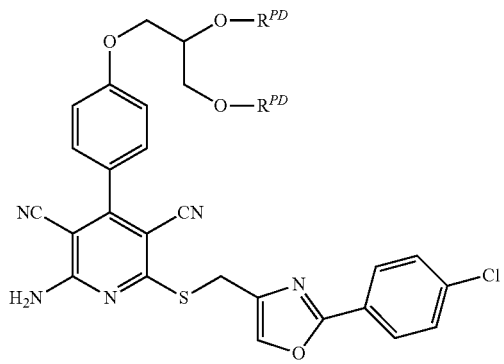

in which
R^PD is a group of the formula

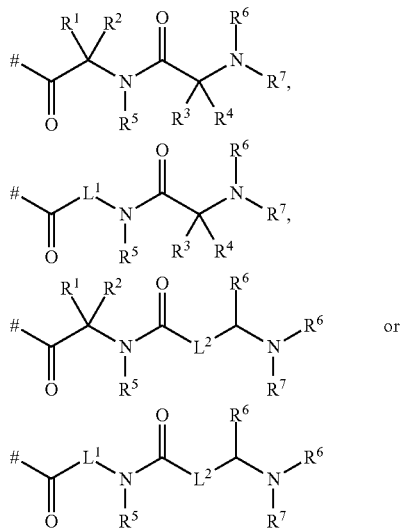

in which
# means the point of linkage to the respective O atom,
L¹ is straight-chain (C₂-C₄)-alkanediyl,
L² is straight-chain (C₁-C₃)-alkanediyl,
R¹ and R³ are identical or different and are independently of one another hydrogen or the side group of a natural α-amino acid or its homologs or isomers,
R² and R⁴ are independently of one another hydrogen or methyl
or
R¹ and R² or R³ and R⁴ are in each case linked to one another and, together with the carbon atom to which they are jointly attached, form a 3- to 6-membered saturated carbocycle,
R⁵ is hydrogen or (C₁-C₄)-alkyl
or
R⁵ is linked to R¹ and both, together with the atoms to which they are attached, form a pyrrolidine or piperidine ring,
R⁶ and R⁷ are identical or different and independently of one another are hydrogen or (C₁-C₄)-alkyl which may be substituted by hydroxyl, (C₁-C₄)-alkoxy, amino, mono-(C₁-C₄)-alkylamino or di-(C₁-C₄)-alkylamino
or
R⁶ and R⁷ are linked to one another and, together with the nitrogen atom to which they are attached, form a 5- or 6-membered saturated heterocycle which may comprise a further ring heteroatom from the series consisting of N and O, and may be substituted one or two times, identically or differently, by (C₁-C₄)-alkyl, amino, hydroxyl and/or (C₁-C₄)-alkoxy,
or
R⁶ is linked to R³ and both, together with the atoms to which they are attached, form a pyrrolidine or piperidine ring
and
R⁶ is hydrogen or carboxyl,
and the salts, solvates and solvates of the salts thereof.

Compounds according to the invention are the compounds of the formula (I) and the salts, solvates and solvates of the salts thereof, the compounds which are encompassed by formula (I) and are of the formulae mentioned hereinafter, and the salts, solvates and solvates of the salts thereof, and the compounds which are encompassed by formula (I) and are mentioned hereinafter as exemplary embodiments, and the salts, solvates and solvates of the salts thereof, insofar as the compounds encompassed by formula (I) and mentioned hereinafter are not already salts, solvates and solvates of the salts.

The compounds according to the invention may, depending on their structure, exist in stereoisomeric forms (enantiomers, diastereomers). The invention therefore relates to the enantiomers or diastereomers and respective mixtures thereof. The stereoisomerically pure constituents can be isolated in a known manner from such mixtures of enantiomers and/or diastereomers.

Where the compounds according to the invention can occur in tautomeric forms, the present invention encompasses all tautomeric forms.

Salts preferred for the purposes of the present invention are physiologically acceptable salts of the compounds according to the invention. However, salts which are themselves unsuitable for pharmaceutical applications but can be used for example for isolating or purifying the compounds according to the invention are also encompassed.

Besides monosalts, the present invention also includes where appropriate possible polysalts such as di- or trisalts.

Physiologically acceptable salts of the compounds according to the invention include acid addition salts of mineral acids, carboxylic acids and sulphonic acids, e.g. salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of usual bases such as, by way of example and preferably, alkali metal salts (e.g. sodium and potassium salts), alkaline earth metal salts (e.g. calcium and magnesium salts) and ammonium salts, derived from ammonia or organic amines having 1 to 16 C atoms, such as, by way of example and preferably, ethylamine, diethylamine, triethylamine, ethyldiisopropylamine, monoethanolamine, diethanolamine, triethanolamine, choline, dicyclohexylamine, dimethylaminoethanol, procain, dibenzylamine, morpholine, N-methylmorpholine, arginine, lysine, ethylenediamine, piperidine and N-methylpiperidine.

Solvates refer for the purposes of the invention to those forms of the compounds according to the invention which form a complex in the solid or liquid state through coordination with solvent molecules. Hydrates are a specific form of solvates in which the coordination takes place with water. Solvates preferred in the context of the present invention are hydrates. In the context of the present invention, the substituents have the following meaning unless otherwise specified:

(C₁-C₄)-Alkyl is in the context of the invention a straight-chain or branched alkyl radical having 1 to 4 carbon atoms. Examples which may be preferably mentioned are: methyl, ethyl, n-propyl, isopropyl, n-butyl, isobutyl, sec-butyl, tert-butyl.

(C₂-C₄)-Alkanediyl, is in the context of the invention a straight-chain, α,ω-divalent alkyl radical having 2 to 4 carbon atoms. Examples which may be preferably mentioned are: ethane-1,2-diyl (1,2-ethylene), propane-1,3-diyl (1,3-propylene), butane-1,4-diyl (1,4-butylene).

(C₁-C₃)-Alkanediyl is in the context of the invention a straight-chain, α,ω-divalent alkyl radical having 1 to 3 carbon atoms. Examples which may be preferably mentioned are: methanediyl(methylene), ethane-1,2-diyl (1,2-ethylene), propane-1,3-diyl (1,3-propylene).

(C₁-C₄)-Alkoxy is in the context of the invention a straight-chain or branched alkoxy radical having 1 to 4 carbon atoms.

Examples which may be preferably mentioned are: methoxy, ethoxy, n-propoxy, isopropoxy, n-butoxy, tert-butoxy.

Mono-$(C_1$-$C_4)$-alkylamino is in the context of the invention an amino group having a straight-chain or branched alkyl substituent which has 1 to 4 carbon atoms. Examples which may be preferably mentioned are: methylamino, ethylamino, n-propylamino, isopropylamino, n-butylamino, tert-butylamino.

Di-$(C_1$-$C_4)$-alkylamino is in the context of the invention an amino group having two, identical or different, straight-chain or branched alkyl substituents which each have 1 to 4 carbon atoms. Examples which may be preferably mentioned are: N,N-dimethylamino, N,N-diethylamino, N-ethyl-N-methylamino, N-methyl-N-n-propylamino, N-isopropyl-N-n-propylamino, N,N-diisopropylamino, N-n-butyl-N-methylamino, N-tert-butyl-N-methylamino.

A 3- to 6-membered carbocycle is in the context of the invention a monocyclic, saturated cycloalkyl group having 3 to 6 ring carbon atoms. Examples which may be preferably mentioned are: cyclopropyl, cyclobutyl, cyclopentyl, cyclohexyl.

A 5- or 6-membered heterocycle is in the context of the invention a monocyclic, saturated heterocycloalkyl group having a total of 5 or 6 ring atoms which contains one ring nitrogen atom and optionally a second ring heteroatom from the series consisting of N and O. Examples which may be preferably mentioned are: pyrrolidinyl, piperidinyl, piperazinyl, morpholinyl.

The side group of an α-amino acid in the meaning of $R^1$ and $R^3$ encompasses both the side groups of naturally occurring α-amino acids and the side groups of homologs and isomers of these α-amino acids. The α-amino acid may in this connection have both the L and the D configuration or else be a mixture of the L form and D form. Examples of side groups which may be mentioned are: methyl (alanine), propan-2-yl (valine), propan-1-yl (norvaline), 2-methylpropan-1-yl (leucine), 1-methylpropan-1-yl (isoleucine), butan-1-yl (norleucine), tert-butyl(2-tert-butylglycine), phenyl (2-phenylglycine), benzyl (phenylalanine), p-hydroxybenzyl (tyrosine), indol-3-ylmethyl (tryptophan), imidazol-4-ylmethyl (histidine), hydroxymethyl (serine), 2-hydroxyethyl (homoserine), 1-hydroxyethyl (threonine), mercaptomethyl (cysteine), methylthiomethyl (S-methylcysteine), 2-mercaptoethyl (homocysteine), 2-methylthioethyl (methionine), carbamoylmethyl (asparagine), 2-carbamoylethyl (glutamine), carboxymethyl (aspartic acid), 2-carboxyethyl (glutamic acid), 4-aminobutan-1-yl (lysine), 4-amino-3-hydroxybutan-1-yl(hydroxylysine), 3-aminopropan-1-yl(ornithine), 3-guanidinopropan-1-yl (arginine), 3-ureidopropan-1-yl (citrulline).

Preferred α-amino acid side groups in the meaning of $R^1$ are methyl (alanine), propan-2-yl (valine), 1-methylpropan-1-yl (isoleucine), 2-methylpropan-1-yl (leucine), benzyl (phenylalanine), p-hydroxybenzyl (tyrosine), hydroxymethyl (serine), 1-hydroxyethyl (threonine). The L configuration is preferred in each case.

Preferred α-amino acid side groups in the meaning of $R^3$ are methyl (alanine), propan-2-yl (valine), 1-methylpropan-1-yl (isoleucine), 2-methylpropan-1-yl (leucine), benzyl (phenylalanine), imidazol-4-ylmethyl (histidine), hydroxymethyl (serine), 1-hydroxyethyl (threonine), carbamoylmethyl (asparagine), 2-carbamoylethyl (glutamine), carboxymethyl (aspartic acid), 2-carboxyethyl (glutamic acid), 4-aminobutan-1-yl (lysine), 3-aminopropan-1-yl (ornithine), 2-aminoethyl (2,4-diaminobutyric acid), aminomethyl (2,3-diaminopropionic acid), 3-guanidinopropan-1-yl (arginine). The L configuration is preferred in each case.

In the context of the present invention it is the case that, for all radicals which occur two or more times, their meaning is independent of one another. If radicals in the compounds according to the invention are substituted, the radicals, unless specified otherwise, may be substituted one or more times. In this context, substitution by one or by two identical or different substituents is preferred; particularly preferred is substitution by one substituent.

Preference is given, in the context of the present invention, to compounds of the formula (I) in which
$R^{PD}$ is a group of the formula

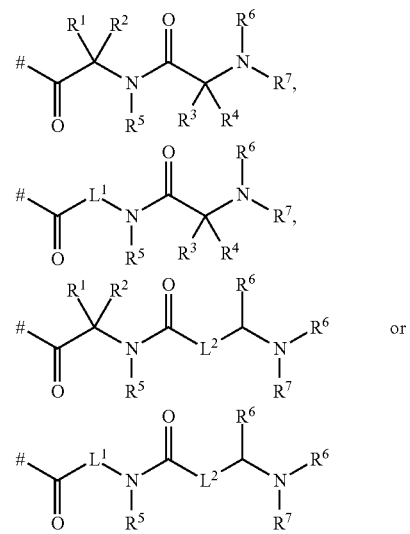

in which
\# means the point of linkage to the respective O atom,
$L^1$ is ethane-1,2-diyl,
$L^2$ is methanediyl or ethane-2-diyl,
$R^1$ is hydrogen, methyl, propan-2-yl, 1-methylpropan-1-yl, 2-methylpropan-1-yl, benzyl, p-hydroxybenzyl, hydroxymethyl or 1-hydroxyethyl,
$R^2$ is hydrogen,
$R^3$ is hydrogen, methyl, propan-2-yl, 1-methylpropan-1-yl, 2-methylpropan-1-yl, benzyl, imidazol-4-ylmethyl, hydroxymethyl, 1-hydroxyethyl, carbamoylmethyl, 2-carbamoylethyl, carboxymethyl, 2-carboxyethyl, 4-aminobutan-1-yl, 3-aminopropan-1-yl, 2-aminoethyl, aminomethyl or 3-guanidinopropan-1-yl,
$R^4$ is hydrogen,
$R^5$ is hydrogen or methyl
or
$R^5$ is linked to $R^1$ and both, together with the atoms to which they are attached, form a pyrrolidine ring,
$R^6$ is hydrogen or methyl
or
$R^6$ is linked to $R^3$ and both, together with the atoms to which they are attached, form a pyrrolidine ring,
$R^7$ is hydrogen or methyl
and
$R^8$ is hydrogen or carboxyl,
and the salts, solvates and solvates of the salts thereof.

Particular preference is given in the context of the present invention to compounds of the formula (I) in which $R^{PD}$ is a group of the formula

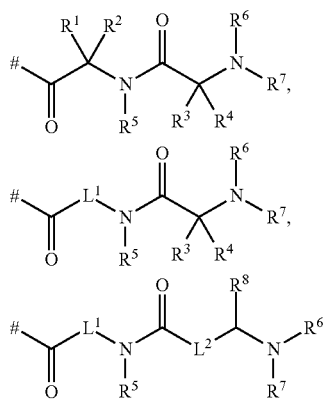

in which
# is the point of linkage to the respective O atom,
$L^1$ is ethane-1,2-diyl,
$L^2$ is methanediyl,
$R^1$ is hydrogen, methyl, propan-2-yl, 1-methylpropan-1-yl, 2-methylpropan-1-yl, hydroxymethyl or 1-hydroxyethyl,
$R^2$ is hydrogen,
$R^3$ is hydrogen, methyl, propan-2-yl, 1-methylpropan-1-yl, 2-methylpropan-1-yl, imidazol-4-ylmethyl, hydroxymethyl, 1-hydroxyethyl, 2-carboxyethyl, 4-aminobutan-1-yl, 3-aminopropan-1-yl or 2-aminoethyl,
$R^4$ is hydrogen,
$R^5$ is hydrogen,
$R^6$ is hydrogen or methyl
or
$R^6$ is linked to $R^3$ and both, together with the atoms to which they are attached, form a pyrrolidine ring,
$R^7$ is hydrogen
and
$R^8$ is hydrogen,
and the salts, solvates and solvates of the salts thereof.

The two prodrug groups $R^{PD}$ in the compounds of the formula (I) may be identical or different within the scope of the meanings indicated above. Preferred compounds of the formula (I) are those with prodrug groups $R^{PD}$ that are identical in each case.

Of particular importance are the compounds of the formulae (I-A) and (I-B)

(I-A)

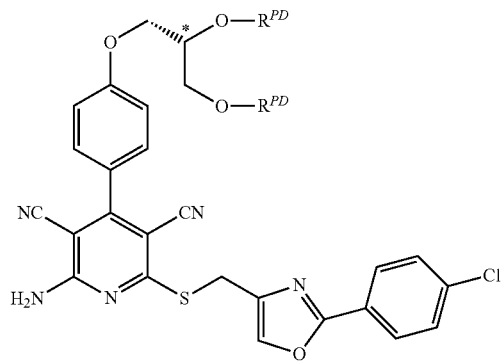

(I-B)

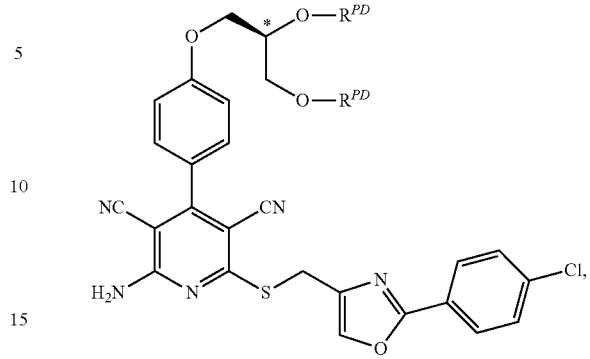

in which $R^{PD}$ has the meaning indicated above,
with an S- or R-configuration on the C* carbon atom of the propane-1,2,3-triyl group, and also the salts, solvates and solvates of the salts thereof.

Preferred in the context of the present invention are the compounds of the formula (I-A) with an S-configuration on the C* carbon atom of the propane-1,2,3-triyl group, and also the salts, solvates and solvates of the salts thereof.

Particularly preferred in the context of the present invention are compounds of the formula (I-A) in which the two prodrug groups $R^{PD}$ are each identical, and also the salts, solvates and solvates of the salts thereof.

Further provided by the invention is a process for preparing the compounds of the formula (I) according to the invention in which the two prodrug groups $R^{PD}$ are each identical, characterized in that the compound (A)

(A)

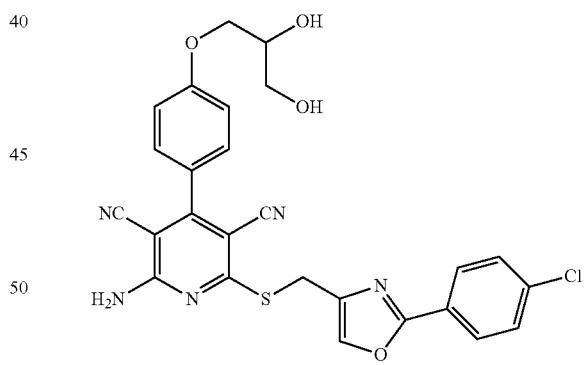

either
[A] is esterified in an inert solvent in the presence of a condensing agent initially with two or more equivalents of an amino acid of the formula (II) or (III)

(II)

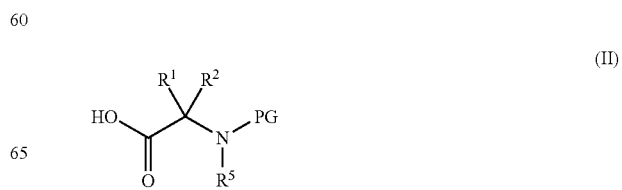

-continued

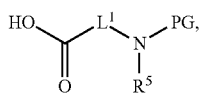
(III)

in which $L^1$, $R^1$, $R^2$ and $R^5$ have the meanings indicated above and

PG is a temporary amino protective group such as, for example, tert-butoxycarbonyl, to give a compound of the formula (IV) or (V)

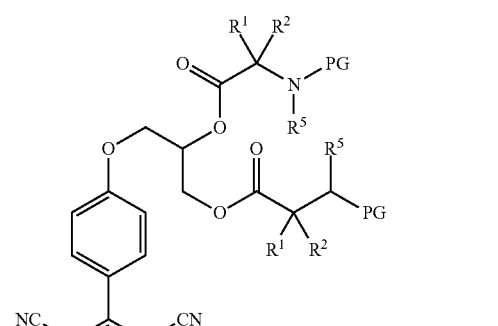
(IV)

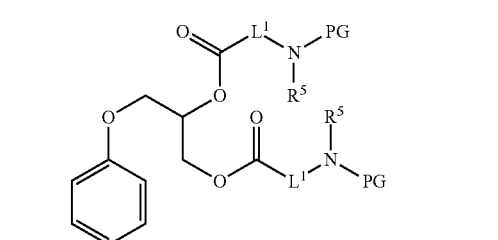
(V)

in which $L^1$, PG, $R^1$, $R^2$ and $R^5$ have the meanings indicated above, then, after elimination of the protective groups PG, this compound is coupled in an inert solvent in the presence of a condensing agent with two or more equivalents of an amino acid of the formula (VI) or (VII)

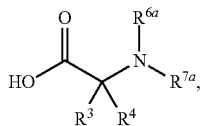
(VI)

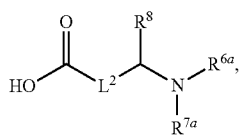
(VII)

in which $L^2$, $R^3$, $R^4$ and $R^8$ have the meanings indicated above and $R^{6a}$ and $R^{7a}$ are identical or different and have the meanings indicated above for $R^6$ and $R^7$, respectively, or are a temporary amino protective group, to give a compound of the formula (VIII), (IX), (X) or (XI)

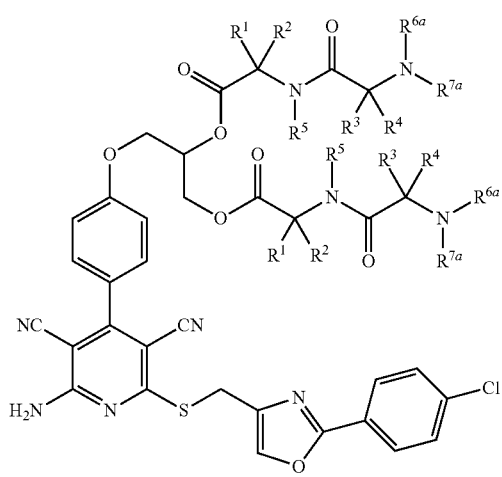
(VIII)

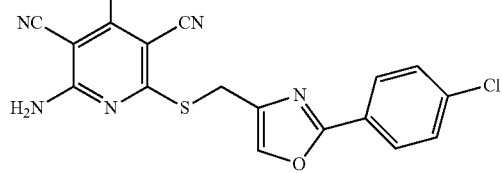
(IX)

(X)

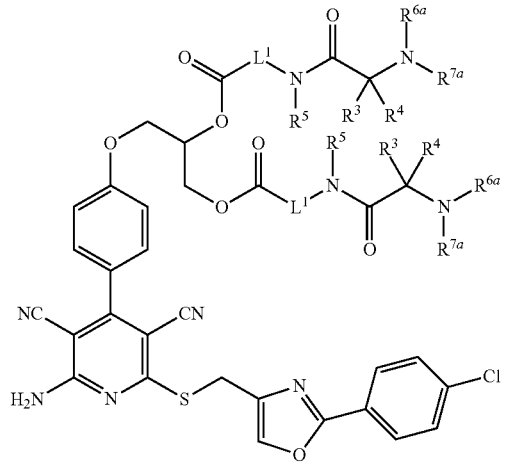

(XI)

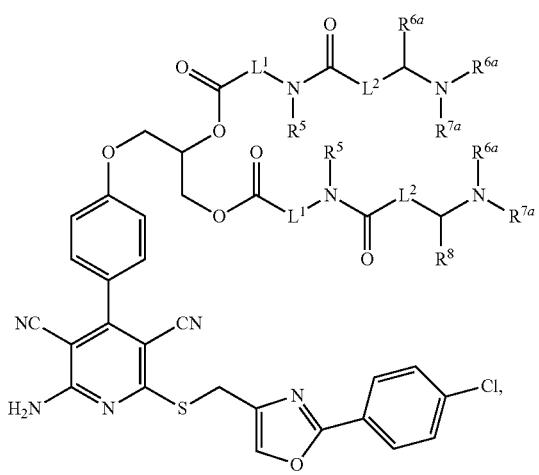

in which $L^1$, $L^2$, $R^2$, $R^3$, $R^4$, $R^5$, $R^{6a}$, $R^{7a}$ and $R^8$ each have the meanings indicated above, and subsequently any protective groups present are removed again, or

[B] is coupled in an inert solvent in the presence of a condensing agent with two or more equivalents of a carboxylic acid of the formula (XII), (XIII), (XIV) or (XV)

(XII)

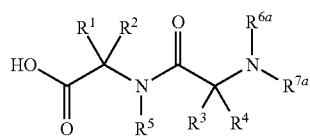

(XIII)

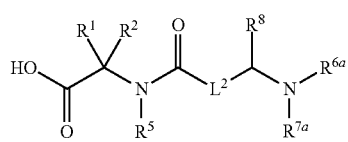

(XIV)

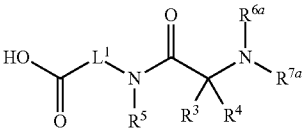

(XV)

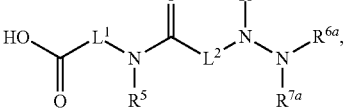

in which $L^1$, $L^2$, $R^1$, $R^2$, $R^3$, $R^4$, $R^5$ and $R^8$ have the meanings indicated above and $R^{6a}$ and $R^{7a}$ are identical or different and have the meanings indicated above for $R^6$ and $R^7$, respectively, or are a temporary amino protective group, to give one of the above-recited compounds (VIII), (IX), (X) or (XI), and subsequently any protective groups present are removed again and the compounds of the formula (I) resulting in each case are converted where appropriate with the appropriate (i) solvents and/or (ii) acids or bases into the solvates, salts and/or solvates of the salts thereof.

The transformation (A)→(I) thus takes place either by sequential coupling of the individual amino acid components which are suitably protected where appropriate (process variant [A]) or by direct acylation with a suitably protected dipeptoid derivative (process variant [B]). The coupling reactions (ester or amide formation) are in this case carried out by known methods of peptide chemistry [cf., for example, M. Bodanszky, *Principles of Peptide Synthesis*, Springer-Verlag, Berlin, 1993; H.-D. Jakubke and H. Jeschkeit, *Aminosäuren, Peptide, Proteine*, Verlag Chemie, Weinheim, 1982].

Examples of inert solvents for the coupling reactions are ethers such as diethyl ether, tert-butyl methyl ether, dioxane, tetrahydrofuran, glycol dimethyl ether or diethylene glycol dimethyl ether, hydrocarbons such as benzene, toluene, xylene, hexane, cyclohexane or petroleum fractions, halohydrocarbons such as dichloromethane, trichloromethane, tetrachloromethane, 1,2-dichloroethane, trichloroethylene or chlorobenzene, or other solvents such as acetone, ethyl acetate, pyridine, dimethyl sulfoxide, dimethylformamide, N,N'-dimethylpropyleneurea (DMPU), N-methylpyrrolidone (NMP) or acetonitrile. It is likewise possible to use mixtures of the solvents mentioned. Dichloromethane, dimethylformamide or mixtures of these two solvents are preferred.

Examples of suitable condensing agents in these coupling reactions are carbodiimides such as N,N'-diethyl-, N,N-dipropyl-, N,N-diisopropyl-, N,N'-dicyclohexylcarbodiimide (DCC) or N-(3-dimethylaminoisopropyl)-N'-ethylcarbodiimide hydrochloride (EDC), phosgene derivatives such as N,N-carbonyldiimidazole (CDI), 1,2-oxazolium compounds such as 2-ethyl-5-phenyl-1,2-oxazolium 3-sulfate or 2-tert-butyl-5-methylisoxazolium perchlorate, acylamino compounds such as 2-ethoxy-1-ethoxycarbonyl-1,2-dihydroquinoline, or isobutyl chloroformate, propanephosphonic anhydride, diethyl cyanophosphonate, bis-(2-oxo-3-oxazolidinyl)phosphoryl chloride, benzotriazol-1-yloxytris(dimethylamino)phosphonium hexafluorophosphate, benzotriazol-1-yloxytris(pyrrolidino)phosphonium hexafluorophosphate (PyBOP), O-(benzotriazol-1-yl)-N,N,N',N'-tetramethyluronium tetrafluoroborate (TBTU), O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU), O-(7-azabenzotriazol-1-yl)-N,N,N',N'-tetramethyluronium hexafluorophosphate (HATU) or O-(1H-6-chlorobenzotriazol-1-yl)-1,1,3,3-tetramethyluronium tetrafluoroborate (TCTU), where appropriate in combination with further auxiliaries such as 1-hydroxybenzotriazole (HOBt) or N-hydroxysuccinimide (HOSu), and as bases are alkali metal carbonates, e.g. sodium or potassium carbonate, or organic amine bases such as triethylamine, N-methylmorpholine, N-methylpiperidine, N,N-diisopropylethylamine or 4-N,N-dimethylaminopyridine. N-(3-Dimethylaminoisopropyl)-N'-ethylcarbodiimide hydrochloride (EDC) in combination with 4-N,N-dimethylaminopyridine is preferably employed for ester deformation. N-(3-Dimethylaminoisopropyl)-N'-ethylcarbodiimide hydrochloride (EDC) in combination with 1-hydroxybenzotriazole (HOBt) or N-hydroxysuccinimide (HOSu) and, where appropriate, a base such as N,N-diisopropylethylamine is preferably used for the amide formation.

The couplings are generally carried out in a temperature range from 0° C. to +60° C., preferably at +10° C. to +30° C. The reactions can take place under normal, under elevated or under reduced pressure (e.g. from 0.5 to 5 bar). They are generally carried out under atmospheric pressure.

The compounds of the formula (I) may also result directly in the form of their salts in the preparation by the processes described above. These salts can be converted where appropriate by treatment with a base or acid in an inert solvent, by chromatographic methods or by ion exchange resins, into the respective free bases or acids. Further salts of the compounds according to the invention can also be prepared where appropriate by exchange of counterions by means of ion exchange chromatography, for example with Amberlite® resins.

Functional groups which are present where appropriate in the compounds of the formulae (II), (VI), (VII), (XII), (XIII), (XIV) and (XV) and in the radicals $R^1$, $R^3$, $R^6$, $R^7$ and/or $R^8$—such as, in particular, amino, guanidine, hydroxy, mercapto and carboxyl groups—may, if expedient or necessary, also be in temporarily protected form in the reaction sequences described above. The introduction and removal of such protective groups takes place in this connection by conventional methods known from peptide chemistry [see, for example, T. W. Greene and P. G. M. Wuts, *Protective Groups in Organic Synthesis*, Wiley, New York, 1999; M. Bodanszky and A. Bodanszky, *The Practice of Peptide Synthesis*, Springer-Verlag, Berlin, 1984].

The amino and guanidine protective group which is preferably used is tert-butoxycarbonyl (Boc) or benzyloxycarbonyl (Z). The protective group preferably employed for a hydroxy or carboxyl function is preferably tert-butyl or benzyl. Elimination of these protective groups is carried out by conventional methods, preferably by reaction with a strong acid such as hydrogen chloride, hydrogen bromide or trifluoroacetic acid in an inert solvent such as dioxane, dichloromethane or acetic acid; the elimination can where appropriate also take place without an additional inert solvent. In the case of benzyl and benzyloxycarbonyl as protective group, these can also be removed by hydrogenolysis in the presence of a palladium catalyst. Elimination of the protective groups mentioned may where appropriate be carried out simultaneously in a one-pot reaction or in separate reaction steps.

The compounds of the formulae (II), (III), (VI), (VII), (XII), (XIII), (XIV) and (XV) are commercially available or known from the literature, or they can be prepared by methods customary in the literature.

Compounds of the formula (I) according to the invention in which the two prodrug groups $R^{PD}$ are not identical can be prepared, in analogy to the process described above, by coupling the compound (A) in separate steps with in each case one equivalent of correspondingly different compounds of the formulae (II), (III), (VI), (VII), (XII), (XIII), (XIV) and/or (XV) and then separating—where appropriate before or after the elimination of temporary protective groups—product mixtures that are produced in these coupling reactions into the individual components. For such separation it is preferred to use chromatographic methods, such as chromatography on silica gel or alumina or else HPLC chromatography on reversed phases, or recrystallization from aqueous or non-aqueous solvent mixtures.

The compound 2-amino-6-({[2-(4-chlorophenyl)-1,3-oxazol-4-yl]methyl}sulfanyl)-4-(4-{[2,3-dihydroxypropyl]oxy}phenyl)pyridine-3,5-dicarbonitrile of the formula (A) is prepared by first condensing the benzaldehyde of the formula (XVI)

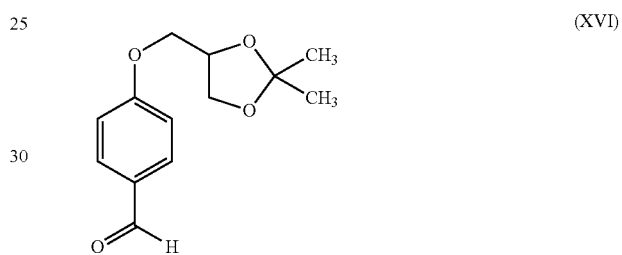

(XVI)

with two equivalents of 2-cyanothioacetamide in the presence of a base such as N-methylmorpholine to give the pyridine derivative (XVII)

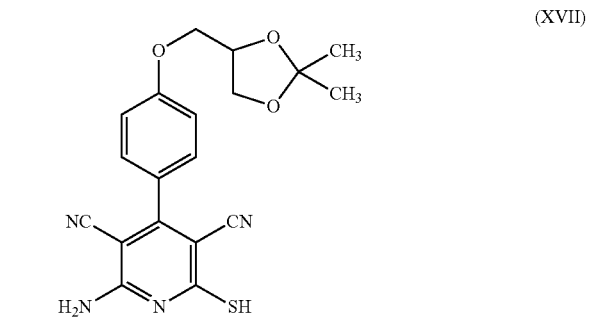 [SMILES: CC1(C)OCC(COc2ccc(-c3c(C#N)c(N)nc(S)c3C#N)cc2)O1]

(XVII)

then alkylating this compound in the presence of a base such as sodium hydrogencarbonate with 4-(chloromethyl)-2-(4-chlorophenyl)-1,3-oxazole of the formula (XVIII)

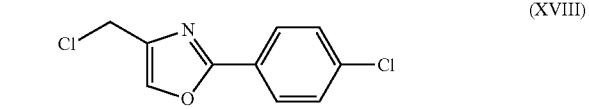

(XVIII)

to give the compound of the formula (XIX)

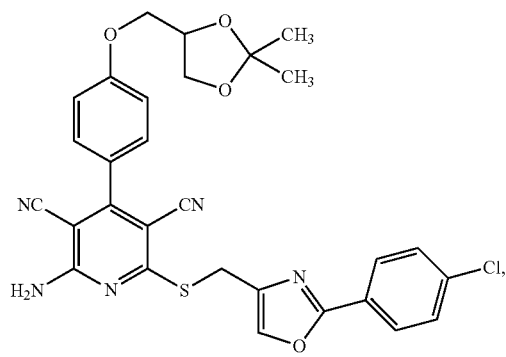

(XIX)

and finally eliminating the acetonide protective group by means of an aqueous acid, such as hydrochloric acid or acetic acid [see also reaction scheme 2 below, and also the description of intermediates 1A-9A in the Experimental section].

The compound of the formula (XVI) in turn is obtainable by reaction of 4-hydroxybenzaldehyde with the 3-chloro-1,2-propanediol acetonide of the formula (XX)

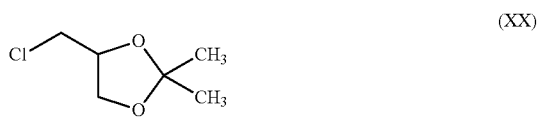

(XX)

in the presence of a base such as potassium carbonate. If, in this reaction, the enantiomerically pure 3-chloro-1,2-propanediol acetonides in R- or S-configuration are used, then, in accordance with the above-described reaction sequence, it is possible to obtain the corresponding enantiomers of the active ingredient compound (A) and also, derived from them, the corresponding prodrug compounds of the formulae (I-A) and (I-B).

The 2-phenyl-1,3-oxazole derivative of the formula (XVIII) can be prepared via condensation reactions that are known from the literature [cf. reaction scheme 3 below]. The preparation of the compounds (I) and of active ingredient compound (A) according to the invention can be illustrated by way of example by the following synthesis schemes:

Scheme 1 (part 1)

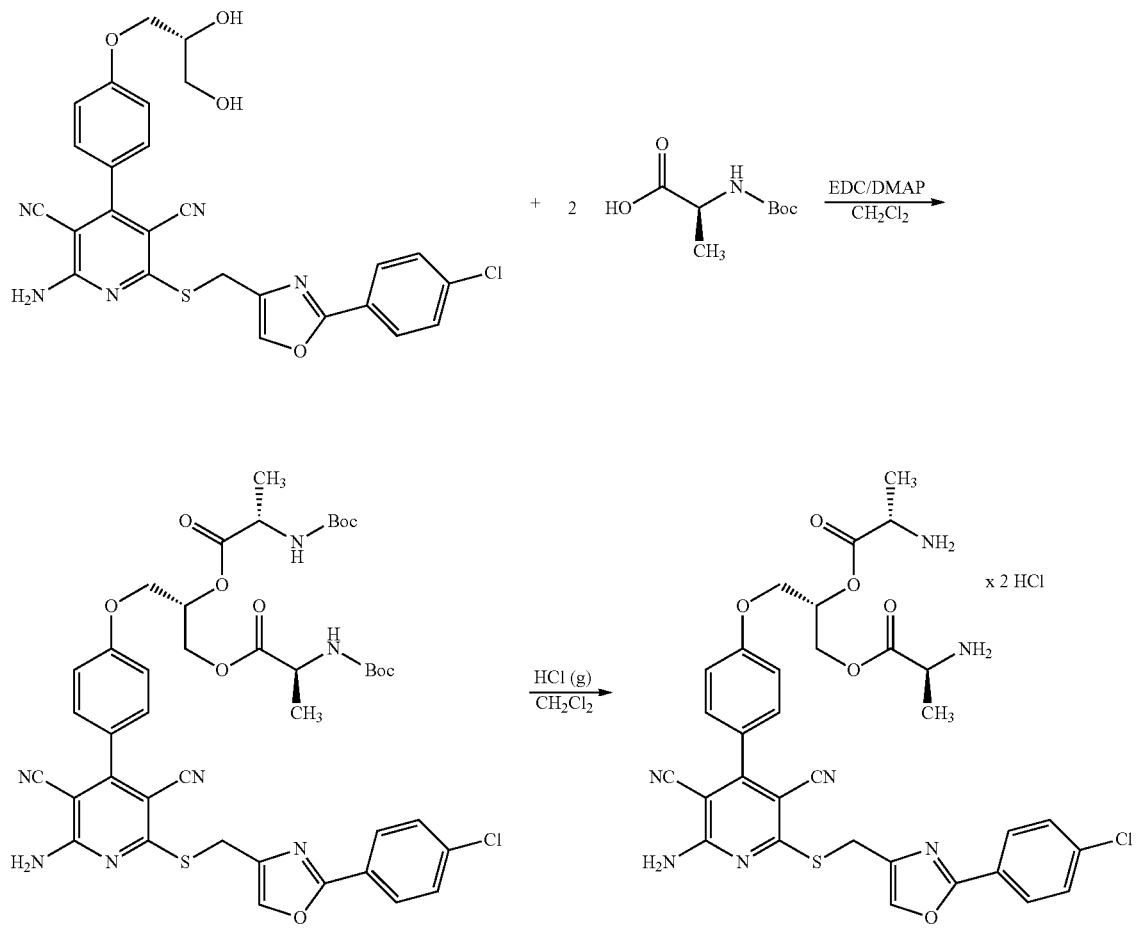

Scheme 1 (part 2)
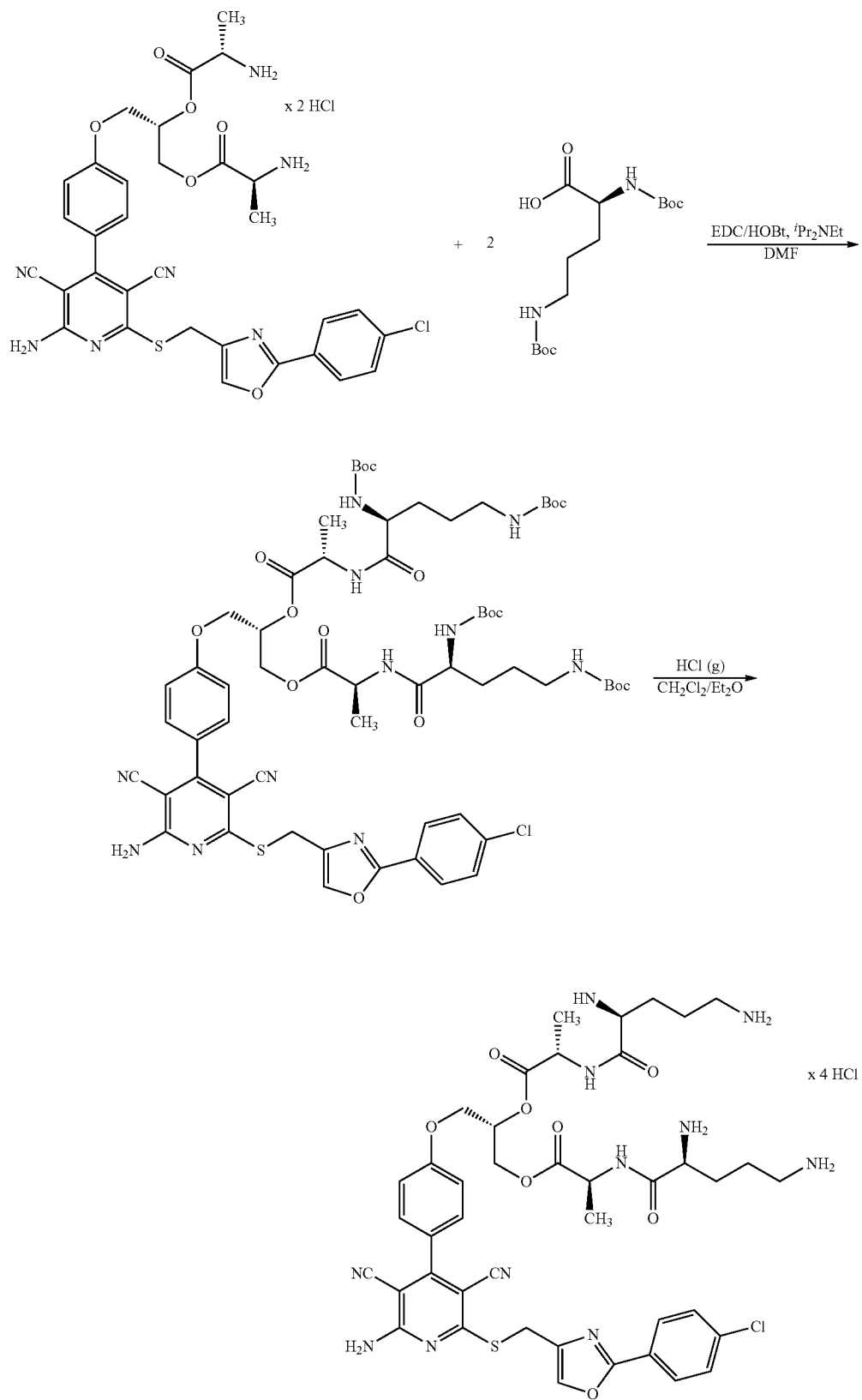

Scheme 2

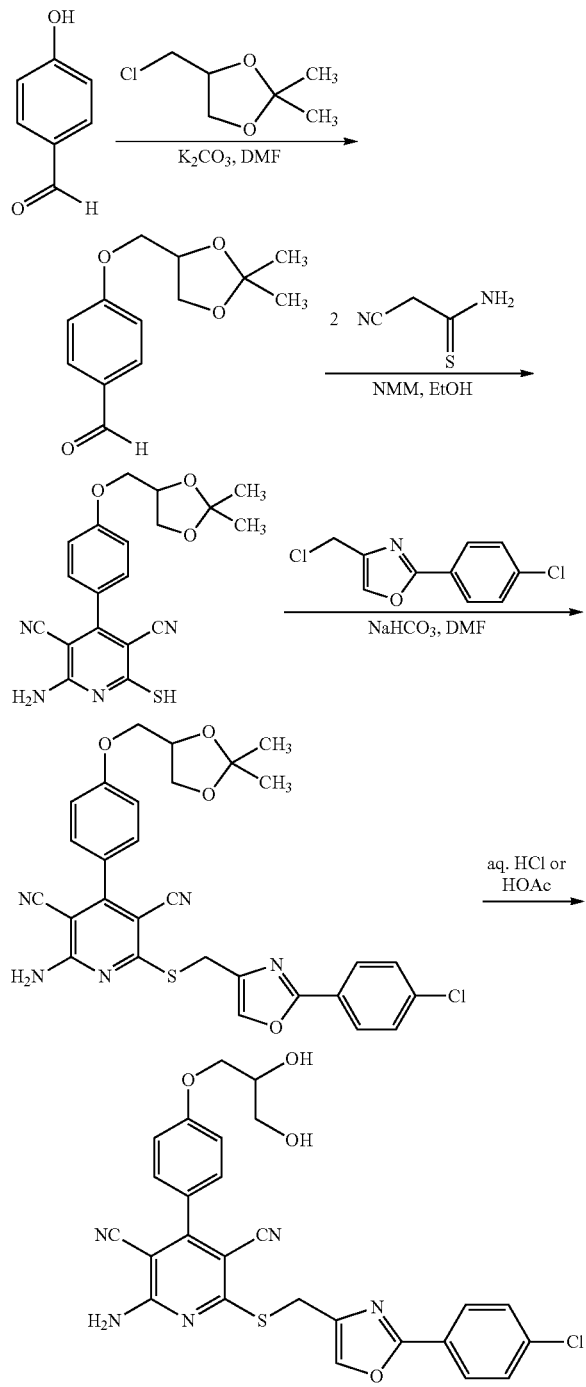

Scheme 3

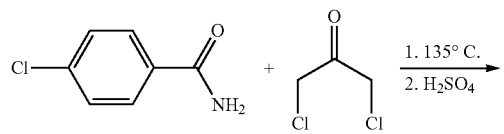

The compounds according to the invention and their salts represent useful prodrugs of the active substance (A). On the one hand, they show good stability at various pH values and, on the other hand, they show efficient conversion into the active ingredient compound (A) at a physiological pH and in particular in vivo. The compounds according to the invention moreover have improved solubilities in aqueous or other physiologically tolerated media, making them suitable for therapeutic use, in particular on intravenous administration. In addition, the bioavailability from suspension after oral administration is improved by comparison with the parent substance (A).

The compounds of the formula (I) are suitable alone or in combination with one or more other active ingredients for the prophylaxis and/or treatment of various disorders, for example and in particular disorders of the cardiovascular system (cardiovascular disorders), for cardio protection following lesions of the heart, and of metabolic disorders.

Disorders of the cardiovascular system, or cardiovascular disorders, mean in the context of the present invention for example the following disorders: hypertension (high blood pressure), peripheral and cardiac vascular disorders, coronary heart disease, coronary restenosis such as, for example, restenosis following balloon dilatation of peripheral blood vessels, myocardial infarction, acute coronary syndrome, acute coronary syndrome with ST elevation, acute coronary syndrome without ST elevation, stable and unstable angina pectoris, myocardial insufficiency, Prinzmetal angina, persistent ischemic dysfunction ("hibernating myocardium"), temporary postischemic dysfunction ("stunned myocardium"), heart failure, tachycardia, atrial tachycardia, arrhythmias, atrial and ventricular fibrillation, persistent atrial fibrillation, permanent atrial fibrillation, atrial fibrillation with normal left ventricular function, atrial fibrillation with impaired left ventricular function, Wolff-Parkinson-White syndrome, disturbances of peripheral blood flow, elevated levels of fibrinogen and of low density LDL, and elevated concentrations of plasminogen activator inhibitor 1 (PAI-1), especially hypertension, coronary heart disease, acute coronary syndrome, angina pectoris, heart failure, myocardial infarction and atrial fibrillation.

In the context of the present invention, the term heart failure includes both acute and chronic manifestations of heart failure, as well as more specific or related types of disease, such as acute decompensated heart failure, right heart failure, left heart failure, global failure, ischemic cardiomyopathy, dilated cardiomyopathy, congenital heart defects, heart valve defects, heart failure associated with heart valve defects, mitral stenosis, mitral insufficiency, aortic stenosis, aortic insufficiency, tricuspid stenosis, tricuspid insufficiency, pulmonary stenosis, pulmonary valve insufficiency, combined heart valve defects, myocardial inflammation (myocarditis), chronic myocarditis, acute myocarditis, viral myocarditis, diabetic heart failure, alcoholic cardiomyopathy, cardiac storage disorders, and diastolic and systolic heart failure.

The compounds according to the invention are further also suitable in particular for reducing the area of myocardium affected by an infarction, and for the prophylaxis of secondary infarctions.

The compounds according to the invention are furthermore suitable in particular for the prophylaxis and/or treatment of thromboembolic disorders, reperfusion damage following ischemia, micro- and macromuscular lesions (vasculitis), arterial and venous thromboses, edemas, ischemias such as myocardial infarction, stroke and transient ischemic attacks, for cardio protection in connection with coronary artery bypass operations (CABG), primary percutaneous transluminal coronary angioplasties (PTCAs), PTCAs after thrombolysis, rescue PTCA, heart transplants and open-heart operations, and for organ protection in connection with transplants, bypass operations, catheter investigations and other surgical procedures.

Further indication areas for which the compounds according to the invention can be used are for example the prophylaxis and/or treatment of disorders of the urogenital region, such as, for example, acute renal failure, unstable bladder, urogenital incontinence, erectile dysfunction and female sexual dysfunction, but also the prophylaxis and/or treatment of inflammatory disorders such as, for example, inflammatory dermatoses and arthritis, especially rheumatoid arthritis, of disorders of the central nervous system and neurodegenerative impairments (post-stroke conditions, Alzheimer's disease, Parkinson's disease, dementia, Huntington's chorea, epilepsy, depression, multiple sclerosis), of painful conditions and migraine, hepatic fibrosis and cirrhosis of the liver, of cancers and of nausea and vomiting in connection with cancer therapies, and for wound healing.

A further indication area is for example the prophylaxis and/or treatment of respiratory disorders such as, for example, asthma, chronic obstructive respiratory disorders (COPD, chronic bronchitis), pulmonary emphysema, bronchiectasies, cystic fibrosis (mucoviscidosis) and pulmonary hypertension, especially pulmonary aterial hypertension.

Finally, the compounds according to the invention are also suitable for the prophylaxis and/or treatment of metabolic disorders such as, for example, diabetes, especially diabetes mellitus, gestational diabetes, insulin-dependent diabetes and non-insulin-dependent diabetes, diabetic sequelae such as, for example, retinopathy, nephropathy and neuropathy, metabolic disorders such as, for example, metabolic syndrome, hyperglycemia, hyperinsulinemia, insulin resistance, glucose intolerance and obesity (adiposity), and arteriosclerosis and dyslipidemias (hypercholesterolemia, hypertriglyceridemia, elevated concentrations of post-prandial plasma triglycerides, hypoalphalipoproteinemia, combined hyperlipidemias), especially, of diabetes, metabolic syndrome and dyslipidemias.

The present invention further relates to the use of the compounds according to the invention for the treatment and/or prophylaxis of disorders, especially of the aforementioned disorders.

The present invention further relates to the use of the compounds according to the invention for the manufacture of a medicament for the treatment and/or prophylaxis of disorders, especially of the aforementioned disorders.

The present invention further relates to the use of the compounds according to the invention in a method for the treatment and/or prophylaxis of disorders, especially of the aforementioned disorders.

The present invention further relates to a method for the treatment and/or prophylaxis of disorders, especially of the aforementioned disorders, by using an effective amount of at least one of the compounds according to the invention.

The compounds according to the invention can be employed alone or, if required, in combination with other active ingredients. The present invention therefore further relates to medicaments comprising at least one of the compounds according to the invention and one or more further active ingredients, in particular for the treatment and/or prophylaxis of the aforementioned disorders.

Suitable combination active ingredients which may be mentioned by way of example and preferably are: lipid metabolism-altering active ingredients, antidiabetics, blood pressure-reducing agents, agents which promote blood flow and/or have antithrombotic effects, antiarrhythmics, antioxidants, chemokine receptor antagonists, p38 kinase inhibitors, NPY agonists, orexin agonists, anorectic agents, PAF-AH inhibitors, anti-inflammatory agents (COX inhibitors, $LTB_4$ receptor antagonists), and analgesics such as, for example, aspirin.

The present invention relates in particular to combinations of at least one of the compounds according to the invention with at least one lipid metabolism-altering active ingredient, antidiabetic, blood pressure reducing active ingredient, antiarrhythmic and/or agent having antithrombotic effects.

The compounds according to the invention can preferably be combined with one or more lipid metabolism-altering active ingredients, by way of example and preferably from the group of HMG-CoA reductase inhibitors, inhibitors of HMG-CoA reductase expression, squalene synthesis inhibitors, ACAT inhibitors, LDL receptor inducers, cholesterol absorption inhibitors, polymeric bile acid adsorbents, bile acid reabsorption inhibitors, MTP inhibitors, lipase inhibitors, LPL activators, fibrates, niacin, CETP inhibitors, PPAR-α, PPAR-γ and/or PPAR-δ agonists, RXR modulators, FXR modulators, LXR modulators, thyroid hormones and/or thyroid mimetics, ATP-citrate lyase inhibitors, Lp(a) antagonists, cannabinoid receptor 1 antagonists, leptin receptor agonists, bombesin receptor agonists, histamine receptor agonists, and of antioxidants/radical scavengers;

antidiabetics which are mentioned in the Rote Liste 2004/II, Chapter 12, and, by way of example and preferably, those from the group of sulfonylureas, biguanides, meglitinide derivatives, glucosidase inhibitors, inhibitors of dipeptidylpeptidase IV (DPP-IV inhibitors), oxadiazolidinones, thiazolidinediones, GLP 1 receptor agonists, glucagon antagonists, insulin sensitizers, CCK 1 receptor agonists, leptin receptor agonists, inhibitors of hepatic enzymes involved in the stimulation of gluconeogenesis and/or glycogenolysis, modulators of glucose uptake, and of potassium channel openers such as, for example, those disclosed in WO 97/26265 and WO 99/03861;

blood pressure-reducing active ingredients, by way of example and preferably from the group of calcium antagonists, angiotensin All antagonists, ACE inhibitors, rennin inhibitors, beta-adrenoceptor antagonists, alpha-adrenoceptor antagonists, diuretics, aldosterone antagonists, mineralocorticoid receptor antagonists, ECE inhibitors, and of vasopeptidase inhibitors;

agents having antithrombotic effects, by way of example and preferably from the group of platelet aggregation inhibitors or of anticoagulants;

antiarrhythmics, especially those for the treatment of supraventricular arrhythmias and tachycardias;

substances for the prophylaxis and treatment of ischemic and reperfusion damage;

vasopressin receptor antagonists;

organic nitrates and NO donors;

compounds with positive inotropic activity;

compounds which inhibit the degradation of cyclic guanosine monophosphate (cGMP) and/or cyclic adenosine monophosphate (cAMP), such as, for example, inhibitors of phosphodiesterases (PDE) 1, 2, 3, 4 and/or 5, especially PDE 5 inhibitors such as sildenafil, vardenafil and tadalafil, and PDE 3 inhibitors such as milrinone;

natriuretic peptides such as, for example, atrial natriuretic peptide (ANP, anaritide), B-type natriuretic peptide or brain natriuretic peptide (BNP, nesiritide), C-type natriuretic peptide (CNP) and urodilatin;

agonists of the prostacyclin receptor (IP receptor), such as, for example iloprost, beraprost and cicaprost;

calcium sensitizers such as by way of example and preferably levosimendan;

potassium supplements;

NO and heme-independent activators of guanylate cyclase, such as in particular the compounds described in WO 01/19355, WO 01/19776, WO 01/19778, WO 01/19780, WO 02/070462 and WO 02/070510;

NO-independent but heme-dependent stimulators of guanylate cyclase, such as in particular the compounds described in WO 00/06568, WO 00/06569, WO 02/42301 and WO 03/095451;

Inhibitors of human neutrophil elastase (HNE), such as, for example, sivelestat and DX-890 (reltran);

compounds which inhibit the signal transduction cascade, such as, for example, tyrosine kinase inhibitors, especially sorafenib, imatinib, gefitinib and erlotinib;

compounds which influence the energy metabolism of the heart, such as, for example, etomoxir, dichloroacetate, ranolazine and trimetazidine;

analgesics; and/or substances for the prophylaxis and treatment of nausea and vomiting Lipid metabolism-altering active ingredients preferably mean compounds from the group of HMG-CoA reductase inhibitors, squalene synthesis inhibitors, ACAT inhibitors, cholesterol absorption inhibitors, MTP inhibitors, lipase inhibitors, thyroid hormones and/or thyroid mimetics, niacin receptor agonists, CETP inhibitors, PPAR-α agonists, PPAR-γ agonists, PPAR-δ agonists, polymeric bile acid adsorbents, bile acid reabsorption inhibitors, antioxidants/radical scavengers, and cannabinoid receptor 1 antagonists.

In a preferred embodiment of the invention, the compounds according to the invention are administered in combination with an HMG-CoA reductase inhibitor from the class of statins, such as by way of example and preferably lovastatin, simvastatin, pravastatin, fluvastatin, atorvastatin, rosuvastatin, cerivastatin or pitavastatin.

In a preferred embodiment of the invention, the compounds according to the invention are administered in combination with a squalene synthesis inhibitor, such as by way of example and preferably BMS-188494 or TAK-475.

In a preferred embodiment of the invention, the compounds according to the invention are administered in combination with an ACAT inhibitor, such as by way of example and preferably avasimibe, melinamide, pactimibe, eflucimibe or SMP-797.

In a preferred embodiment of the invention, the compounds according to the invention are administered in combination with a cholesterol absorption inhibitor, such as by way of example and preferably ezetimibe, tiqueside or pamaqueside.

In a preferred embodiment of the invention, the compounds according to the invention are administered in combination with an MTP inhibitor, such as by way of example and preferably implitapide, BMS-201038, R-103757 or JTT-130.

In a preferred embodiment of the invention, the compounds according to the invention are administered in combination with a lipase inhibitor, such as by way of example and preferably orlistat.

In a preferred embodiment of the invention, the compounds according to the invention are administered in combination with a thyroid hormone and/or thyroid mimetic, such as by way of example and preferably D-thyroxine or 3,5,3'-triiodothyronine (T3).

In a preferred embodiment of the invention, the compounds according to the invention are administered in combination with an agonist of the niacin receptor, such as by way of example and preferably niacin, acipimox, acifran or radecol.

In a preferred embodiment of the invention, the compounds according to the invention are administered in combination with a CETP inhibitor, such as by way of example and preferably torcetrapib, JTT-705, BAY 60-5521, BAY 78-7499 or CETP vaccine (Avant).

In a preferred embodiment of the invention, the compounds according to the invention are administered in combination with a PPAR-γ agonist, such as by way of example and preferably pioglitazone or rosiglitazone.

In a preferred embodiment of the invention, the compounds according to the invention are administered in combination with a PPAR-δ agonist, such as by way of example and preferably GW-501516 or BAY 68-5042.

In a preferred embodiment of the invention, the compounds according to the invention are administered in combination with a polymeric bile acid adsorbent, such as by way of example and preferably cholestyramine, colestipol, colesolvam, CholestaGel or colestimide.

In a preferred embodiment of the invention, the compounds according to the invention are administered in combination with a bile acid reabsorption inhibitor, such as by way of example and preferably ASBT (=IBAT) inhibitors, such as, for example, AZD-7806, S-8921, AK-105, BARI-1741, SC-435 or SC-635.

In a preferred embodiment of the invention, the compounds according to the invention are administered in combination with an antioxidant/radical scavenger, such as by way of example and preferably probucol, AGI-1067, BO-653 or AEOL-10150.

In a preferred embodiment of the invention, the compounds according to the invention are administered in combination with a cannabinoid receptor 1 antagonist, such as by way of example and preferably rimonabant or SR-147778.

Antidiabetics preferably mean insulin and insulin derivatives, and orally active hypoglycemic active ingredients. Insulin and insulin derivatives includes in this connection both insulins of animal, human or biotechnological origin and mixtures thereof. The orally active hypoglycemic active ingredients preferably include sulfonylureas, biguanides, meglitinide derivatives, glucosidase inhibitors, DPP-IV inhibitors and PPAR-γ agonists.

In a preferred embodiment of the invention, the compounds according to the invention are administered in combination with insulin.

In a preferred embodiment of the invention, the compounds according to the invention are administered in combination with a sulfonylurea, such as by way of example and preferably tolbutamide, glibenclamide, glimepiride, glipizide or gliclazide.

In a preferred embodiment of the invention, the compounds according to the invention are administered in combination with a biguanide, such as by way of example and preferably metformin.

In a preferred embodiment of the invention, the compounds according to the invention are administered in combination with a meglitinide derivative, such as by way of example and preferably repaglinide or nateglinide.

In a preferred embodiment of the invention, the compounds according to the invention are administered in combination with a glucosidase inhibitor, such as by way of example and preferably miglitol or acarbose.

In a preferred embodiment of the invention, the compounds according to the invention are administered in combination with a DPP-IV inhibitor, such as by way of example and preferably sitagliptin or vildagliptin.

In a preferred embodiment of the invention, the compounds according to the invention are administered in combination with a PPAR-γ agonist, for example from the class of thiazolidinediones, such as by way of example and preferably pioglitazone or rosiglitazone.

Blood pressure-reducing agents preferably mean compounds from the group of calcium antagonists, angiotensin All antagonists, ACE inhibitors, renin inhibitors, beta-adrenoceptor antagonists, alpha-adrenoceptor antagonists and diuretics.

In a preferred embodiment of the invention, the compounds according to the invention are administered in combination with a calcium antagonist, such as by way of example and preferably nifedipine, amlodipine, verapamil or diltiazem.

In a preferred embodiment of the invention, the compounds according to the invention are administered in combination with an angiotensin All antagonist, such as by way of example and preferably losartan, valsartan, candesartan, embusartan, olmesartan or telmisartan.

In a preferred embodiment of the invention, the compounds according to the invention are administered in combination with an ACE inhibitor, such as by way of example and preferably enalapril, captopril, lisinopril, ramipril, delapril, fosinopril, quinopril, perindopril or trandopril.

In a preferred embodiment of the invention, the compounds according to the invention are administered in combination with a renin inhibitor, such as by way of example and preferably aliskiren, SPP-600 or SPP-800.

In a preferred embodiment of the invention, the compounds according to the invention are administered in combination with a beta-adrenoceptor antagonist, such as by way of example and preferably propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with an alpha-adrenoceptor antagonist, such as by way of example and preferably prazosin.

In a preferred embodiment of the invention, the compounds according to the invention are administered in combination with a diuretic, such as by way of example and preferably furosemide, bumetanide, torsemide, bendroflumethiazide, chlorthiazide, hydrochlorthiazide, hydroflumethiazide, methyclothiazide, polythiazide, trichlormethiazide, chlorthalidone, indapamide, metolazone, quinethazone, acetazolamide, dichlorphenamide, methazolamide, glycerol, isosorbide, mannitol, amiloride or triamterene.

In a preferred embodiment of the invention, the compounds according to the invention are administered in combination with an aldosterone or mineralocorticoid receptor antagonist, such as by way of example and preferably spironolactone or eplerenone.

In a preferred embodiment of the invention, the compounds according to the invention are administered in combination with a vasopressin receptor antagonist, such as by way of example and preferably conivaptan, tolvaptan, lixivaptan or SR-121463.

In a preferred embodiment of the invention, the compounds according to the invention are administered in combination with an organic nitrate or NO donor, such as by way of example and preferably sodium nitroprusside, glycerol nitrate, isosorbide mononitrate, isosorbide dinitrate, molsidomine or SIN-1, or in combination with inhaled NO.

In a preferred embodiment of the invention, the compounds according to the invention are administered in combination with a compound having positive inotropic activity, such as by way of example and preferably cardiac glycosides (digoxin) and beta-adrenergic and dopaminergic agonists such as isoproterenol, adrenaline, noradrenaline, dopamine or dobutamine.

In a preferred embodiment of the invention, the compounds according to the invention are administered in combination with antisympathotonics such as reserpine, clonidine or alpha-methyldopa, or in combination with potassium channel agonists such as minoxidil, diazoxide, dihydralazine or hydralazine.

Agents having an antithrombotic effect preferably mean compounds from the group of platelet aggregation inhibitors or of anticoagulants.

In a preferred embodiment of the invention, the compounds according to the invention are administered in combination with a platelet aggregation inhibitor, such as by way of example and preferably aspirin, clopidogrel, ticlopidine or dipyridamole.

In a preferred embodiment of the invention, the compounds according to the invention are administered in combination with a thrombin inhibitor, such as by way of example and preferably ximelagatran, melagatran, bivalirudin or clexane.

In a preferred embodiment of the invention, the compounds according to the invention are administered in combination with a GPIIb/IIIa antagonist, such as by way of example and preferably tirofiban or abciximab.

In a preferred embodiment of the invention, the compounds according to the invention are administered in combination with a factor Xa inhibitor, such as by way of example and preferably rivaroxaban (BAY 59-7939), DU-176b, apixaban, otamixaban, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds according to the invention are administered in combination with heparin or a low molecular weight (LMW) heparin derivative.

In a preferred embodiment of the invention, the compounds according to the invention are administered in combination with a vitamin K antagonist, such as by way of example and preferably coumarin.

Antiarrhythmics preferably means substances from the group of class Ia antiarrhythmics (e.g. quinidine), of class Ic antiarrhythmics (e.g. flecamide, propafenone), of class II antiarrhythmics (e.g. metoprolol, atenolol, sotalol, oxprenolol and other beta-receptor blockers), of class III antiarrhythmics (e.g. sotalol, amiodarone) and of class IV antiarrhythmics (e.g. digoxin, and verapamil, diltiazem and other calcium antagonists). Particular preference is given in the context of the present invention to combinations comprising at least one of the compounds according to the invention and one or more further active ingredients selected from the group consisting of HMG-CoA reductase inhibitors (statins), diuretics, beta-adrenoceptor antagonists, alpha-adrenoceptor antagonists, organic nitrates and NO donors, calcium antagonists, ACE inhibitors, angiotensin AII antagonists, aldosterone and mineralocorticoid receptor antagonists, vasopressin receptor antagonists, platelet aggregation inhibitors, anticoagulants and antiarrhythmics, and to the use thereof for the treatment and/or prophylaxis of the aforementioned disorders.

The present invention further relates to medicaments which comprise at least one compound according to the invention, normally together with one or more inert, non-toxic, pharmaceutically suitable excipients, and to the use thereof for the aforementioned purposes.

The compounds according to the invention can act systemically and/or locally. For this purpose, they can be administered in a suitable way such as, for example, by the oral, parenteral, pulmonary, nasal, sublingual, lingual, buccal, rectal, dermal, transdermal, conjunctival or otic route or as an implant or stent. The compounds according to the invention can be administered in administration forms suitable for these administration routes.

Suitable for oral administration are administration forms which function according to the prior art and deliver the compounds according to the invention rapidly and/or in modified fashion, and which contain the compounds according to the invention in crystalline and/or amorphized and/or dissolved form, such as, for example, tablets (uncoated or coated tablets, for example having enteric coatings or coatings which are insoluble or dissolve with a delay and control the release of the compound according to the invention), tablets which disintegrate rapidly in the mouth, or films/wafers, films/lyophilizates, capsules (for example hard or soft gelatin capsules), sugar-coated tablets, granules, pellets, powders, emulsions, suspensions, aerosols or solutions. Parenteral administration can take place with avoidance of an absorption step (e.g. intravenous, intraarterial, intracardiac, intraspinal or intralumbar) or with inclusion of an absorption (e.g. intramuscular, subcutaneous, intracutaneous, percutaneous or intraperitoneal). Administration forms suitable for parenteral administration are, inter alia, preparations for injection and infusion in the form of solutions, suspensions, emulsions, lyophilizates or sterile powders.

Suitable for the other administration routes are, for example, pharmaceutical forms for inhalation (inter alia powder inhalers, nebulizers), nasal drops, solutions or sprays, tablets for lingual, sublingual or buccal administration, films/wafers or capsules, suppositories, preparations for the eyes or ears, vaginal capsules, aqueous suspensions (lotions, shaking mixtures), lipophilic suspensions, ointments, creams, transdermal therapeutic systems (such as, for example, patches), milk, pastes, foams, dusting powders, implants or stents.

Oral or parenteral administration is preferred, especially oral and intravenous administration.

The compounds according to the invention can be converted into the stated administration forms. This can take place in a manner known per se by mixing with inert, non-toxic, pharmaceutically suitable excipients. These excipients include, inter alia, carriers (for example microcrystalline cellulose, lactose, mannitol), solvents (e.g. liquid polyethylene glycols), emulsifiers and dispersants or wetting agents (for example sodium dodecyl sulfate, polyoxysorbitan oleate), binders (for example polyvinylpyrrolidone), synthetic and natural polymers (for example albumin), stabilizers (e.g. antioxidants such as, for example, ascorbic acid), colorants (e.g. inorganic pigments such as, for example, iron oxides) and masking flavors and/or odors.

It has generally proved advantageous to administer on parenteral administration amounts of about 0.001 to 1 mg/kg, preferably about 0.01 to 0.5 mg/kg, of body weight to achieve effective results, and on oral administration the dosage is about 0.01 to 100 mg/kg, preferably about 0.01 to 20 mg/kg, and very particularly preferably 0.1 to 10 mg/kg, of body weight.

It may nevertheless be necessary where appropriate to deviate from the stated amounts, in particular as a function of the body weight, route of administration, individual response to the active ingredient, nature of the preparation and time or interval over which administration takes place. Thus, it may be sufficient in some cases to make do with less than the aforementioned minimum amount, whereas in other cases the stated upper limit must be exceeded. It may in the event of administration of larger amounts be advisable to divide these into a plurality of individual doses over the day.

The following exemplary embodiments illustrate the invention. The invention is not restricted to the examples.

The percentage data in the following tests and examples are, unless indicated otherwise, percentages by weight; parts are parts by weight. Solvent ratios, dilution ratios and concentration data for the liquid/liquid solutions are in each case based on volume.

A. EXAMPLES

Abbreviations and Acronyms

Ac Acetyl
aq. aqueous, aqueous solution
Boc Tert-Butoxycarbonyl
conc. concentrated
DMAP 4-N,N-Dimethylaminopyridine
DMF N,N-Dimethylformamide
DMSO Dimethyl sulfoxide
EDC 1-(3-Dimethylaminopropyl)-3-ethylcarbodiimide hydrochloride
ESI Electrospray ionization (in MS)
Et Ethyl
h Hour(s)
HOAc Acetic acid
HOBt 1-Hydroxy-1H-benzotriazole-hydrate
HPLC High pressure, high performance liquid chromatography
$^i$Pr Isopropyl
LC-MS Coupled liquid chromatography-mass spectrometry
min Minute(s)
MS Mass spectrometry
NMM N-Methylmorpholine
NMR Nuclear magnetic resonance spectrometry
p para
quant. quantitative (for yield)
RT Room temperature
$R_t$ Retention time (in HPLC)
sat. saturated
tert. Tertiary
TFA Trifluoroacetic acid
THF Tetrahydrofuran
UV Ultraviolet spectrometry
v/v Volume to volume ratio (of a solution)
Z Benzyloxycarbonyl
LC-MS Methods:
Method 1:
 MS instrument type: Micromass ZQ; HPLC instrument type: Waters Alliance 2795; column: Merck Chromolith SpeedROD RP-18e 50 mm×4.6 mm; eluent A: 1 l water+0.5 ml 50% formic acid, eluent B: 1 l acetonitrile+0.5 ml 50% formic acid; gradient: 0.0 min 10% B→3.0 min 95% B→4.0 min 95% B; flow rate: 0.0 min 1.0 ml/min→3.0 min 3.0 ml/min→4.0 min 3.0 ml/min; oven: 35° C.; UV detection: 210 nm.

Method 2:

Instrument: Micromass Platform LCZ with HPLC Agilent Series 1100; column: Thermo Hypersil GOLD 3µ, 20 mm×4 mm; eluent A: 1 l water+0.5 ml 50% formic acid, eluent B: 1 l acetonitrile+0.5 ml 50% formic acid; gradient: 0.0 min 100% A→0.2 min 100% A→2.9 min 30% A→3.1 min 10% A→5.5 min 10% A; oven: 50° C.; flow rate: 0.8 ml/min; UV detection: 210 nm.

Method 3:

MS instrument type: Waters ZQ; HPLC instrument type: Waters Alliance 2795; column: Phenomenex Onyx Monolithic C18, 100 mm×3 mm; eluent A: 1 l water+0.5 ml 50% formic acid, eluent B: 1 l acetonitrile+0.5 ml 50% formic acid; gradient: 0.0 min 90% A→2 min 65% A→4.5 min 5% A→6 min 5% A; flow rate: 2 ml/min; oven: 40° C.; UV detection: 210 nm.

Method 4:

Instrument: Micromass Quattro LCZ with HPLC Agilent Series 1100; UV DAD; column: Phenomenex Gemini 3µ 30 mm×3.00 mm; eluent A: 1 l water+0.5 ml 50% formic acid, eluent B: 1 l acetonitrile+0.5 ml 50% formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 208-400 nm.

Method 5:

Instrument: Micromass Quattro Premier with Waters HPLC Acquity; column: Thermo Hypersil GOLD 1.9µ, 50 mm×1 mm; eluent A: 1 l water+0.5 ml 50% formic acid, eluent B: 1 l acetonitrile+0.5 ml 50% formic acid; gradient: 0.0 min 90% A→0.1 min 90% A→1.5 min 10% A→2.2 min 10% A; flow rate: 0.33 ml/min; oven: 50° C.; UV detection: 210 nm.

Method 6:

MS instrument type: Micromass ZQ; HPLC instrument type: Waters Alliance 2795; column: Phenomenex Synergi 2.5µ MAX-RP 100A Mercury 20 mm×4 mm; eluent A: 1 l water+0.5 ml 50% formic acid, eluent B: 1 l acetonitrile+0.5 ml 50% formic acid; gradient: 0.0 min 90% A→0.1 min 90% A→3.0 min 5% A→4.0 min 5% A→4.01 min 90% A; flow rate: 2 ml/min; oven: 50° C.; UV detection: 210 nm.

Method 7:

MS instrument type: Micromass ZQ; HPLC instrument type: HP 1100 Series; UV DAD; column: Phenomenex Gemini 3µ 30 mm×3.00 mm; eluent A: 1 l water+0.5 ml 50% formic acid, eluent B: 1 l acetonitrile+0.5 ml 50% formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.

Method 8:

Instrument: Waters Acquity SQD HPLC system; column: Waters Acquity HPLC HSS T3 1.8µ 50 mm×1 mm; eluent A: 1 l water+0.25 ml 99% formic acid, eluent B: 1 l acetonitrile+0.25 ml 99% formic acid; gradient: 0.0 min 90% A→1.2 min 5% A→2.0 min 5% A; flow rate: 0.40 ml/min; oven: 50° C.; UV detection: 210-400 nm.

Method 9:

MS instrument type: M-40 DCI (NH$_3$); HPLC instrument type: HP 1100 with DAD detection; column: Kromasil 100 RP-18, 60 mm×2.1 mm, 3.5 µm; eluent A: 5 ml HClO$_4$ (70%)/liter water, eluent B: acetonitrile; gradient: 0 min 2% B→0.5 min 2% B→4.5 min 90% B→6.5 min 90% B→6.7 min 2% B→7.5 min 2% B; flow rate: 0.75 ml/min; column temperature: 30° C.; UV detection: 210 nm.

Method 10:

Instrument: Micromass Quattro Micro MS with HPLC Agilent series 1100; column: Thermo Hypersil GOLD 3µ 20 mm×4 mm; eluent A: 1 l water+0.5 ml 50% formic acid, eluent B: 1 l acetonitrile+0.5 ml 50% formic acid; gradient: 0.0 min 100% A→3.0 min 10% A→4.0 min 10% A→4.01 min 100% A (flow rate 2.5 ml/min)→5.00 min 100% A; oven: 50° C.; flow rate: 2 ml/min; UV detection: 210 nm.

Method 11:

Instrument: Micromass Quattro LCZ with HPLC Agilent Series 1100; column: Phenomenex Synergi 2µ Hydro-RP Mercury 20 mm×4 mm; eluent A: 1 l water+0.5 ml 50% formic acid, eluent B: 1 l acetonitrile+0.5 ml 50% formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 208-400 nm.

Starting Compounds and Intermediates

Example 1A

4-{[(4S)-2,2-Dimethyl-1,3-dioxolan-4-yl]methoxy}benzaldehyde

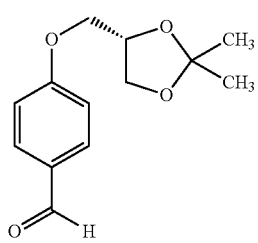 [SMILES: CC1(C)OC[C@H](COc2ccc(C=O)cc2)O1]

An amount of 12.5 g (102.4 mmol) of 4-hydroxybenzaldehyde were introduced under argon in 166 ml of dry DMF and admixed at RT with 42.4 g (307.1 mmol) of potassium carbonate and also 20.05 g (133.1 mmol) of (R)-(−)-3-chloro-1,2-propanediol acetonide. The batch was stirred at 160° C. for 16 hours. The batch was then admixed with water and extracted twice with ethyl acetate. The combined organic phases were washed with saturated aqueous sodium chloride solution and dried over magnesium sulfate. Following filtration, the solvent was removed on a rotary evaporator and the residue was purified by means of column chromatography on silica gel (eluent: cyclohexane/ethyl acetate 10:2).

Yield: 20.0 g (82% of theory)

$^1$H-NMR (400 MHz, DMSO-d$_6$): δ=9.89 (s, 1H), 7.85 (d, 2H), 7.03 (d, 2H), 4.50 (q, 1H), 4.22-4.09 (m, 2H), 4.04 (dd, 1H), 3.92 (dd, 1H), 1.48 (s, 3H), 1.41 (s, 3H).

LC-MS (method 9): R$_t$=4.02 min; MS (ESIpos): m/z=254 [M+NH$_4$]$^+$.

Example 2A

4-{[(4R)-2,2-Dimethyl-1,3-dioxolan-4-yl]methoxy}benzaldehyde

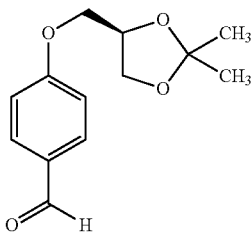 [SMILES: CC1(C)OC[C@@H](COc2ccc(C=O)cc2)O1]

An amount of 31.2 g (255.4 mmol) of 4-hydroxybenzaldehyde was introduced in 400 ml of dry DMF and admixed at RT with 105.7 g (766.1 mmol) of potassium carbonate and also 50.0 g (332.0 mmol) of (S)-(−)-3-chloro-1,2-propanediol acetonide. The batch was stirred at 160° C. for 16 hours. The batch was then admixed with 4000 ml of water and extracted with three times 500 ml of ethyl acetate. The combined organic phases were washed once each with 500 ml of water and 500 ml of saturated aqueous sodium chloride solution. After drying over magnesium sulfate, the solvent was removed on a rotary evaporator and the residue was purified by column chromatography on silica gel 60 (eluent gradient: ethyl acetate/petroleum ether 1:9→2:8).

Yield: 40.4 g (63% of theory)

$^1$H-NMR (400 MHz, DMSO-$d_6$): δ=9.90 (s, 1H), 7.85 (d, 2H), 7.03 (d, 2H), 4.50 (q, 1H), 4.22-4.09 (m, 2H), 4.04 (dd, 1H), 3.92 (dd, 1H), 1.48 (s, 3H), 1.41 (s, 3H).

LC-MS (method 9): $R_t$=3.97 min; MS (ESIpos): m/z=254 $[M+NH_4]^+$.

Example 3A

2-Amino-4-(4-{[(4S)-2,2-dimethyl-1,3-dioxolan-4-yl]methoxy}phenyl)-6-mercaptopyridine-3,5-dicarbonitrile

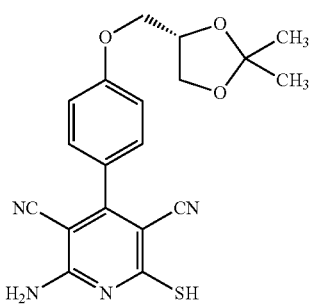 [SMILES: CC1(C)OC[C@H](COc2ccc(-c3c(C#N)c(N)nc(S)c3C#N)cc2)O1]

An amount of 44.0 g (186.2 mmol) of the compound from example 1A and 37.3 g (372.5 mmol) of cyanothioacetamide were introduced in 800 ml of ethanol. The reaction mixture was admixed at room temperature with 37.6 g (372.5 mmol) of 4-methylmorpholine and heated at reflux with stirring for 3 hours. After cooling to RT, it was stirred at this temperature for a further 16 hours. The precipitate was isolated by suction filtration, washed with ethanol and dried under reduced pressure. The product was used without further purification in the subsequent reaction.

Yield: 22.8 g (32% of theory)

$^1$H-NMR (400 MHz, DMSO-$d_6$): δ=7.69-7.37 (br. s, 2H), 7.42 (d, 2H), 7.10 (d, 2H), 4.48-4.39 (m, 1H), 4.15-4.02 (m, 2H), 3.78 (dd, 1H), 3.66 (dd, 1H), 2.77-2.68 (br. s, 1H), 1.37 (s, 3H), 1.31 (s, 3H).

LC-MS (method 1): $R_t$=1.75 min; MS (ESIpos): m/z=383 $[M+H]^+$.

Example 4A

2-Amino-4-(4-{[(4R)-2,2-dimethyl-1,3-dioxolan-4-yl]methoxy}phenyl)-6-mercaptopyridine-3,5-dicarbonitrile

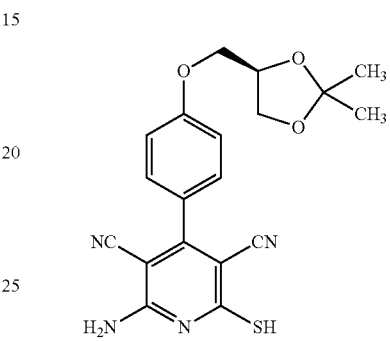

An amount of 40.4 g (171.0 mmol) of the compound from example 2A and 34.2 g (342.0 mmol) of cyanothioacetamide were introduced in 700 ml of ethanol. The reaction mixture was admixed with 34.5 g (342.0 mmol) of 4-methylmorpholine and heated at reflux with stirring for 3 hours. After cooling to RT, it was stirred at this temperature for a further 16 hours. The precipitate was isolated by suction filtration, washed with around 100 ml of ethanol and dried in a drying cabinet. The product was used without further purification in the subsequent reaction.

Yield: 19.5 g (29% of theory)

$^1$H-NMR (400 MHz, DMSO-$d_6$): δ=7.63-7.31 (br. s, 2H), 7.41 (d, 2H), 7.09 (d, 2H), 4.49-4.38 (m, 1H), 4.15-3.99 (m, 2H), 3.78 (dd, 1H), 3.66 (dd, 1H), 2.77-2.68 (br. s, 1H), 1.37 (s, 3H), 1.32 (s, 3H).

LC-MS (method 11): $R_t$=1.95 min; MS (ESIpos): m/z=424 $[M+H+ CH_3CN]^+$.

Example 5A 4-(Chloromethyl)-2-(4-chlorophenyl)-1,3-oxazole

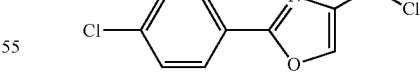

An amount of 123.8 g (795.5 mmol) of 4-chlorobenzenecarboxamide and 101.0 g (795.5 mmol) of 1,3-dichloroacetone were stirred at 135° C. for an hour. A melt was formed. The batch was subsequently cooled to RT with stirring, and at this temperature it was admixed cautiously with 200 ml of concentrated sulfuric acid and stirred for 30 minutes. The resulting suspension was poured into ice-water and stirred for a further 30 minutes. The precipitate formed was then isolated by suction filtration, washed with water and purified by flash chromatography on silica gel (eluent: dichloromethane). The solvent was removed on a rotary evaporator and the residue was dried under reduced pressure. This gave 95.5 g (53% of theory) of the target compound.

$^1$H-NMR (400 MHz, DMSO-d$_6$): δ=8.30 (s, 1H), 7.99 (d, 2H), 7.62 (d, 2H), 4.75 (s, 2H).

LC-MS (method 2): R$_t$=3.78 min; MS (ESIpos): m/z=228 [M+H]$^+$.

Example 6A

2-Amino-6-({[2-(4-chlorophenyl)-1,3-oxazol-4-yl]methyl}sulfanyl)-4-(4-{[(4S)-2,2-dimethyl-1,3-dioxolan-4-yl]methoxy}phenyl)pyridine-3,5-dicarbonitrile

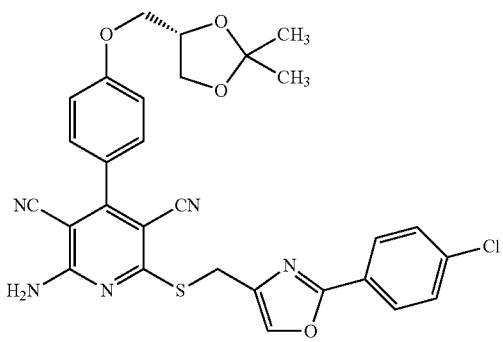 [SMILES: CC1(C)OC[C@H](COc2ccc(-c3c(C#N)c(N)nc(SCc4coc(-c5ccc(Cl)cc5)n4)c3C#N)cc2)O1]

An amount of 150 mg (0.39 mmol) of the compound from example 3A and 98 mg (0.43 mmol) of the compound from example 5A were suspended together with 99 mg (1.18 mmol) of sodium hydrogencarbonate in 2 ml of dry DMF. The reaction mixture was stirred at RT for 20 hours. The batch was thereafter purified directly by means of preparative HPLC (column: YMC GEL ODS-AQ S-5/15 μm; eluent gradient: acetonitrile/water 10:90→95:5).

Yield: 147 mg (65% of theory)

$^1$H-NMR (400 MHz, DMSO-d$_6$): δ=8.37 (s, 1H), 8.29-7.91 (br. s, 2H), 7.97 (d, 2H), 7.61 (d, 2H), 7.47 (d, 2H), 7.12 (d, 2H), 4.48-4.39 (m, 1H), 4.42 (s, 2H), 4.16-4.03 (m, 3H), 3.77 (dd, 1H), 1.37 (s, 3H), 1.31 (s, 3H).

LC-MS (method 3): R$_t$=4.23 min; MS (ESIpos): m/z=574 [M+H]$^+$.

Example 7A

2-Amino-6-({[2-(4-chlorophenyl)-1,3-oxazol-4-yl]methyl}sulfanyl)-4-(4-{[(4R)-2,2-dimethyl-1,3-dioxolan-4-yl]methoxy}phenyl)pyridine-3,5-dicarbonitrile

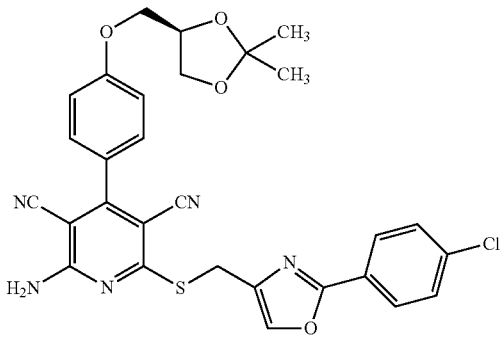 [SMILES: CC1(C)OC[C@@H](COc2ccc(-c3c(C#N)c(N)nc(SCc4coc(-c5ccc(Cl)cc5)n4)c3C#N)cc2)O1]

An amount of 70 mg (0.18 mmol) of the compound from example 4A and 46 mg (0.20 mmol) of the compound from example 5A were suspended together with 46 mg (0.55 mmol) of sodium hydrogencarbonate in 1.9 ml of dry DMF. The reaction mixture was stirred at RT for 20 hours. The batch was subsequently freed from the solvent on a rotary evaporator and the residue was purified by preparative HPLC (column: YMC GEL ODS-AQ S-5/15 μm; eluent gradient: acetonitrile/water 10:90→95:5).

Yield: 79 mg (75% of theory)

$^1$H-NMR (400 MHz, DMSO-d$_6$): δ=8.37 (s, 1H), 8.30-8.01 (br. s, 2H), 7.97 (d, 2H), 7.60 (d, 2H), 7.48 (d, 2H), 7.12 (d, 2H), 4.48-4.40 (m, 1H), 4.42 (s, 2H), 4.16-4.03 (m, 3H), 3.78 (dd, 1H), 1.37 (s, 3H), 1.31 (s, 3H).

LC-MS (method 7): R$_t$=2.99 min; MS (ESIpos): m/z=574 [M+H]$^+$.

Example 8A

2-Amino-6-({[2-(4-chlorophenyl)-1,3-oxazol-4-yl]methyl}sulfanyl)-4-(4-{[(2R)-2,3-dihydroxypropyl]oxy}phenyl)pyridine-3,5-dicarbonitrile

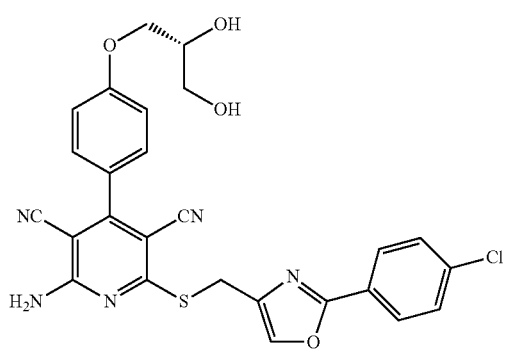 [SMILES: N#Cc1c(N)nc(SCc2coc(-c3ccc(Cl)cc3)n2)c(C#N)c1-c1ccc(OC[C@H](O)CO)cc1]

An amount of 127.1 g (221.4 mmol) of the compound from example 6A were suspended in 800 ml of ethanol and admixed with 800 ml of 37% strength hydrochloric acid. The mixture was stirred under reflux overnight. After cooling to room temperature, the precipitate formed was isolated by suction filtration, washed with ethanol and dried under reduced pressure at 50° C. overnight. This gave 108.3 g (92% of theory) of the target compound.

$^1$H-NMR (400 MHz, DMSO-d$_6$): δ=8.37 (s, 1H), 8.30-7.89 (br. s, 2H), 7.98 (d, 2H), 7.61 (d, 2H), 7.48 (d, 2H), 7.10 (d, 2H), 5.00 (d, 1H), 4.70 (t, 1H), 4.42 (s, 2H), 4.09 (dd, 1H), 3.98-3.92 (m, 1H), 3.81 (q, 1H), 3.50-3.43 (m, 2H).

LC-MS (method 4): R$_t$=2.51 min; MS (ESIpos): m/z=534 [M+H]$^+$.

Example 9A

2-Amino-6-({[2-(4-chlorophenyl)-1,3-oxazol-4-yl]methyl}sulfanyl)-4-(4-{[(2S)-2,3-dihydroxypropyl]oxy}phenyl)pyridine-3,5-dicarbonitrile

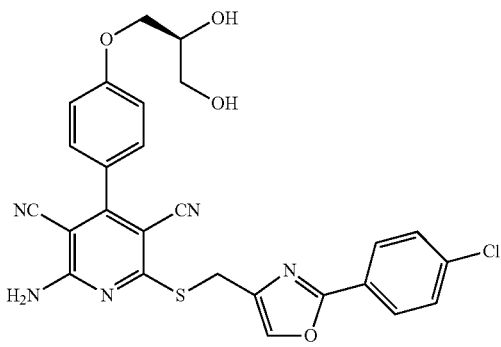 [SMILES: N#Cc1c(N)nc(SCc2coc(-c3ccc(Cl)cc3)n2)c(C#N)c1-c1ccc(OC[C@@H](O)CO)cc1]

An amount of 400 mg (0.70 mmol) of the compound from example 7A was introduced in 17 ml of acetic acid and then admixed cautiously with 8.6 ml of water. The batch was stirred at RT for 12 hours. After the reaction mixture had been concentrated on a rotary evaporator, the residue was purified directly by preparative HPLC (column: YMC GEL ODS-AQ S-5/15 μm; eluent gradient: acetonitrile/water 10:90→95:5). Removal of the solvent on a rotary evaporator gave the product as a white solid.

Yield: 340 mg (91% of theory)

$^1$H-NMR (400 MHz, DMSO-$d_6$): δ=8.37 (s, 1H), 8.27-7.91 (br. s, 2H), 7.98 (d, 2H), 7.60 (d, 2H), 7.47 (d, 2H), 7.10 (d, 2H), 5.00 (d, 1H), 4.70 (t, 1H), 4.42 (s, 2H), 4.09 (dd, 1H), 3.96 (dd, 1H), 3.70 (q, 1H), 3.46 (t, 2H).

LC-MS (method 7): $R_t$=2.48 min; MS (ESIpos): m/z=534 [M+H]$^+$.

Example 10A (2S)-3-{4-[2-Amino-6-({[2-(4-chlorophenyl)-1,3-oxazol-4-yl]methyl}sulfanyl)-3,5-dicyanopyridin-4-yl]phenoxy}propane-1,2-diyl (2S,2'S)-bis{2-[(tert-butoxycarbonyl)amino]propanoate}

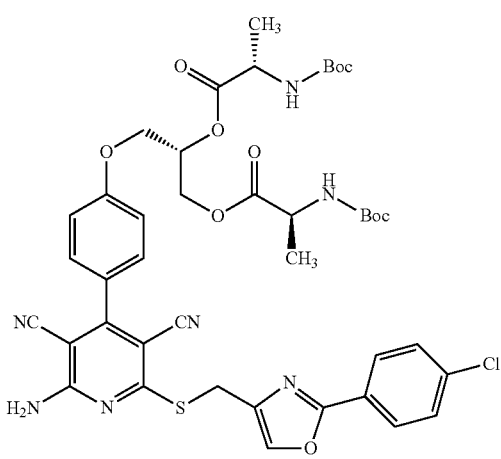 [SMILES: C[C@H](NC(=O)OC(C)(C)C)C(=O)OC[C@H](COc1ccc(-c2c(C#N)c(N)nc(SCc3coc(-c4ccc(Cl)cc4)n3)c2C#N)cc1)OC(=O)[C@H](C)NC(=O)OC(C)(C)C]

An amount of 5 g (9.36 mmol) of the compound from example 8A, 7.09 g (37.45 mmol) of N-Boc-L-alanine, 8.975 g (46.82 mmol) of 1-(3-dimethylaminopropyl)-3-ethylcarbodiimide hydrochloride and 1.144 g (9.36 mmol) of 4-N,N-dimethylaminopyridine were combined in 500 ml of dichloromethane and treated in an ultrasound bath for 30 minutes. The batch was subsequently shaken with 10% strength citric acid solution and thereafter with 10% strength sodium hydrogencarbonate solution until N-Boc-L-alanine was no longer detectable in the organic phase. The organic phase was then dried over magnesium sulfate and concentrated under reduced pressure. The residue was taken up in dichloromethane and admixed with diethyl ether. The precipitate formed was isolated by suction filtration. Drying of the solid left 6.01 g (73% of theory) of the target compound.

$^1$H-NMR (400 MHz, DMSO-$d_6$): δ=8.36 (s, 1H), 8.33-8.02 (br. m, 2H), 7.97 (d, 2H), 7.60 (d, 2H), 7.48 (d, 2H), 7.30 (m, 2H), 7.12 (d, 2H), 5.34 (m, 1H), 4.42 (s, 2H), 4.38-4.21 (m, 4H), 4.03 (m, 2H), 1.36 (s, 18H), 1.26-1.22 (m, 6H).

LC-MS (method 5): $R_t$=1.61 min; MS (ESIpos): m/z=876 [M+H]$^+$.

Example 11A (2S)-3-{4-[2-Amino-6-({[2-(4-chlorophenyl)-1,3-oxazol-4-yl]methyl}sulfanyl)-3,5-dicyanopyridin-4-yl]phenoxy}propane-1,2-diyl (2S,2'S)-bis(2-aminopropanoate)dihydrochloride

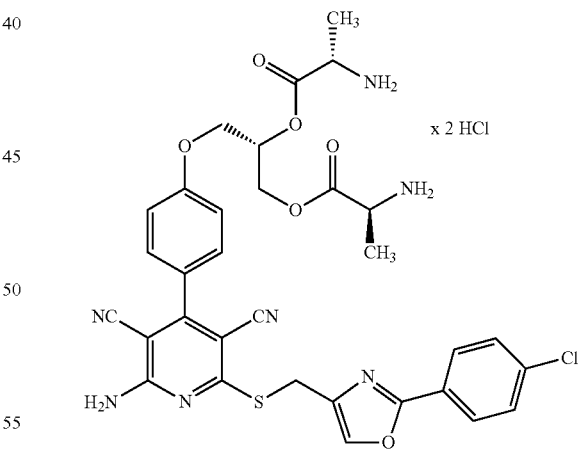

Over 30 minutes, hydrogen chloride gas was introduced into a solution of 6014 mg (6.862 mmol) of the compound from example 10A in 500 ml of dichloromethane, the temperature being held below +20° C. The precipitated solid was isolated by suction filtration, washed with dichloromethane and diethyl ether, and dried under a high vacuum at +80° C. overnight. This gave 5080 mg (99% of theory) of the target compound.

¹H-NMR (400 MHz, DMSO-d₆): δ=8.7 (br. s, 6H), 8.4 (s, 1H), 8.0 (d, 2H), 7.60 (d, 2H), 7.50 (d, 2H), 7.15 (d, 2H), 5.5 (m, 1H), 4.60-4.50 (m, 2H), 4.44 (s, 2H), 4.40 (d, 2H), 4.15 (m, 2H), 1.5-1.4 (m, 6H).

LC-MS (method 7): $R_t$=1.53 min; MS (ESIpos): m/z=676 [M+H]⁺.

Example 12A (2S)-3-{4-[2-Amino-6-({[2-(4-chlorophenyl)-1,3-oxazol-4-yl]methyl}sulfanyl)-3,5-dicyanopyridin-4-yl]phenoxy}propane-1,2-diyl (2S,2'S)-bis(2-aminopropanoate)bis(trifluoroacetic acid) salt

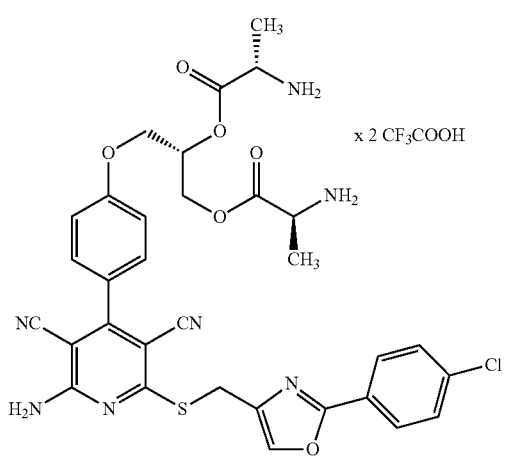 [SMILES: C[C@H](N)C(=O)OC[C@H](COc1ccc(-c2c(C#N)c(N)nc(SCc3coc(-c4ccc(Cl)cc4)n3)c2C#N)cc1)OC(=O)[C@H](C)N]

An amount of 6.520 g (7.440 mmol) of the compound from example 10A was introduced in 45 ml of dichloromethane, admixed with 5.732 ml (74.396 mmol) of trifluoroacetic acid and stirred at room temperature overnight. The reaction mixture was then concentrated and the residue was suspended twice with dichloromethane and concentrated again. The residue was then stirred up with diethyl ether, and the solid which remained was isolated by filtration, washed with diethyl ether and dried under a high vacuum. This gave 4.8 g (69% of theory) of the target compound.

¹H-NMR (400 MHz, DMSO-d₆): δ=8.42 (br. s, 4H), 8.36 (s, 1H), 8.19 (m, 2H), 7.97 (d, 2H), 7.60 (d, 2H), 7.50 (d, 2H), 7.13 (d, 2H), 5.52-5.47 (m, 1H), 4.59-4.50 (m, 2H), 4.41 (s, 2H), 4.39-4.31 (m, 2H), 4.19-4.15 (m, 2H), 1.42-1.34 (m, 6H).

LC-MS (method 5): $R_t$=0.94 min; MS (ESIpos): m/z=676 [M+H]⁺.

Example 13A (6S,9S,12S)-[2-({4-[2-Amino-6-({[2-(4-chlorophenyl)-1,3-oxazol-4-yl]methyl}sulfanyl)-3,5-dicyanopyridin-4-yl]phenoxy}methyl)-2,2,9-trimethyl-6-(2-methylpropyl)-4,7,10-trioxo-3,11-dioxa-5,8-diazamidecan-13-yl (2S)-2-({(2S)-2-[(tert-butoxycarbonyl)amino]-4-methylpentanoyl}amino)propanoate

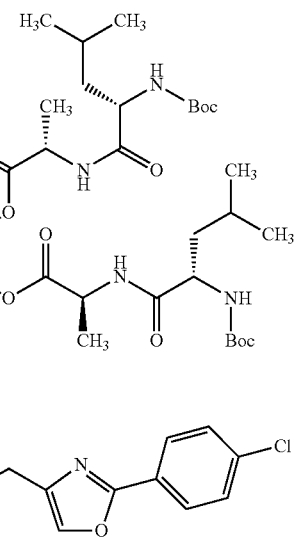

An amount of 139 mg (0.60 mmol) of N-(tert-butoxycarbonyl)-L-leucine was stirred together with 81 mg (0.60 mmol) of 1-hydroxy-1H-benzotriazole hydrate and 80 mg (0.421 mmol) of 1-(3-dimethylaminopropyl)-3-ethylcarbodiimide hydrochloride in 3 ml of DMF for 5 minutes. Then 150 mg (0.20 mmol) of the compound from example 11A and also 0.174 ml (1.00 mmol) of N,N-diisopropylethylamine were added and the reaction mixture was stirred at RT overnight. Thereafter, again, the same amounts of N-(tert-butoxycarbonyl)-L-leucine, 1-hydroxy-1H-benzotriazole hydrate, 1-(3-dimethylaminopropyl)-3-ethylcarbodiimide hydrochloride and N,N-diisopropylethylamine were added, and the mixture was stirred at RT for a further 3 hours. The reaction batch was then purified directly by preparative HPLC (eluent gradient: acetonitrile/water 10:90→95:5). This gave 188 mg (85% of theory) of the target compound.

¹H-NMR (400 MHz, DMSO-d₆): δ=8.36 (s, 1H), 8.24 (d, 2H), 7.99 (d, 2H), 7.60 (d, 2H), 7.48 (d, 2H), 7.12 (d, 2H), 6.80 (t, 2H), 5.33-5.29 (m, 1H), 4.41 (s, 2H), 4.37-4.19 (m, 6H), 4.03-3.97 (m, 2H), 1.64-1.56 (m, 2H), 1.44-1.38 (m, 4H), 1.36 (2s, 18H), 1.30-1.27 (m, 6H), 0.86-0.83 (m, 12H).

LC-MS (method 6): $R_t$=2.88 min; MS (ESIpos): m/z=1102 [M+H]⁺.

Example 14A (6S,9S,13S)-14-{4-[2-Amino-6-({[2-(4-chlorophenyl)-1,3-oxazol-4-yl]methyl}sulfanyl)-3,5-dicyanopyridin-4-yl]phenoxy}-6-[(2S)-butan-2-yl]-2,2,9-trimethyl-4,7,10-trioxo-3,11-dioxa-5,8-diazatetradecan-13-yl (2S)-2-({(2S,3S)-2-[(tert-butoxycarbonyl)amino]-3-methylpentanoyl}amino)propanoate

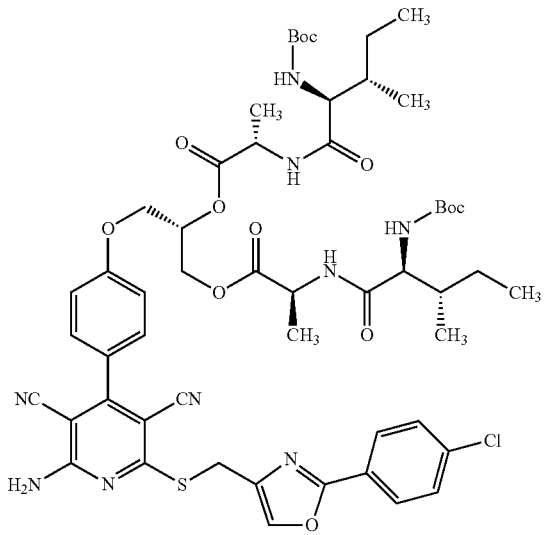 [SMILES: CC[C@H](C)[C@H](NC(=O)OC(C)(C)C)C(=O)N[C@@H](C)C(=O)OC[C@H](COc1ccc(-c2c(C#N)c(N)nc(SCc3coc(-c4ccc(Cl)cc4)n3)c2C#N)cc1)OC(=O)[C@H](C)NC(=O)[C@@H](NC(=O)OC(C)(C)C)[C@@H](C)CC]

The title compound was prepared in the same way as for the preparation of example 13A, starting from the compound from example 11A and N-(tert-butoxycarbonyl)-L-isoleucine.

Yield: 82% of theory $^1$H-NMR (400 MHz, DMSO-$d_6$): δ=8.36 (s, 1H), 8.32-8.31 (m, 2H), 7.97 (d, 2H), 7.61 (d, 2H), 7.48 (d, 2H), 7.11 (d, 2H), 6.65-6.61 (m, 2H), 5.42-5.31 (m, 1H), 4.42 (s, 2H), 4.39-4.19 (m, 6H), 3.85 (m, 2H), 1.67-1.65 (m, 2H), 1.52-1.40 (m, 2H), 1.35 (2s, 18H), 1.29 (t, 6H), 1.12-1.01 (m, 2H), 0.84-0.77 (m, 12H).

LC-MS (method 6): $R_t$=2.87 min; MS (ESIpos): m/z=1102 [M+H]$^+$.

Example 15A (8S,11S,15S)-16-{4-[2-Amino-6-({[2-(4-chlorophenyl)-1,3-oxazol-4-yl]methyl}sulfanyl)-3,5-dicyanopyridin-4-yl]phenoxy}-8-[(tert-butoxycarbonyl)amino]-2,2,11-trimethyl-4,9,12-trioxo-3,13-dioxa-5,10-diazahexadecan-15-yl (2S)-2-({(2S)-2,4-bis[(tert-butoxycarbonyl)amino]butanoyl}amino)propanoate An amount of 250 mg (0.501 mmol) of (2S)-2,4-bis[(tert-butoxycarbonyl)amino]butanoic acid dicyclohexylamine salt was stirred together with 68 mg (0.501 mmol) of 1-hydroxy-1H-benzotriazole hydrate and 67 mg. (0.350 mmol) of 1-(3-dimethylaminopropyl)-3-ethylcarbodiimide hydrochloride in 3 ml of DMF for 5 minutes. Then 125 mg (0.200 mmol) of the compound from example 11A and also 0.145 ml (0.834 mmol) of N,N-diisopropylethylamine were added and the mixture was stirred at RT overnight. The reaction batch was then purified directly by preparative HPLC (eluent gradient: acetonitrile/water 10:90→95:5). This gave 166 mg (76% of theory) of the target compound.

$^1$H-NMR (400 MHz, DMSO-$d_s$): δ=8.36 (s, 1H), 8.25 (m, 2H), 8.12-8.00 (m, 2H), 7.97 (d, 2H), 7.60 (d, 2H), 7.47 (d, 2H), 7.11 (s, 2H), 6.88-6.84 (m, 2H), 6.75-6.64 (m, 2H), 5.37-5.28 (m, 1H), 4.42 (s, 2H), 4.38-4.19 (m, 6H), 3.98-3.93 (m, 2H), 3.06-2.91 (m, 4H), 1.77-1.71 (m, 2H), 1.61-1.51 (m, 2H), 1.35 (s, 36H), 1.31-1.27 (m, 6H).

LC-MS (method 7): $R_t$=3.17 min; MS (ESIpos): m/z=1276 [M+H]$^+$.

Example 16A (9S,12S,16S)-17-{4-[2-Amino-6-({[2-(4-chlorophenyl)-1,3-oxazol-4-yl]methyl}sulfanyl)-3,5-dicyanopyridin-4-yl]phenoxy}-9-[(tert-butoxycarbonyl)amino]-2,2,12-trimethyl-4,10,13-trioxo-3,14-dioxa-5,11-diazaheptadecan-16-yl (2S)-2-({(2S)-2,5-bis[(tert-butoxycarbonyl)amino]pentanoyl}amino)propanoate

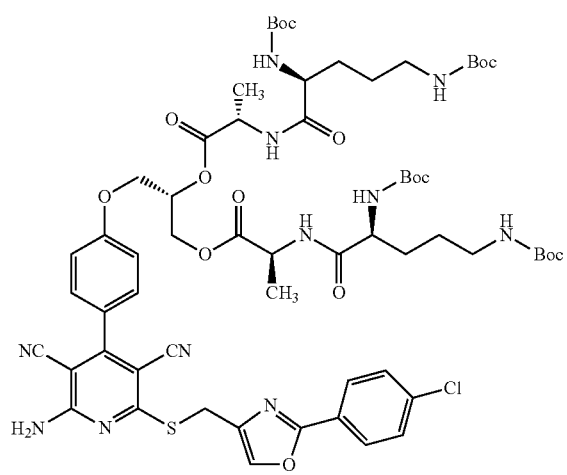 [SMILES: C[C@H](NC(=O)[C@H](CCCNC(=O)OC(C)(C)C)NC(=O)OC(C)(C)C)C(=O)OC[C@H](COc1ccc(-c2c(C#N)c(N)nc(SCc3coc(-c4ccc(Cl)cc4)n3)c2C#N)cc1)OC(=O)[C@H](C)NC(=O)[C@H](CCCNC(=O)OC(C)(C)C)NC(=O)OC(C)(C)C]

The title compound was prepared in the same way as for the preparation of example 15A, starting from the compound from example 11A and commercial $N^2,N^5$-bis(tert-butoxycarbonyl)-L-ornithine.

Yield: 86% of theory $^1$H-NMR (400 MHz, DMSO-$d_6$): δ=8.36 (s, 1H), 8.21 (br. d, 2H), 8.15-8.01 (m, 2H), 7.97 (d, 2H), 7.60 (d, 2H), 7.48 (d, 2H), 7.12 (d, 2H), 6.82-6.71 (m, 4H), 5.37-5.28 (m, 1H), 4.42 (s, 2H), 4.38-4.19 (m, 6H), 3.96-3.86 (m, 2H), 2.94-2.81 (m, 4H), 1.47-1.23 (m, 50H).

LC-MS (method 7): $R_t$=3.17 min; MS (ESIpos): m/z=1304 [M+H]$^+$.

Example 17A (6S,9S,13S)-14-{4-[2-Amino-6-({[2-(4-chlorophenyl)-1,3-oxazol-4-yl]methyl}sulfanyl)-3,5-dicyanopyridin-4-yl]phenoxy}-6-(tert-butoxymethyl)-2,2,9-trimethyl-4,7,10-trioxo-3,11-dioxa-5,8-diazatetradecan-13-yl (2S)-2-({(2S)-3-tert-butoxy-2-[(tert-butoxycarbonyl)amino]propanoyl}amino)propanoate

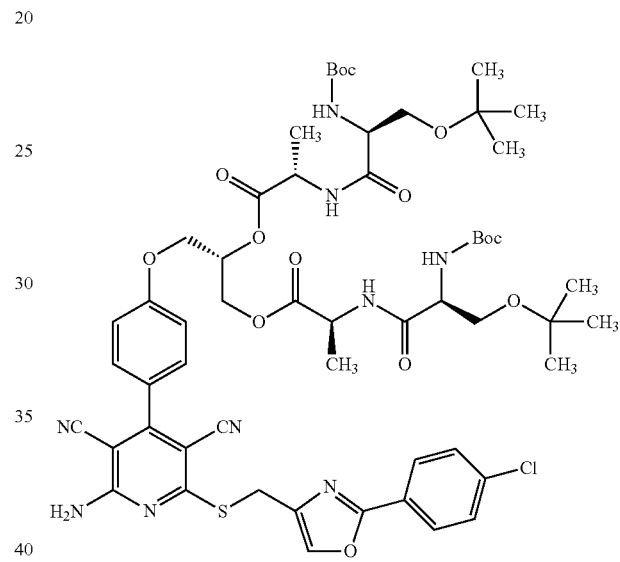

The title compound was prepared in the same way as for the preparation of example 15A, starting from the compound from example 11A and commercial N-(tert-butoxycarbonyl)-O-tert-butyl-L-serine dicyclohexylamine salt.

Yield: 80% of theory $^1$H-NMR (400 MHz, DMSO-$d_6$): δ=8.66 (s, 1H), 8.28-8.21 (m, 2H), 8.18-8.02 (m, 2H), 7.97 (d, 2H), 7.60 (d, 2H), 7.48 (d, 2H), 7.12-7.10 (d, 2H), 6.64-6.58 (m, 2H), 5.37-5.30 (m, 1H), 4.42 (s, 2H), 4.39-4.18 (m, 6H), 4.08-4.01 (m, 2H), 3.49-3.35 (m, 4H), 1.36 (2s, 18H), 1.29 (t, 6H), 1.09 (2s, 18H).

LC-MS (method 7): $R_t$=3.27 min; MS (ESIpos): m/z=1162 [M+H]$^+$.

Example 18A (6S,9S,13S)-14-{4-[2-Amino-6-({[2-(4-chlorophenyl)-1,3-oxazol-4-yl]methyl}sulfanyl)-3,5-dicyanopyridin-4-yl]phenoxy}-6-benzyl-2,2,9-trimethyl-4,7,10-trioxo-3,11-dioxa-5,8-diazatetradecan-13-yl (2S)-2-({(2S)-2-[(tert-butoxycarbonyl)amino]-3-phenylpropanoyl}amino)propanoate

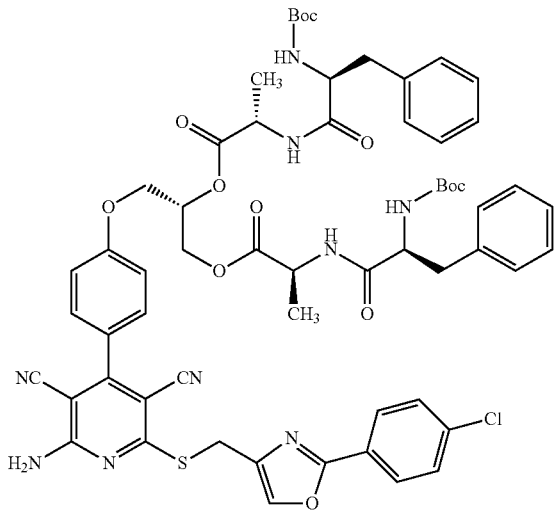 [SMILES: C[C@H](NC(=O)[C@H](Cc1ccccc1)NC(=O)OC(C)(C)C)C(=O)OC[C@H](COc1ccc(-c2c(C#N)c(N)nc(SCc3coc(-c4ccc(Cl)cc4)n3)c2C#N)cc1)OC(=O)[C@H](C)NC(=O)[C@H](Cc1ccccc1)NC(=O)OC(C)(C)C]

The title compound was prepared in the same way as for the preparation of example 15A, starting from the compound from example 11A and commercial N-(tert-butoxycarbonyl)-L-phenylalanine.

Yield: 83% of theory $^1$H-NMR (400 MHz, DMSO-$d_6$): δ=8.47-8.40 (m, 2H), 8.37 (s, 1H), 8.31-8.01 (m, 2H), 7.97 (d, 2H), 7.60 (d, 2H), 7.44 (d, 2H), 7.33-7.21 (m, 8H), 7.20-7.13 (m, 2H), 7.09 (d, 2H), 6.91-6.87 (m, 2H), 5.39-5.32 (m, 1H), 4.42 (s, 2H), 4.40-4.07 (m, 8H), 3.02-2.90 (m, 2H), 2.74-2.61 (m, 2H), 1.34-1.31 (m, 6H), 1.26 (2s, 14H), 1.22-1.18 (m, 4H).

LC-MS (method 7): $R_t$=3.22 min; MS (ESIpos): m/z=1170 [M+H]$^+$.

Example 19A (9S,12S)-12-({4-[2-Amino-6-({[2-(4-chlorophenyl)-1,3-oxazol-4-yl]methyl}sulfanyl)-3,5-dicyanopyridin-4-yl]phenoxy}methyl)-2,2,9-trimethyl-4,7,10-trioxo-3,11-dioxa-5,8-diazamidecan-13-yl (2S)-2-({[(tert-butoxycarbonyl)amino]acetyl}amino)propanoate

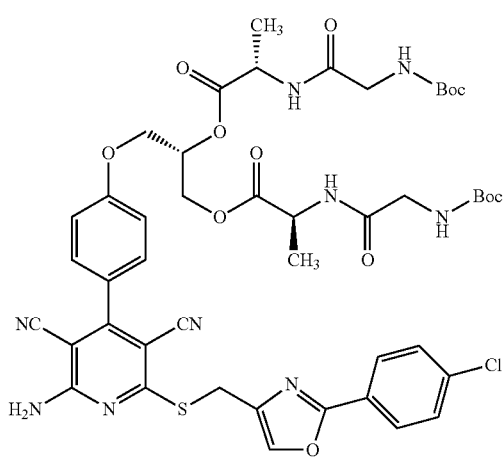 [SMILES: C[C@H](NC(=O)CNC(=O)OC(C)(C)C)C(=O)OC[C@H](COc1ccc(-c2c(C#N)c(N)nc(SCc3coc(-c4ccc(Cl)cc4)n3)c2C#N)cc1)OC(=O)[C@H](C)NC(=O)CNC(=O)OC(C)(C)C]

An amount of 1.535 g (8.765 mmol) of N-(tert-butoxycarbonyl)glycine was stirred together with 711 mg (5.259 mmol) of 1-hydroxy-1H-benzotriazole hydrate and 807 mg (4.207 mmol) of 1-(3-dimethylaminopropyl)-3-ethylcarbodiimide hydrochloride in 50 ml of DMF for 5 minutes. Then 3.17 g (3.506 mmol) of the compound from example 12A and also 2.44 ml (14.023 mmol) of N,N-diisopropylethylamine were added and the mixture was stirred at RT overnight. Thereafter a further 768 mg (4.382 mmol) of N-(tert-butoxycarbonyl)glycine, 1.221 ml (7.012 mmol) of N,N-diisopropylethylamine, 404 mg (2.104 mmol) of 1-(3-dimethylaminopropyl)-3-ethylcarbodiimide hydrochloride and 356 mg (2.630 mmol) of 1-hydroxy-1H-benzotriazole hydrate were added and the reaction mixture was stirred again at RT for 4 hours. The batch was thereafter purified directly by preparative HPLC (eluent gradient: acetonitrile/water 10:90→95:5). This gave 2.37 g (66% of theory) of the target compound.

$^1$H-NMR (400 MHz, DMSO-$d_6$): δ=8.36 (s, 1H), 8.22 (d, 2H), 8.17-8.01 (m, 2H), 7.97 (d, 2H), 7.60 (d, 2H), 7.48 (d, 2H), 7.13 (d, 2H), 6.93-6.87 (m, 2H), 5.37-5.30 (m, 1H), 4.42 (s, 2H), 4.36-4.21 (m, 6H), 3.64-3.45 (m, 4H), 1.36 (s, 18H), 1.28 (t, 6H).

LC-MS (method 6): $R_t$=2.42 min; MS (ESIpos): m/z=990 [M+H]$^+$.

Example 20A

Di-tert-butyl (2S,2'S)-2,2'-([(2S)-3-{4-[2-amino-6-({[2-(4-chlorophenyl)-1,3-oxazol-4-yl]methyl}sulfanyl)-3,5-dicyanopyridin-4-yl]phenoxy}propane-1,2-diyl]bis{oxy[(2S)-1-oxopropane-1,2-diyl]carbamoyl})dipyrrolidine-1-carboxylate

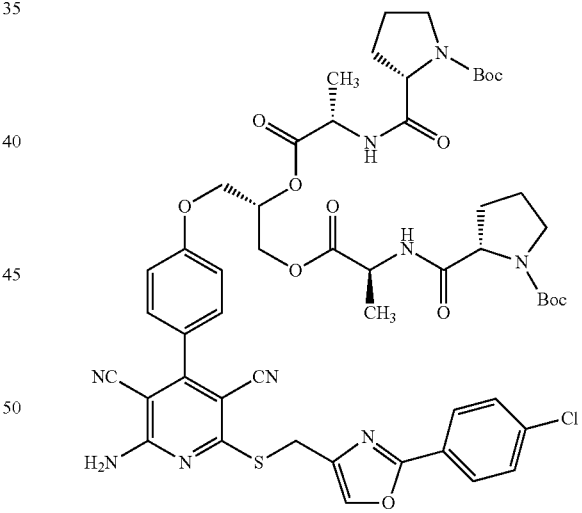

The title compound was prepared in the same way as for the preparation of example 19A, starting from the compound from example 11A and commercial 1-(tert-butoxycarbonyl)-L-proline.

Yield: 84% of theory $^1$H-NMR (400 MHz, DMSO-$d_6$): δ=8.36 (s, 1H), 8.34-8.26 (m, 2H), 8.19-8.02 (m, 2H), 7.97 (d, 2H), 7.61 (d, 2H), 7.48 (d, 2H), 7.11 (d, 2H), 5.41-5.31 (m, 1H), 4.42 (s, 2H), 4.39-4.18 (m, 6H), 4.14-4.02 (m, 2H), 3.27-3.19 (m, 2H), 2.12-1.96 (m, 2H), 1.86-1.64 (m, 6H), 1.40-1.28 (m, 24H).

LC-MS (method 7): $R_t$=2.98 min; MS (ESIpos): m/z=1070 [M+H]$^+$.

Example 21A (9S,12S)-12-({4-[2-Amino-6-({[2-(4-chlorophenyl)-1,3-oxazol-4-yl]methyl}sulfanyl)-3,5-dicyanopyridin-4-yl]phenoxy}methyl)-2,2,5,9-tetramethyl-4,7,10-trioxo-3,11-dioxa-5,8-diazamidecan-13-yl (2S)-2-({[(tert-butoxycarbonyl)(methyl)amino]acetyl}amino)propanoate

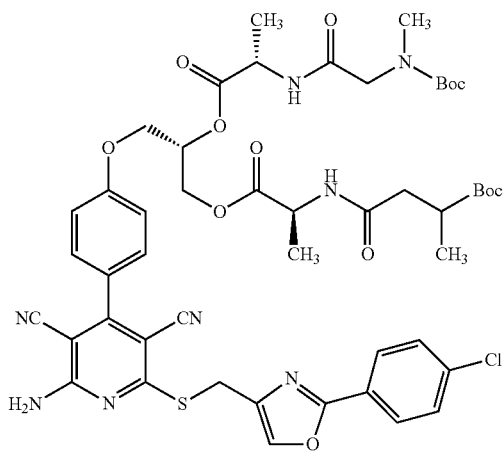 [SMILES: CC(CC(=O)N[C@@H](C)C(=O)OC[C@H](COc1ccc(-c2c(C#N)c(N)nc(SCc3coc(-c4ccc(Cl)cc4)n3)c2C#N)cc1)OC(=O)[C@H](C)NC(=O)CN(C)C(=O)OC(C)(C)C)C(=O)OC(C)(C)C]

The title compound was prepared in the same way as for the preparation of example 19A, starting from the compound from example 12A and commercial N-(tert-butoxycarbonyl)-N-methylglycine.

Yield: 60% of theory $^1$H-NMR (400 MHz, DMSO-$d_6$): δ=8.36 (s, 1H), 8.34-8.29 (m, 2H), 8.21-8.02 (m, 2H), 7.97 (d, 2H), 7.60 (d, 2H), 7.49 (d, 2H), 7.12 (d, 2H), 5.39-5.31 (m, 1H), 4.42 (s, 2H), 4.38-4.19 (m, 6H), 3.91-3.68 (m, 4H), 2.77 (s, 3H), 2.75 (s, 3H), 1.37-1.23 (m, 24H).

LC-MS (method 5): $R_t$=1.52 min; MS (ESIpos): m/z=1018 [M+H]$^+$.

Example 22A

Di-tert-butyl (2S,6S,9S,13S,17S)-9-({4-[2-amino-6-({[2-(4-chlorophenyl)-1,3-oxazol-4-yl]methyl}sulfanyl)-3,5-dicyanopyridin-4-yl]phenoxy}methyl)-2,17-bis[(tert-butoxycarbonyl)amino]-6,13-dimethyl-4,7,12,15-tetraoxo-8,11-dioxa-5,14-diazaoctadecane-1,18-dioate

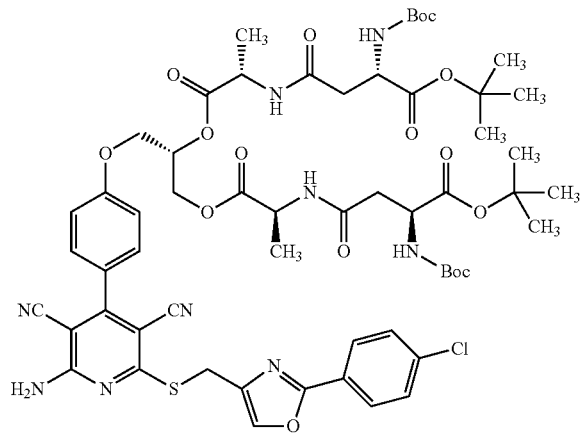 [SMILES: C[C@H](NC(=O)C[C@H](NC(=O)OC(C)(C)C)C(=O)OC(C)(C)C)C(=O)OC[C@H](COc1ccc(-c2c(C#N)c(N)nc(SCc3coc(-c4ccc(Cl)cc4)n3)c2C#N)cc1)OC(=O)[C@H](C)NC(=O)C[C@H](NC(=O)OC(C)(C)C)C(=O)OC(C)(C)C]

The title compound was prepared in the same way as for the preparation of example 19A, starting from the compound from example 12A and commercial (3S)-4-tert-butoxy-3-[(tert-butoxycarbonyl)amino]-4-oxobutanoic acid.

Yield: 71% of theory $^1$H-NMR (400 MHz, DMSO-$d_6$): δ=8.36 (s, 1H), 8.35 (d, 2H), 8.29-8.02 (m, 2H), 7.97 (d, 2H), 7.60 (d, 2H), 7.48 (d, 2H), 7.13 (d, 2H), 6.91-6.87 (m, 2H), 5.38-5.30 (m, 1H), 4.41 (s, 2H), 4.39-4.07 (m, 8H), 2.52-2.41 (m, 4H), 1.36 (s, 36H), 1.29-1.23 (m, 6H).

LC-MS (method 5): $R_t$=1.69 min; MS (ESIpos): m/z=1218 [M+H]$^+$.

Example 23A (6S,9S,13S)-14-{4-[2-Amino-6-({[2-(4-chlorophenyl)-1,3-oxazol-4-yl]methyl}sulfanyl)-3,5-dicyanopyridin-4-yl]phenoxy}-6-(2-amino-2-oxoethyl)-2,2,9-trimethyl-4,7,10-trioxo-3,11-dioxa-5,8-diazatetradecan-13-yl (2S)-2-({(2S)-4-amino-2-[(tert-butoxycarbonyl)amino]-4-oxobutanoyl}amino)propanoate An amount of 115 mg (0.498 mmol) of N$^2$-(tert-butoxycarbonyl)-L-asparagine was stirred together with 40 mg (0.299 mmol) of 1-hydroxy-1H-benzotriazole hydrate and 46 mg (0.239 mmol) of 1-(3-dimethylaminopropyl)-3-ethylcarbodiimide hydrochloride in 3 ml of DMF for 5 minutes. Then 240 mg (0.199 mmol) of the compound from example 12A and 0.139 ml (0.796 mmol) of N,N-diisopropylethylamine were added and the mixture was stirred at RT overnight. The reaction batch was subsequently purified directly by means of preparative HPLC (eluent gradient: acetonitrile/water 10:90→95:5). This gave 66 mg (22% of theory) of the target compound.

$^1$H-NMR (400 MHz, DMSO-$d_6$): δ=8.36 (s, 1H), 8.32-8.16 (m, 4H), 7.97 (d, 2H), 7.60 (d, 2H), 7.48 (d, 2H), 7.25-7.17 (m, 2H), 7.13 (d, 2H), 6.95-6.82 (m, 4H), 5.36-5.29 (m, 1H), 4.42 (s, 2H), 4.38-4.16 (m, 8H), 2.47-2.31 (m, 4H), 1.35 (2s, 18H), 1.28 (t, 6H).

LC-MS (method 6): $R_t$=2.15 min; MS (ESIpos): m/z=1104 [M+H]$^+$.

Example 24A

Di-tert-butyl (3S,6S,9S,13S,16S)-9-({4-[2-amino-6-({[2-(4-chlorophenyl)-1,3-oxazol-4-yl]methyl}sulfanyl)-3,5-dicyanopyridin-4-yl]phenoxy}methyl)-3,16-bis[(tert-butoxycarbonyl)amino]-6,13-dimethyl-4,7,12,15-tetraoxo-8,11-dioxa-5,14-diazaoctadecane-1,18-dioate

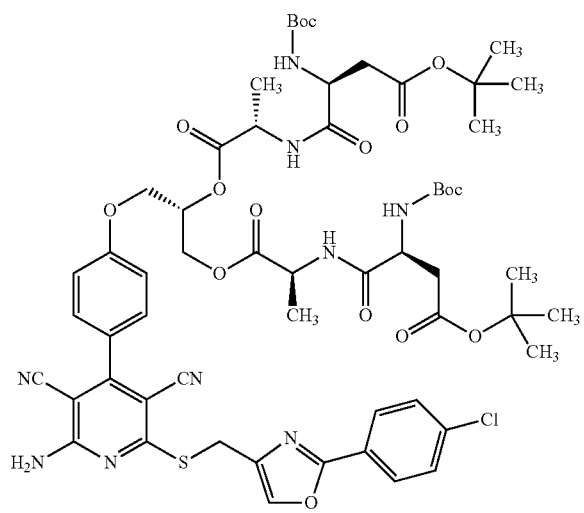 [SMILES: C[C@H](NC(=O)[C@H](CC(=O)OC(C)(C)C)NC(=O)OC(C)(C)C)C(=O)OC[C@H](COc1ccc(-c2c(C#N)c(N)nc(SCc3coc(-c4ccc(Cl)cc4)n3)c2C#N)cc1)OC(=O)[C@H](C)NC(=O)[C@H](CC(=O)OC(C)(C)C)NC(=O)OC(C)(C)C]

An amount of 320 mg (1.106 mmol) of (2S)-4-tert-butoxy-2-[(tert-butoxycarbonyl)amino]-4-oxobutanoic acid was stirred together with 90 mg (0.664 mmol) of 1-hydroxy-1H-benzotriazole hydrate and 102 mg (0.531 mmol) of 1-(3-dimethylaminopropyl)-3-ethylcarbodiimide hydrochloride in 3 ml of DMF for 5 minutes. Then 400 mg (0.442 mmol) of the compound from example 12A and 0.308 ml (1.770 mmol) of N,N-diisopropylethylamine were added and the mixture was stirred at RT overnight. Thereafter, again, the same amounts of (2S)-4-tert-butoxy-2-[(tert-butoxycarbonyl)amino]-4-oxobutanoic acid, 1-hydroxy-1H-benzotriazole hydrate, 1-(3-dimethylaminopropyl)-3-ethylcarbodiimide hydrochloride and N,N-diisopropylethylamine were added and the reaction mixture was stirred at RT for 3 hours more. The batch was subsequently purified directly by means of preparative HPLC (eluent gradient: acetonitrile/water 10:90→95:5). This gave 418 mg (77% of theory) of the target compound.

$^1$H-NMR (400 MHz, DMSO-d$_6$): δ=8.37 (s, 1H), 8.28-8.24 (m, 2H), 8.20-8.00 (m, 2H), 7.97 (d, 2H), 7.60 (d, 2H), 7.48 (d, 2H), 7.13 (d, 2H), 7.00 (br. d, 2H), 5.34-5.30 (m, 1H), 4.42 (s, 2H), 4.38-4.19 (m, 8H), 2.65-2.57 (m, 2H), 2.44-2.37 (m, 2H), 1.39-1.35 (m, 36H), 1.31-1.26 (m, 6H).

LC-MS (method 5): $R_t$=1.72 min; MS (ESIpos): m/z=1218 [M+H]$^+$.

Example 25A

Di-tert-butyl (4S,7S,10S,14S,17S)-10-({4-[2-amino-6-({[2-(4-chlorophenyl)-1,3-oxazol-4-yl]methyl}sulfanyl)-3,5-dicyanopyridin-4-yl]phenoxy}methyl)-4,17-bis[(tert-butoxycarbonyl)amino]-7,14-dimethyl-5,8,13,16-tetraoxo-9,12-dioxa-6,15-diazaicosane-1,20-dioate

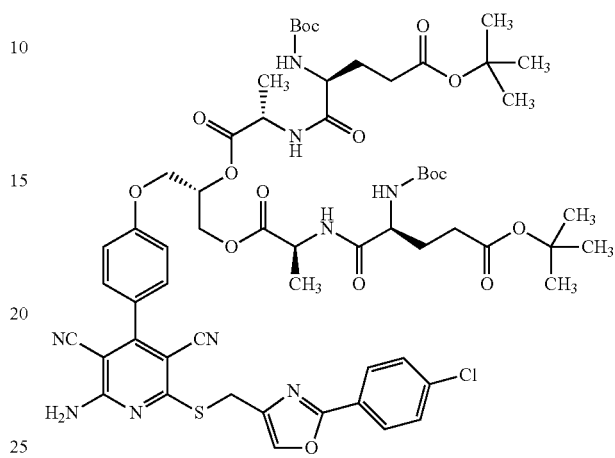

The title compound was prepared in the same way as for the preparation of example 24A, starting from the compound from example 12A and commercial (2S)-5-tert-butoxy-2-[(tert-butoxycarbonyl)amino]-5-oxopentanoic acid.

Yield: 67% of theory $^1$H-NMR (400 MHz, DMSO-d$_6$): δ=8.37 (s, 1H), 8.30-8.27 (m, 2H), 8.20-8.01 (m, 2H), 7.97 (d, 2H), 7.60 (d, 2H), 7.48 (d, 2H), 7.12 (d, 2H), 6.83 (br. t, 2H), 5.38-5.30 (m, 1H), 4.42 (s, 2H), 4.40-4.21 (m, 6H), 4.00-3.94 (m, 2H), 2.32-2.16 (m, 4H), 1.92-1.79 (m, 2H), 1.74-1.64 (m, 2H), 1.37-1.35 (m, 36H), 1.31-1.28 (m, 6H).

LC-MS (method 6): $R_t$=2.95 min; MS (ESIpos): m/z=1246 [M+H]$^+$.

Example 26A (6S,9S,13S)-14-{4-[2-Amino-6-({[2-(4-chlorophenyl)-1,3-oxazol-4-yl]methyl}sulfanyl)-3,5-dicyanopyridin-4-yl]phenoxy}-6-(1H-imidazol-4-ylmethyl)-2,2,9-trimethyl-4,7,10-trioxo-3,11-dioxa-5,8-diazatetradecan-13-yl (2S)-2-{[(2S)-2-[(tert-butoxycarbonyl)amino]-3-(1H-imidazol-4-yl)propanoyl]amino}propanoate

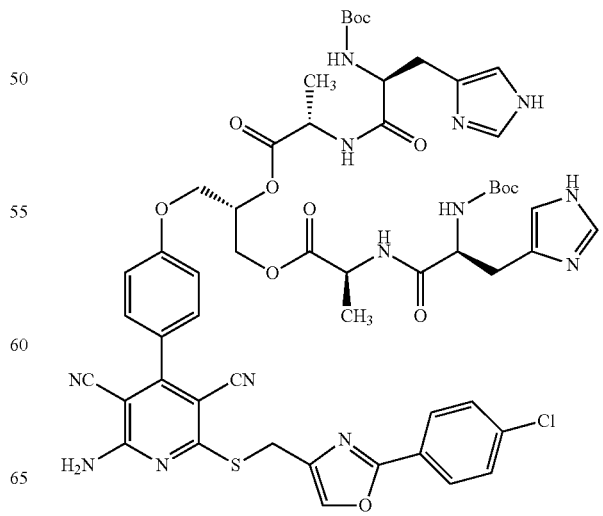

The title compound was prepared in the same way as for the preparation of example 24A, starting from the compound from example 12A and commercial N-(tert-butoxycarbonyl)-L-histidine.

Yield: 52% of theory $^1$H-NMR (400 MHz, DMSO-d$_6$): δ=8.63-8.42 (m, 2H), 8.37 (s, 1H), 7.97 (d, 2H), 7.60 (d, 2H), 7.52 (br. s, 2H), 7.46 (d, 2H), 7.10 (d, 2H), 6.93-6.71 (m, 4H), 4.42 (s, 2H), 5.41-5.26 (m, 1H), 4.41 (s, 2H), 4.38-4.00 (m, 8H), 2.97-2.67 (m, 4H), 1.37-1.20 (m, 24H).

LC-MS (method 6): R$_t$=1.40 min; MS (ESIpos): m/z=1150 [M+H]$^+$.

Example 27A

Di-tert-butyl (2S,7S,10S,14S,19S)-10-({4-[2-amino-6-({[2-(4-chlorophenyl)-1,3-oxazol-4-yl]methyl}sulfanyl)-3,5-dicyanopyridin-4-yl]phenoxy}methyl)-2,19-bis[(tert-butoxycarbonyl)amino]-7,14-dimethyl-5,8,13,16-tetraoxo-9,12-dioxa-6,15-diazaicosane-1,20-dioate

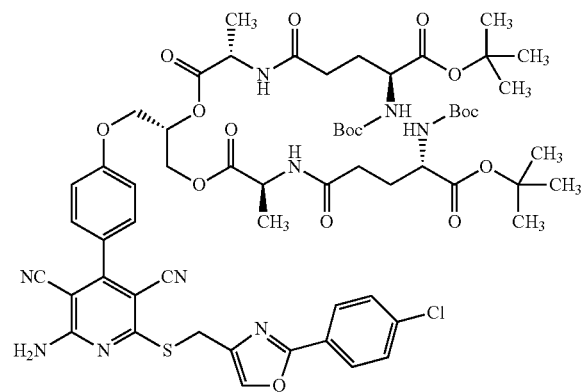 [SMILES: C[C@H](NC(=O)CC[C@H](NC(=O)OC(C)(C)C)C(=O)OC(C)(C)C)C(=O)OC[C@H](COc1ccc(-c2c(C#N)c(N)nc(SCc3coc(-c4ccc(Cl)cc4)n3)c2C#N)cc1)OC(=O)[C@H](C)NC(=O)CC[C@H](NC(=O)OC(C)(C)C)C(=O)OC(C)(C)C]

The title compound was prepared in the same way as for the preparation of example 24A, starting from the compound from example 11A and commercial (4S)-5-tert-butoxy-4-[(tert-butoxycarbonyl)amino]-5-oxopentanoic acid.

Yield: 73% of theory $^1$H-NMR (400 MHz, DMSO-d$_6$): δ=8.36 (s, 1H), 8.25 (d, 2H), 8.20-8.01 (m, 2H), 7.97 (d, 2H), 7.60 (d, 2H), 7.48 (d, 2H), 7.14-7.09 (m, 4H), 5.35-5.30 (m, 1H), 4.42 (s, 2H), 4.34 (d, 2H), 4.29-4.20 (m, 4H), 3.80-3.67 (m, 2H), 2.22-2.15 (m, 4H), 1.94-1.82 (m, 2H), 1.76-1.59 (m, 2H), 1.41-1.32 (m, 36H), 1.28-1.22 (m, 6H).

LC-MS (method 5): R$_t$=1.69 min; MS (ESIpos): m/z=1246 [M+H]$^+$.

Example 28A (2S)-3-{4-[2-Amino-6-({[2-(4-chlorophenyl)-1,3-oxazol-4-yl]methyl}sulfanyl)-3,5-dicyanopyridin-4-yl]phenoxy}propane-1,2-diyl bis{3-[(tert-butoxycarbonyl)amino]propanoate}

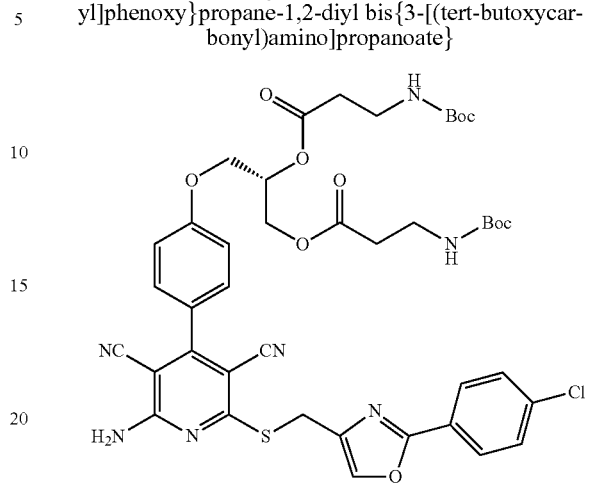

An amount of 200 mg (0.375 mmol) of the compound from example 8A was introduced in 10 ml of dichloromethane/DMF (1:1), admixed with 213 mg (1.124 mmol) of N-(tert-butoxycarbonyl)-β-alanine, 215 mg (1.124 mmol) of 1-(3-dimethylaminopropyl)-3-ethylcarbodiimide hydrochloride and 4.6 mg (0.037 mmol) of 4-N,N-dimethylaminopyridine and stirred at room temperature overnight. The reaction mixture was subsequently purified directly by means of preparative HPLC (acetonitrile/water gradient 10:90→95:5). This gave 126 mg (38% of theory) of the target compound.

LC-MS (method 6): R$_t$=2.67 min; MS (ESIpos): m/z=876 [M+H]$^+$.

Example 29A (2S)-3-{4-[2-Amino-6-({[2-(4-chlorophenyl)-1,3-oxazol-4-yl]methyl}sulfanyl)-3,5-dicyanopyridin-4-yl]phenoxy}propane-1,2-diyl bis(3-aminopropanoate)dihydrochloride

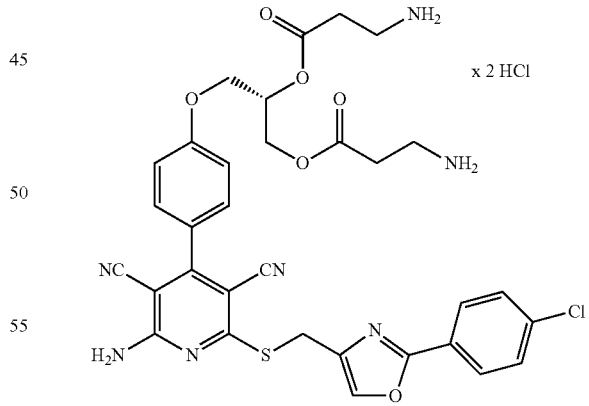

An amount of 123 mg (0.140 mmol) of the compound from example 28A was introduced in 2 ml of dichloromethane and admixed with 1.4 ml (2.807 mmol) of a 2M solution of hydrogen chloride gas in diethyl ether. After 1 hour of stirring, the precipitated solid was isolated by filtration, washed with dichloromethane and diethyl ether and dried under reduced pressure. This gave 79 mg (75% of theory) of the target compound.

¹H-NMR (400 MHz, DMSO-d₆): δ=8.38 (s, 1H), 8.34-8.12 (br. s, 2H), 8.03 (br. m, 6H), 7.97 (d, 2H), 7.61 (d, 2H), 7.49 (d, 2H), 7.14 (d, 2H), 5.40 (m, 1H), 4.42 (s, 2H), 4.41-4.29 (m, 4H), 3.04 (br. m, 4H), 2.75 (br. m, 4H).

LC-MS (method 6): $R_t$=1.17 min; MS (ESIpos): m/z=676 [M+H]⁺.

Example 30A (2S)-3-{4-[2-Amino-6-({[2-(4-chlorophenyl)-1,3-oxazol-4-yl]methyl}sulfanyl)-3,5-dicyanopyridin-4-yl]phenoxy}propane-1,2-diyl bis(3-aminopropanoate)bis(trifluoroacetic acid)salt

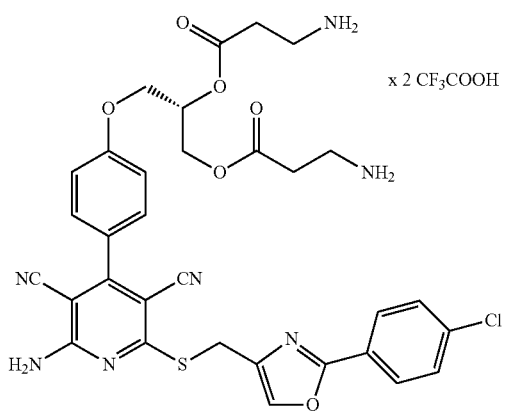 [SMILES: N#Cc1c(N)nc(SCc2coc(-c3ccc(Cl)cc3)n2)c(C#N)c1-c1ccc(OC[C@@H](COC(=O)CCN)OC(=O)CCN)cc1]

An amount of 860 mg (0.736 mmol) of the compound from example 28A was introduced in 3 ml of dichloromethane and admixed with 0.57 ml (7.360 mmol) of trifluoroacetic acid. After 2 hours of stirring at RT, the dichloromethane was stripped off under reduced pressure and the residue was purified by means of preparative HPLC (eluent gradient: acetonitrile/water 10:90→95:5 with addition of 0.1% TFA). This gave 532 mg (80% of theory) of the target compound.

LC-MS (method 6): $R_t$=1.09 min; MS (ESIpos): m/z=676 [M+H]⁺.

Example 31A (10S,18S)-19-{4-[2-Amino-6-({[2-(4-chlorophenyl)-1,3-oxazol-4-yl]methyl}sulfanyl)-3,5-dicyanopyridin-4-yl]phenoxy}-10-[(tert-butoxycarbonyl)amino]-2,2-dimethyl-4,11,15-trioxo-3,16-dioxa-5,12-diazanonadecan-18-yl 3-({(2S)-2,6-bis[(tert-butoxycarbonyl)amino]hexanoyl}amino)propanoate

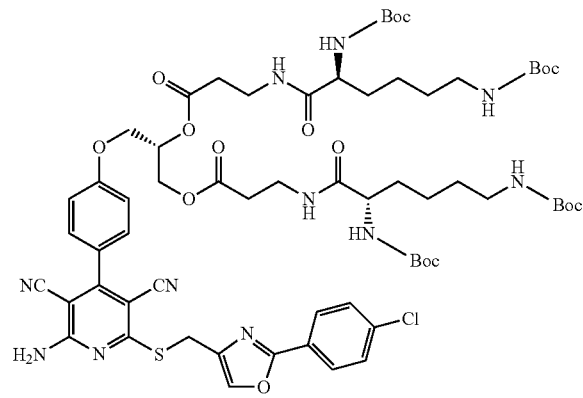 [SMILES: CC(C)(C)OC(=O)NCCCC[C@H](NC(=O)OC(C)(C)C)C(=O)NCCC(=O)OC[C@H](COc1ccc(-c2c(C#N)c(N)nc(SCc3coc(-c4ccc(Cl)cc4)n3)c2C#N)cc1)OC(=O)CCNC(=O)[C@H](CCCCNC(=O)OC(C)(C)C)NC(=O)OC(C)(C)C]

An amount of 192 mg (0.553 mmol) of N²,N⁶-bis(tert-butoxycarbonyl)-L-lysine was introduced in 2 ml of DMF, admixed with 51 mg (0.265 mmol) of 1-(3-dimethylaminopropyl)-3-ethylcarbodiimide hydrochloride and 45 mg (0.332 mmol) of 1-hydroxy-1H-benzotriazole hydrate and stirred for 10 minutes. Then 200 mg (0.221 mmol) of the compound from example 30A and 0.154 ml (0.885 mmol) of N,N-diisopropylethylamine were added and the mixture was stirred at RT overnight. The reaction batch was subsequently purified directly by means of preparative HPLC (eluent gradient: acetonitrile/water 10:90→95:5). This gave 77 mg (26% of theory) of the target compound.

LC-MS (method 4): $R_t$=3.15 min; MS (ESIpos): m/z=1332 [M+H]⁺.

Example 32A (14S)-15-{4-[2-Amino-6-({[2-(4-chlorophenyl)-1,3-oxazol-4-yl]methyl}sulfanyl)-3,5-dicyanopyridin-4-yl]phenoxy}-2,2-dimethyl-4,7,11-trioxo-3,12-dioxa-5,8-diazapentadecan-14-yl 3-({[(tert-butoxycarbonyl)amino]acetyl}amino)propanoate

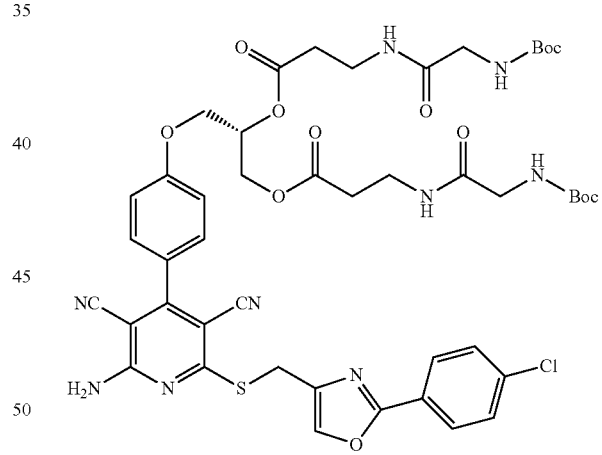

The title compound was prepared in the same way as for the preparation of example 31A, starting from the compound from example 30A and commercial N-(tert-butoxycarbonyl)glycine.

Yield: 34% of theory

LC-MS (method 4): $R_t$=2.73 min; MS (ESIpos): m/z=990 [M+H]⁺.

Example 33A (6S,14S)-15-{4-[2-Amino-6-({[2-(4-chlorophenyl)-1,3-oxazol-4-yl]methyl}sulfanyl)-3,5-dicyanopyridin-4-yl]phenoxy}-2,2-dimethyl-6-(2-methylpropyl)-4,7,11-trioxo-3,12-dioxa-5,8-diazapentadecan-14-yl 3-({(2S)-2-[(tert-butoxycarbonyl)amino]-4-methylpentanoyl}amino)propanoate

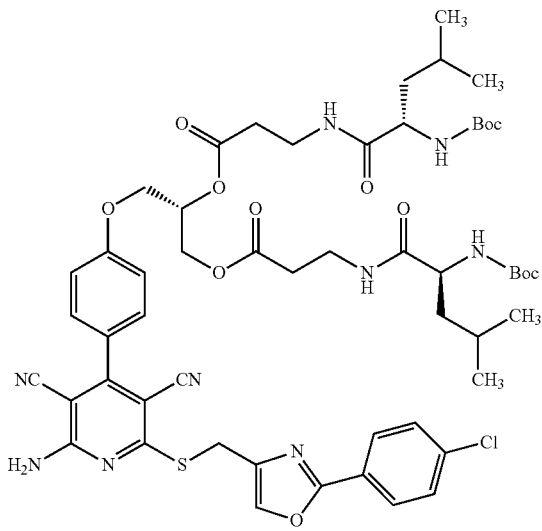 [SMILES: CC(C)C[C@H](NC(=O)OC(C)(C)C)C(=O)NCCC(=O)OC[C@H](COc1ccc(-c2c(C#N)c(N)nc(SCc3coc(-c4ccc(Cl)cc4)n3)c2C#N)cc1)OC(=O)CCNC(=O)[C@H](CC(C)C)NC(=O)OC(C)(C)C]

The title compound was prepared in the same way as for the preparation of example 31A, starting from the compound from example 30A and commercial N-(tert-butoxycarbonyl)-L-leucine.

Yield: 34% of theory

LC-MS (method 5): $R_t$=1.64 min; MS (ESIpos): m/z=1102 [M+H]$^+$.

Example 34A (6S,14S)-15-{4-[2-Amino-6-({[2-(4-chlorophenyl)-1,3-oxazol-4-yl]methyl}sulfanyl)-3,5-dicyanopyridin-4-yl]phenoxy}-2,2-dimethyl-4,7,1'-trioxo-6-(propan-2-yl)-3,12-dioxa-5,8-diazapentadecan-14-yl 3-({(2S)-2-[(tert-butoxycarbonyl)amino]-3-methylbutanoyl}amino)propanoate

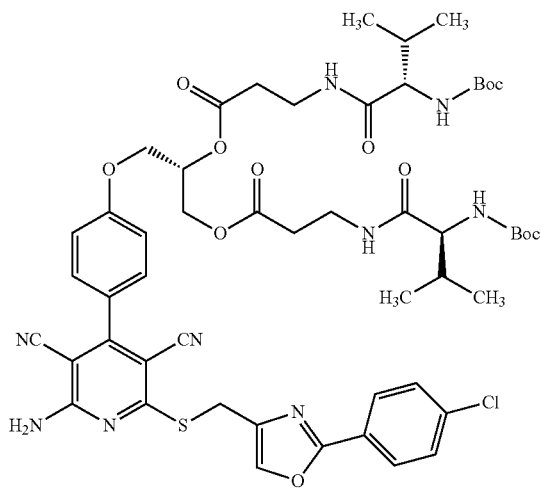 [SMILES: CC(C)[C@H](NC(=O)OC(C)(C)C)C(=O)NCCC(=O)OC[C@H](COc1ccc(-c2c(C#N)c(N)nc(SCc3coc(-c4ccc(Cl)cc4)n3)c2C#N)cc1)OC(=O)CCNC(=O)[C@@H](NC(=O)OC(C)(C)C)C(C)C]

The title compound was prepared in the same way as for the preparation of example 31A, starting from the compound from example 30A and commercial N-(tert-butoxycarbonyl)-L-valine.

Yield: 31% of theory

LC-MS (method 5): $R_t$=1.57 min; MS (ESIpos): m/z=1074 [M+H]$^+$.

Example 35A (2S)-3-{4-[2-Amino-6-({[2-(4-chlorophenyl)-1,3-oxazol-4-yl]methyl}sulfanyl)-3,5-dicyanopyridin-4-yl]phenoxy}propane-1,2-diyl (2S,2'S)-bis{2-[(tert-butoxycarbonyl)amino]-4-methylpentanoate}

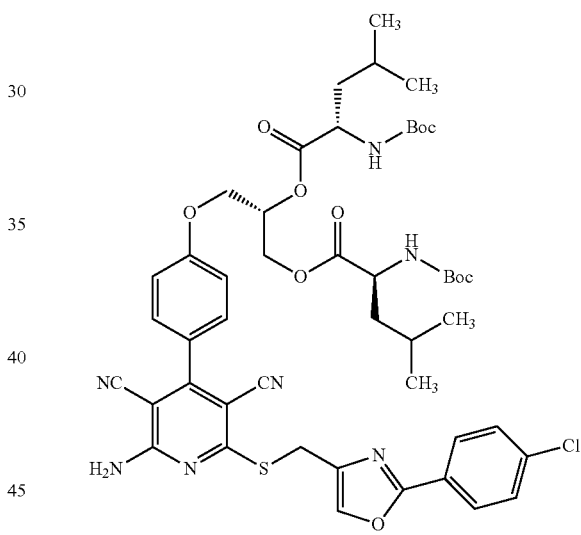

An amount of 250 mg (0.468 mmol) of the compound from example 8A was introduced in 10 ml of dichloromethane, admixed with 271 mg (1.170 mmol) of N-(tert-butoxycarbonyl)-L-leucine, 269 mg (1.405 mmol) of 1-(3-dimethylaminopropyl)-3-ethylcarbodiimide hydrochloride and 5.7 mg (0.047 mmol) of 4-N,N-dimethylaminopyridine and stirred at RT overnight. The reaction mixture was subsequently concentrated and the residue was purified by means of preparative HPLC (eluent gradient: acetonitrile/water 10:90→95:5). This gave 327 mg (73% of theory) of the target compound.

LC-MS (method 10): $R_t$=3.29 min; MS (ESIpos): m/z=960 [M+H

Example 36A (2S)-3-{4-[2-Amino-6-({[2-(4-chlorophenyl)-1,3-oxazol-4-yl]methyl}sulfanyl)-3,5-dicyanopyridin-4-yl]phenoxy}propane-1,2-diyl (2S,2'S)-bis(2-amino-4-methylpentanoate)bis(trifluoroacetic acid) salt

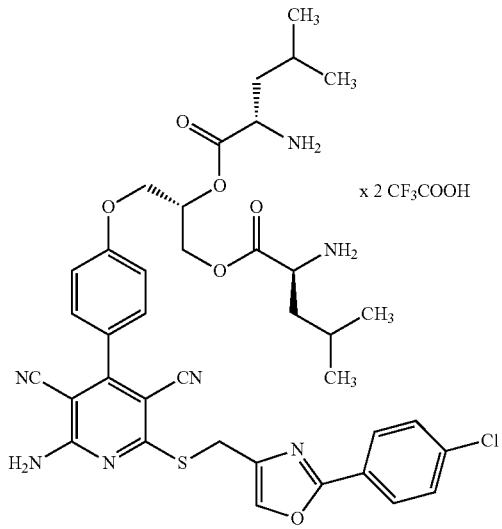 [SMILES: CC(C)C[C@H](N)C(=O)OC[C@H](COc1ccc(-c2c(C#N)c(N)nc(SCc3coc(-c4ccc(Cl)cc4)n3)c2C#N)cc1)OC(=O)[C@@H](N)CC(C)C]

An amount of 327 mg (0.340 mmol) of the compound from example 35A was introduced in 1 ml of dichloromethane, admixed with 0.262 ml (3.404 mmol) of trifluoroacetic acid and stirred at RT for 3 hours. The reaction mixture was subsequently concentrated under reduced pressure and the residue was purified by means of preparative HPLC (eluent gradient: acetonitrile/water 10:90→95:5 with addition of 0.1% TFA). This gave 217 mg (64% of theory) of the target compound.

LC-MS (method 10): $R_t$=1.81 min; MS (ESIpos): m/z=760 [M+H]$^+$.

Example 37A (10S,14S)-15-{4-[2-Amino-6-({[2-(4-chlorophenyl)-1,3-oxazol-4-yl]methyl}sulfanyl)-3,5-dicyanopyridin-4-yl]phenoxy}-2,2-dimethyl-10-(2-methylpropyl)-4,8,11-trioxo-3,12-dioxa-5,9-diazapentadecan-14-yl (2S)-2-({3-[(tert-butoxycarbonyl)amino]propanoyl}amino)-4-methylpentanoate

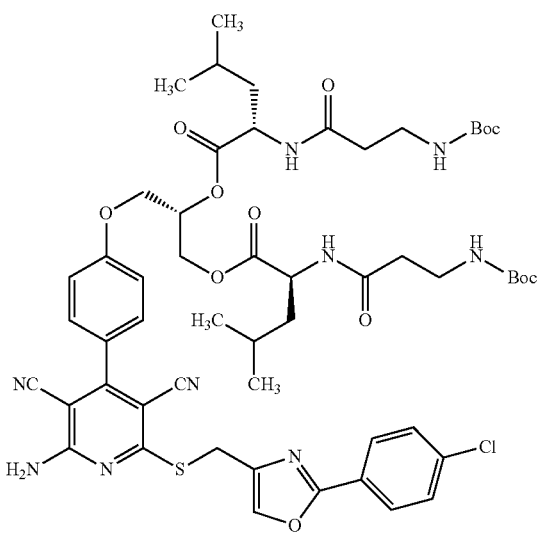 [SMILES: CC(C)C[C@H](NC(=O)CCNC(=O)OC(C)(C)C)C(=O)OC[C@H](COc1ccc(-c2c(C#N)c(N)nc(SCc3coc(-c4ccc(Cl)cc4)n3)c2C#N)cc1)OC(=O)[C@H](CC(C)C)NC(=O)CCNC(=O)OC(C)(C)C]

An amount of 104 mg (0.549 mmol) of N-(tert-butoxycarbonyl)-β-alanine was introduced in 2 ml of DMF, admixed with 51 mg (0.265 mmol) of 1-(3-dimethylaminopropyl)-3-ethylcarbodiimide hydrochloride and 45 mg (0.332 mmol) of 1-hydroxy-1H-benzotriazole hydrate and stirred for 10 minutes. Then 217 mg (0.221 mmol) of the compound from example 36A and 0.154 ml (0.885 mmol) of N,N-diisopropylethylamine were added and the mixture was stirred at RT for 7 hours. Thereafter, again, the same amounts of N-(tert-butoxycarbonyl)-β-alanine, 1-(3-dimethylaminopropyl)-3-ethylcarbodiimide hydrochloride, 1-hydroxy-1H-benzotriazole hydrate and N,N-diisopropylethylamine were added and the mixture was stirred at RT overnight. The DMF was subsequently stripped off under reduced pressure and the residue was partitioned between water and dichloromethane. The organic phase was dried over sodium sulfate and concentrated. This gave 240 mg of the crude target compound (54% purity, 54% of theory), which was used without further purification in the following reaction.

LC-MS (method 5): $R_t$=1.65 min; MS (ESIpos): m/z=1102 [M+H]$^+$.

Example 38A (2S)-3-{4-[2-Amino-6-({[2-(4-chlorophenyl)-1,3-oxazol-4-yl]methyl}sulfanyl)-3,5-dicyanopyridin-4-yl]phenoxy}propane-1,2-diyl (2S,2'S)-bis{2-[(tert-butoxycarbonyl)amino]-3-methylbutanoate}

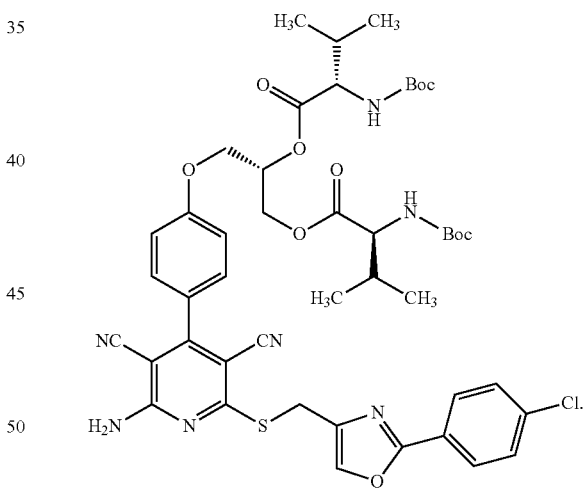

An amount of 250 mg (0.468 mmol) of the compound from example 8A was introduced in 10 ml of dichloromethane, admixed with 254 mg (1.170 mmol) of N-(tert-butoxycarbonyl)-L-valine, 269 mg (1.405 mmol) of 1-(3-dimethylaminopropyl)-3-ethylcarbodiimide hydrochloride and 5.7 mg (0.047 mmol) of 4-N,N-dimethylaminopyridine and stirred at RT overnight. The reaction mixture was subsequently concentrated under reduced pressure and the residue was purified by means of preparative HPLC (eluent gradient: acetonitrile/water 10:90→95:5). This gave 354 mg (81% of theory) of the target compound.

LC-MS (method 10): $R_t$=3.18 min; MS (ESIpos): m/z=932 [M+H]$^+$.

Example 39A (2S)-3-{4-[2-Amino-6-({[2-(4-chlorophenyl)-1,3-oxazol-4-yl]methyl}sulfanyl)-3,5-dicyanopyridin-4-yl]phenoxy}propane-1,2-diyl (2S,2'S)-bis(2-amino-3-methylbutanoate)bis(trifluoroacetic acid) salt

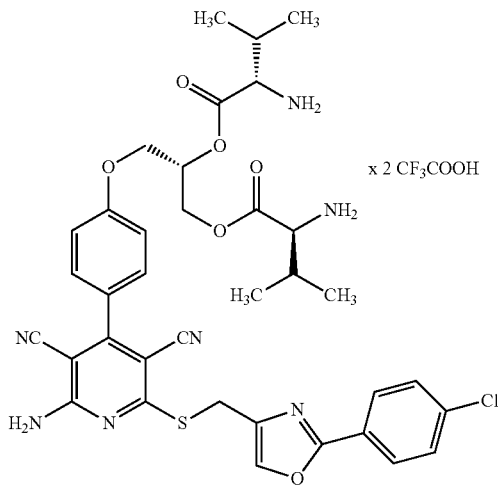 [SMILES: CC(C)[C@H](N)C(=O)OC[C@H](COc1ccc(-c2c(C#N)c(N)nc(SCc3coc(-c4ccc(Cl)cc4)n3)c2C#N)cc1)OC(=O)[C@@H](N)C(C)C]

An amount of 354 mg (0.380 mmol) of the compound from example 38A was introduced in 1 ml of dichloromethane, admixed with 0.262 ml (3.796 mmol) of trifluoroacetic acid and stirred at RT for 3 hours. Then the same amount of trifluoroacetic acid was added and the mixture was stirred further at RT overnight. The reaction mixture was subsequently concentrated and the residue was purified by means of preparative HPLC (eluent gradient: acetonitrile/water 10:90→95:5 with addition of 0.1% TFA). This gave 279 mg (77% of theory) of the target compound.

LC-MS (method 10): $R_t$=1.76 min; MS (ESIpos): m/z=732 [M+H]$^+$.

Example 40A (10S,14S)-15-{4-[2-Amino-6-({[2-(4-chlorophenyl)-1,3-oxazol-4-yl]methyl}sulfanyl)-3,5-dicyanopyridin-4-yl]phenoxy}-2,2-dimethyl-4,8,11-trioxo-10-(propan-2-yl)-3,12-dioxa-5,9-diazapentadecan-14-yl (2S)-2-({3-[(tert-butoxycarbonyl)amino]propanoyl}amino)-3-methylbutanoate

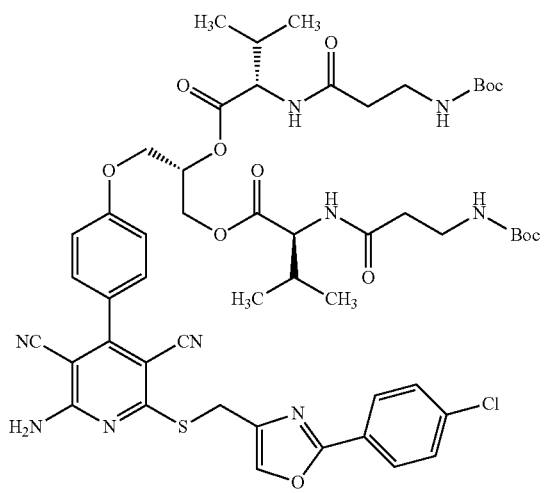 [SMILES: CC(C)[C@H](NC(=O)CCNC(=O)OC(C)(C)C)C(=O)OC[C@H](COc1ccc(-c2c(C#N)c(N)nc(SCc3coc(-c4ccc(Cl)cc4)n3)c2C#N)cc1)OC(=O)[C@@H](NC(=O)CCNC(=O)OC(C)(C)C)C(C)C]

An amount of 62 mg (0.325 mmol) of N-(tert-butoxycarbonyl)-β-alanine was introduced in 1 ml of DMF, admixed with 30 mg (0.156 mmol) of 1-(3-dimethylaminopropyl)-3-ethylcarbodiimide hydrochloride and 26 mg (0.195 mmol) of 1-hydroxy-1H-benzotriazole hydrate and stirred for 10 minutes. Then 217 mg (0.221 mmol) of the compound from example 39A and 0.91 ml (0.521 mmol) of N,N-diisopropylethylamine were added and the mixture was stirred at RT overnight. Thereafter, again, half of each of the initial amounts of N-(tert-butoxycarbonyl)-β-alanine, 1-(3-dimethylaminopropyl)-3-ethylcarbodiimide hydrochloride, 1-hydroxy-1H-benzotriazole hydrate and N,N-diisopropylethylamine were added and the mixture was stirred at RT for a further 2 hours. The DMF was subsequently stripped off under reduced pressure and the residue was partitioned between water and dichloromethane. The organic phase was dried over sodium sulfate and concentrated. This gave 216 mg of the target compound, which was used as the crude product, without further purification, in the following reaction.

LC-MS (method 7): $R_t$=3.07 min; MS (ESIpos): m/z=1074 [M+H]$^+$.

Example 41A (6R,9S,12S)-12-({4-[2-Amino-6-({[2-(4-chlorophenyl)-1,3-oxazol-4-yl]methyl}sulfanyl)-3,5-dicyanopyridin-4-yl]phenoxy}methyl)-2,2,6,9-tetramethyl-4,7,10-trioxo-3,11-dioxa-5,8-diazamidecan-13-yl (2S)-2-({(2R)-2-[(tert-butoxycarbonyl)amino]propanoyl}amino)propanoate

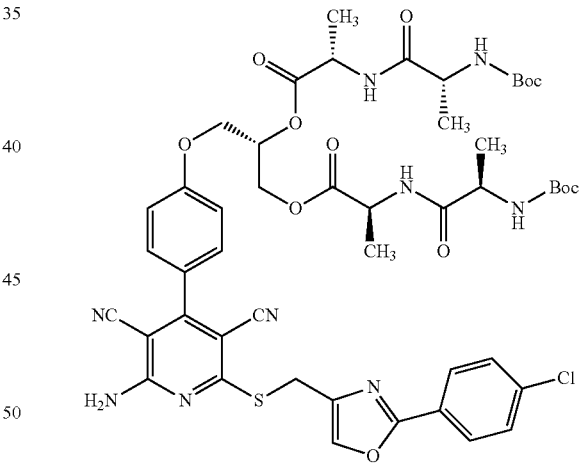

An amount of 265 mg (1.402 mmol) of N-(tert-butoxycarbonyl)-D-alanine was introduced in 5 ml of DMF, admixed with 269 mg (1.402 mmol) of 1-(3-dimethylaminopropyl)-3-ethylcarbodiimide hydrochloride and 307 mg (2.002 mmol) of 1-hydroxy-1H-benzotriazole hydrate and stirred for 10 minutes. Then 500 mg (0.667 mmol) of the compound from example 11A and 0.581 ml (3.337 mmol) of N,N-diisopropylethylamine were added and the mixture was stirred at RT for 2 hours. The reaction mixture was subsequently purified by two-fold preparative HPLC (eluent gradient: acetonitrile/water 10:90→95:5). This gave 318 mg (47% of theory) of the target compound.

LC-MS (method 8): $R_t$=1.33 min; MS (ESIpos): m/z=1018 [M+H]$^+$.

Example 42A (2S)-3-{4-[2-Amino-6-({[2-(4-chlorophenyl)-1,3-oxazol-4-yl]methyl}sulfanyl)-3,5-dicyanopyridin-4-yl]phenoxy}propane-1,2-diyl (2R,2'R)-bis{2-[(tert-butoxycarbonyl)amino]propanoate}

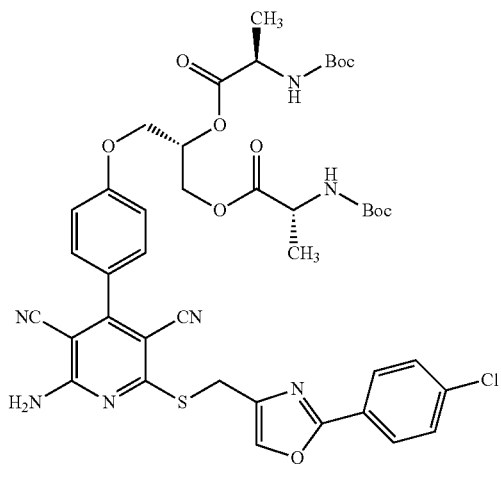 [SMILES: C[C@@H](NC(=O)OC(C)(C)C)C(=O)OC[C@H](COc1ccc(-c2c(C#N)c(N)nc(SCc3coc(-c4ccc(Cl)cc4)n3)c2C#N)cc1)OC(=O)[C@@H](C)NC(=O)OC(C)(C)C]

An amount of 1.063 g (5.618 mmol) of N-(tert-butoxycarbonyl)-D-alanine was introduced in 10 ml of DMF and admixed with 448 mg (2.341 mmol) of 1-(3-dimethylaminopropyl)-3-ethylcarbodiimide hydrochloride and 114 mg (0.936 mmol) of 4-N,N-dimethylaminopyridine. After 5 minutes of stirring, 500 mg (0.936 mmol) of the compound from example 8A were added and the mixture was stirred at RT for 2 hours. The product was subsequently isolated by means of preparative HPLC (acetonitrile/water gradient 10:90→95:5). This gave 676 mg (82% of theory) of the target compound.

LC-MS (method 8): $R_t$=1.42 min; MS (ESIneg): m/z=874 [M−H]⁻.

Example 43A (2S)-3-{4-[2-Amino-6-({[2-(4-chlorophenyl)-1,3-oxazol-4-yl]methyl}sulfanyl)-3,5-dicyanopyridin-4-yl]phenoxy}propane-1,2-diyl (2R,2'R)-bis(2-aminopropanoate)dihydrochloride

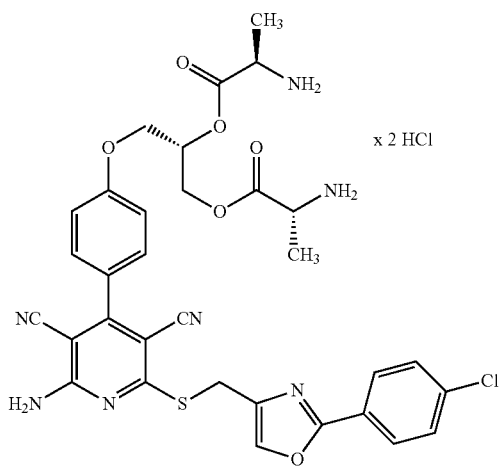 [SMILES: C[C@@H](N)C(=O)OC[C@H](COc1ccc(-c2c(C#N)c(N)nc(SCc3coc(-c4ccc(Cl)cc4)n3)c2C#N)cc1)OC(=O)[C@@H](C)N]

An amount of 675 mg (0.770 mmol) of the compound from example 42A was introduced in 8 ml of dichloromethane and admixed with 15.4 ml of a 1M solution of hydrogen chloride gas in diethyl ether. After 4 hours of stirring, the precipitated solid was isolated by suction filtration, washed with dichloromethane and diethyl ether and dried under reduced pressure. This gave 577 mg (quantitative) of the target compound.

¹H-NMR (400 MHz, DMSO-$d_6$): δ=8.55 (br. m, 6H), 8.38 (s, 1H), 8.33-8.02 (br. s, 2H), 7.97 (d, 2H), 7.61 (d, 2H), 7.50 (d, 2H), 7.13 (d, 2H), 5.51 (m, 1H), 4.56-4.44 (m, 2H), 4.42 (s, 2H), 4.39-4.33 (m, 2H), 4.16 (m, 2H), 1.44 (d, 3H), 1.39 (d, 3H).

LC-MS (method 8): $R_t$=0.87 min; MS (ESIpos): m/z=676 [M+H]⁺.

Example 44A (6R,9R,12S)-12-({4-[2-Amino-6-({[2-(4-chlorophenyl)-1,3-oxazol-4-yl]methyl}sulfanyl)-3,5-dicyanopyridin-4-yl]phenoxy}methyl)-2,2,6,9-tetramethyl-4,7,10-trioxo-3,11-dioxa-5,8-diazamidecan-13-yl (2R)-2-({(2R)-2-[(tert-butoxycarbonyl)amino]propanoyl}amino)propanoate

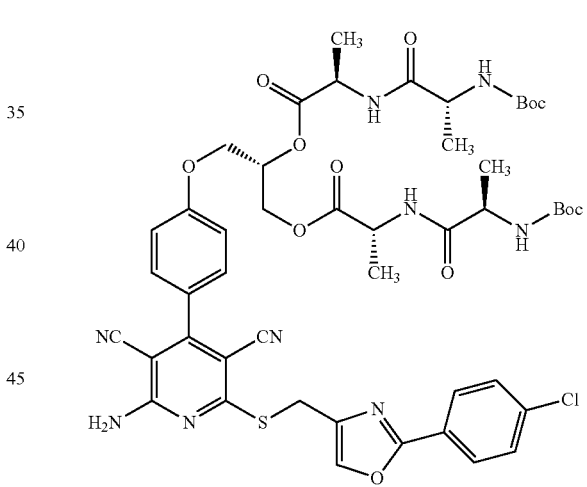

An amount of 239 mg (1.262 mmol) of N-(tert-butoxycarbonyl)-D-alanine was introduced in 4.5 ml of DMF, admixed with 242 mg (1.262 mmol) of 1-(3-dimethylaminopropyl)-3-ethylcarbodiimide hydrochloride and 276 mg (1.802 mmol) of 1-hydroxy-1H-benzotriazole hydrate and stirred for 10 minutes. Then 450 mg (0.601 mmol) of the compound from example 43A and 0.523 ml (3.004 mmol) of N,N-diisopropylethylamine were added and the mixture was stirred at RT for 4 hours. The reaction batch was subsequently purified directly by means of preparative HPLC (eluent gradient: acetonitrile/water 10:90→95:5). This gave 438 mg (72% of theory) of the target compound.

LC-MS (method 8): $R_t$=1.34 min; MS (ESIpos): m/z=1018 [M+H]⁺.

Example 45A (6S,9S,12S)-12-({4-[2-Amino-6-({[2-(4-chlorophenyl)-1,3-oxazol-4-yl]methyl}sulfanyl)-3,5-dicyanopyridin-4-yl]phenoxy}methyl)-2,2,9-trimethyl-4,7,10-trioxo-6-(propan-2-yl)-3,11-dioxa-5,8-diazamidecan-13-yl (2S)-2-({(2S)-2-[(tert-butoxycarbonyl)amino]-3-methylbutanoyl}amino)propanoate

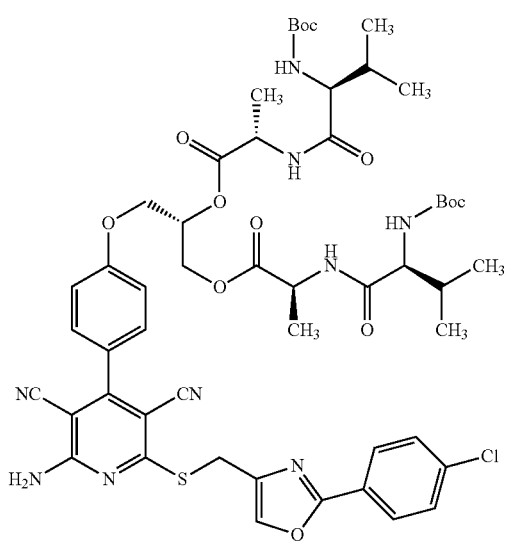 [SMILES: CC(C)[C@H](NC(=O)OC(C)(C)C)C(=O)N[C@@H](C)C(=O)OC[C@H](COc1ccc(-c2c(C#N)c(N)nc(SCc3coc(-c4ccc(Cl)cc4)n3)c2C#N)cc1)OC(=O)[C@H](C)NC(=O)[C@@H](NC(=O)OC(C)(C)C)C(C)C]

An amount of 122 mg (0.561 mmol) of N-(tert-butoxycarbonyl)-L-valine was introduced in 10 ml of DMF and admixed in succession with 107.5 mg (0.561 mmol) of 1-(3-dimethylaminopropyl)-3-ethylcarbodiimide hydrochloride, 108 mg (0.801 mmol) of 1-hydroxy-1H-benzotriazole, hydrate, 200 mg (0.267 mmol) of the compound from example 11A and 0.233 ml (1.33 mmol) of N,N-diisopropylethylamine. Subsequently the reaction mixture was stirred at RT overnight. Thereafter the batch was concentrated under reduced pressure and the residue was taken up in 500 ml of dichloromethane. It was washed in each case twice with 10% strength citric acid solution and 10% strength sodium hydrogencarbonate solution and the organic phase was subsequently concentrated. The residue was taken up in 25 ml of ethyl acetate and admixed with stirring with a mixture of 10 ml of diethyl ether and 10 ml of pentane. After an hour of stirring at RT, the precipitate was isolated by suction filtration and dried under a high vacuum. This gave 240 mg (84% of theory) of the target compound.

LC-MS (method 5): $R_t$=1.63 min; MS (ESIpos): m/z=1074 [M+H]$^+$.

Example 46A (6S,13S)-13-({4-[2-Amino-6-({[2-(4-chlorophenyl)-1,3-oxazol-4-yl]methyl}sulfanyl)-3,5-dicyanopyridin-4-yl]phenoxy}methyl)-2,2,6-trimethyl-4,7,11-trioxo-3,12-dioxa-5,8-diazatetradecan-14-yl 3-({(2S)-2-[(tert-butoxycarbonyl)amino]propanoyl}amino)propanoate

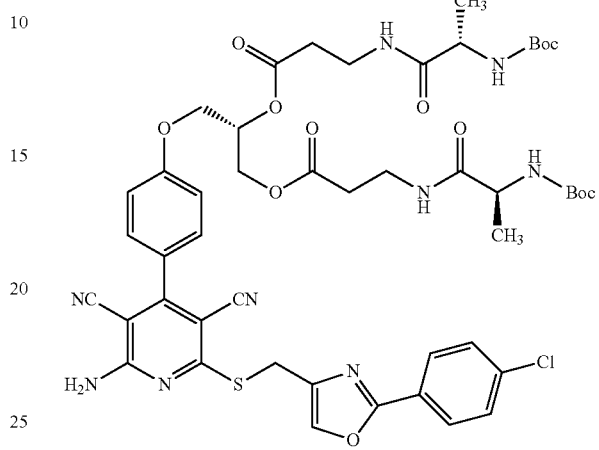

The title compound was prepared in the same way as for the preparation of example 45A, starting from the compound from example 30A and commercial N-(tert-butoxycarbonyl)-L-alanine.

Yield: 73% of theory

LC-MS (method 6): $R_t$=2.39 min; MS (ESIpos): m/z=1018 [M+H]$^+$.

Example 47A (10S,13S)-13-({4-[2-Amino-6-({[2-(4-chlorophenyl)-1,3-oxazol-4-yl]methyl}sulfanyl)-3,5-dicyanopyridin-4-yl]phenoxy}methyl)-2,2,10-trimethyl-4,8,11-trioxo-3,12-dioxa-5,9-diazatetradecan-14-yl (2S)-2-({3-[(tert-butoxycarbonyl)amino]propanoyl}amino)propanoate

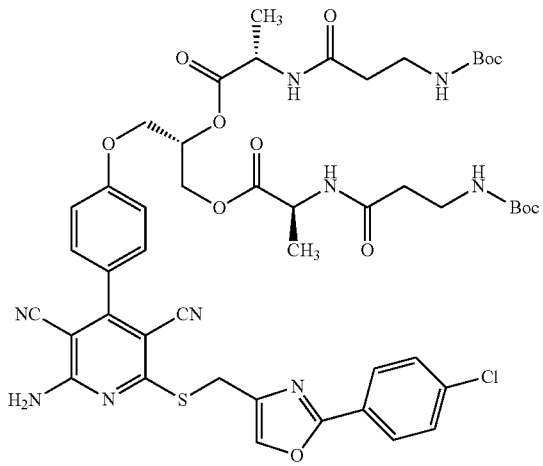 [SMILES: C[C@H](NC(=O)CCNC(=O)OC(C)(C)C)C(=O)OC[C@H](COc1ccc(-c2c(C#N)c(N)nc(SCc3coc(-c4ccc(Cl)cc4)n3)c2C#N)cc1)OC(=O)[C@H](C)NC(=O)CCNC(=O)OC(C)(C)C]

The title compound was prepared in the same way as for the preparation of example 45A, starting from the compound from example 11A and commercial N-(tert-butoxycarbonyl)-β-alanine.

Yield: 78% of theory

LC-MS (method 5): $R_t$=1.47 min; MS (ESIpos): m/z=1018 [M+H]$^+$.

Example 48A (6S,9S,12S)-12-({4-[2-Amino-6-({[2-(4-chlorophenyl)-1,3-oxazol-4-yl]methyl}sulfanyl)-3,5-dicyanopyridin-4-yl]phenoxy}methyl)-2,2,6,9-tetramethyl-4,7,10-trioxo-3,11-dioxa-5,8-diazamidecan-13-yl (2S)-2-({(2S)-2-[(tert-butoxycarbonyl)amino]propanoyl}amino)propanoate

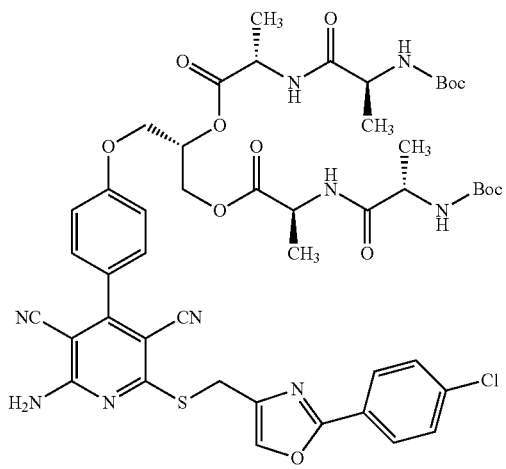 [SMILES: C[C@H](NC(=O)OC(C)(C)C)C(=O)N[C@@H](C)C(=O)OC[C@H](COc1ccc(-c2c(C#N)c(N)nc(SCc3coc(-c4ccc(Cl)cc4)n3)c2C#N)cc1)OC(=O)[C@H](C)NC(=O)[C@H](C)NC(=O)OC(C)(C)C]

The title compound was prepared in the same way as for the preparation of example 45A, starting from the compound from example 11A and commercial N-(tert-butoxycarbonyl)-L-alanine.

Yield: 77% of theory

LC-MS (method 5): $R_t$=1.47 min; MS (ESIpos): m/z=1018 [M+H]$^+$.

Example 49A (2R)-3-{4-[2-Amino-6-({[2-(4-chlorophenyl)-1,3-oxazol-4-yl]methyl}sulfanyl)-3,5-dicyanopyridin-4-yl]phenoxy}propane-1,2-diyl (2S,2'S)-bis{2-[(tert-butoxycarbonyl)amino]propanoate}

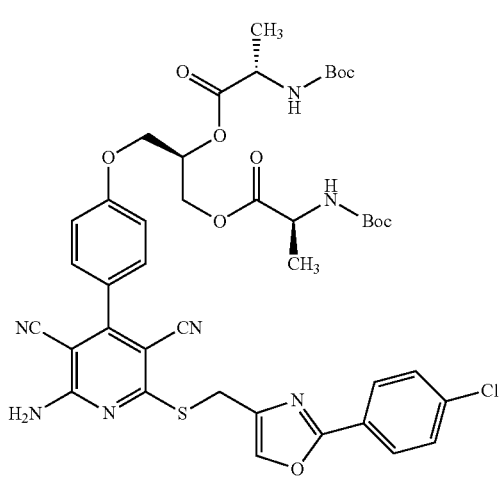 [SMILES: C[C@H](NC(=O)OC(C)(C)C)C(=O)OC[C@@H](COc1ccc(-c2c(C#N)c(N)nc(SCc3coc(-c4ccc(Cl)cc4)n3)c2C#N)cc1)OC(=O)[C@H](C)NC(=O)OC(C)(C)C]

An amount of 213 mg (1.12 mmol) of N-Boc-L-alanine was introduced in 2 ml of DMF and admixed in succession with 93 mg (0.49 mmol) of 1-(3-dimethylaminopropyl)-3-ethylcarbodiimide hydrochloride, 23 mg (0.19 mmol) of 4-N,N-dimethylaminopyridine and 200 mg (0.375 mmol) of the compound from example 9A. The reaction mixture was then stirred at RT for 2 hours. Thereafter, again, the same amounts of N-Boc-L-alanine, 1-(3-dimethylaminopropyl)-3-ethylcarbodiimide hydrochloride and 4-N,N-dimethylaminopyridine were added and the mixture was stirred further at RT overnight. The reaction batch was then purified directly by means of preparative HPLC (Eluent: acetonitrile/water gradient). This gave 293 mg (86% of theory) of the target compound.

LC-MS (method 7): $R_t$=3.17 min; MS (ESIpos): m/z=876 [M+H]$^+$.

Example 50A (2R)-3-{4-[2-Amino-6-({[2-(4-chlorophenyl)-1,3-oxazol-4-yl]methyl}sulfanyl)-3,5-dicyanopyridin-4-yl]phenoxy}propane-1,2-diyl (2S,2'S)-bis(2-aminopropanoat)dihydrochloride

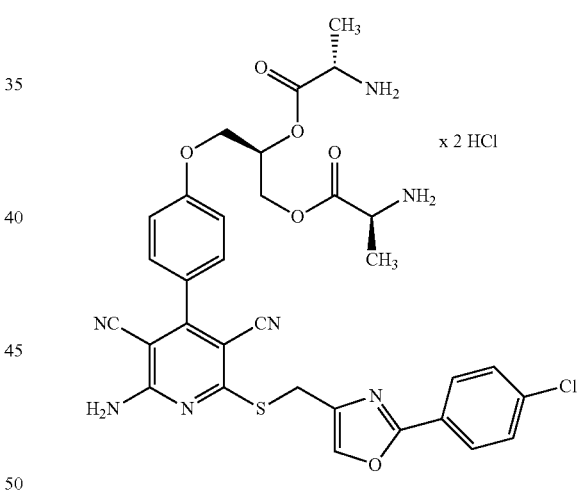

An amount of 282 g (0.32 mmol) of the compound from example 49A was introduced in 3 ml of dichloromethane and admixed dropwise with 1.6 ml (3.2 mmol) of a 2M solution of hydrogen chloride in diethyl ether. The mixture was stirred at room temperature for three hours and then concentrated under reduced pressure. The residue was admixed with 5 ml of acetonitrile and the mixture was then concentrated again. This procedure was repeated once more. Drying of the residue under reduced pressure gave 215 mg (89% of theory) of the target compound.

LC-MS (method 5): $R_t$=0.99 min; MS (ESIpos): m/z=676 [M+H]$^+$.

Example 51A (10S,13S,17R)-18-{4-[2-Amino-6-({[2-(4-chlorophenyl)-1,3-oxazol-4-yl]methyl}sulfanyl)-3,5-dicyanopyridin-4-yl]phenoxy}-10-[(tert-butoxycarbonyl)amino]-2,2,13-trimethyl-4,11,14-trioxo-3,15-dioxa-5,12-diazaoctadecan-17-yl (2S)-2-({(2S)-2,6-bis[(tert-butoxycarbonyl)amino]hexanoyl}amino)propanoate

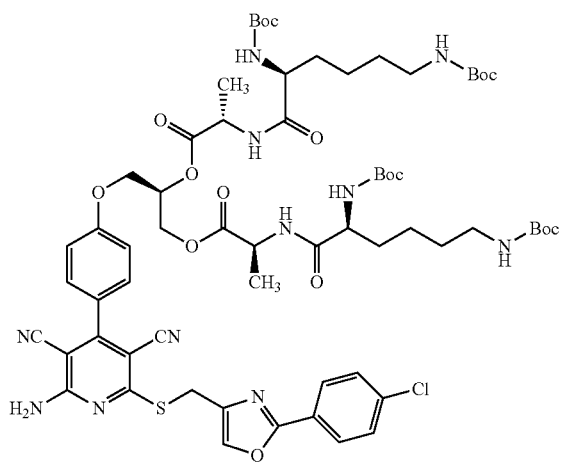 [SMILES: C[C@H](NC(=O)[C@H](CCCCNC(=O)OC(C)(C)C)NC(=O)OC(C)(C)C)C(=O)OC[C@@H](COc1ccc(-c2c(C#N)c(N)nc(SCc3coc(-c4ccc(Cl)cc4)n3)c2C#N)cc1)OC(=O)[C@H](C)NC(=O)[C@H](CCCCNC(=O)OC(C)(C)C)NC(=O)OC(C)(C)C]

An amount of 333 mg (0.63 mmol) of $N^2,N^6$-bis(tert-butoxycarbonyl)-L-lysine dicyclohexylamine salt was introduced in 2.9 ml of DMF and admixed in succession with 116 mg (0.86 mmol) of 1-hydroxy-1H-benzotriazole hydrate, 132 mg (0.69 mmol) of 1-(3-dimethylaminopropyl)-3-ethylcarbodiimide hydrochloride, 0.25 ml (1.44 mmol) of N,N-diisopropylethylamine and 215 mg (0.29 mmol) of the compound from example 50A. The reaction mixture was then stirred at RT overnight. Thereafter it was admixed with water and the precipitate formed was isolated by filtration. The solid was dissolved in about 5 ml of acetonitrile and purified by means of preparative HPLC (eluent: acetonitrile/water gradient). This gave 297 mg (35% of theory) of the target compound.

LC-MS (method 6): $R_t$=2.82 min; MS (ESIpos): m/z=1334 $[M+H]^+$.

Example 52A (10S,13S,17S)-18-{4-[2-Amino-6-({[2-(4-chlorophenyl)-1,3-oxazol-4-yl]methyl}sulfanyl)-3,5-dicyanopyridin-4-yl]phenoxy}-10-[(tert-butoxycarbonyl)amino]-2,2,13-trimethyl-4,11,14-trioxo-3,15-dioxa-5,12-diazaoctadecan-17-yl (2S)-2-({(2S)-2,6-bis{tert-butoxycarbonyl)amino]hexanoyl}amino)propanoate

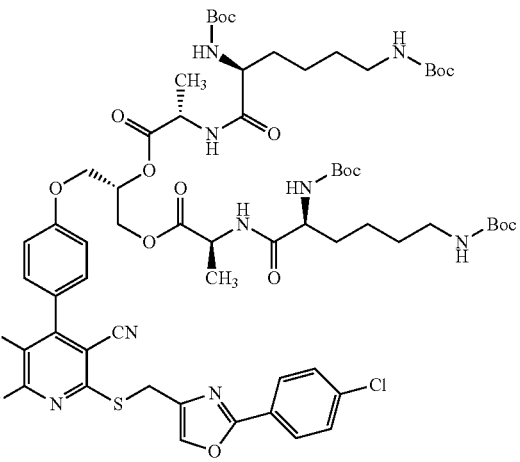

An amount of 372 mg (0.71 mmol) of $N^2,N^6$-bis(tert-butoxycarbonyl)-L-lysine dicyclohexylamine salt was introduced in 3.2 ml of DMF and admixed in succession with 130 mg (0.96 mmol) of 1-hydroxy-1H-benzotriazole hydrate, 147 mg (0.77 mmol) of 1-(3-dimethylaminopropyl)-3-ethylcarbodiimide hydrochloride, 0.28 ml (1.60 mmol) of N,N-diisopropylethylamine and 240 mg (0.32 mmol) of the compound from example 11A. The reaction mixture was then stirred at RT overnight. Thereafter it was admixed with water and the precipitate formed was isolated by filtration. The solid was dissolved in about 5 ml of acetonitrile and purified by means of preparative HPLC (eluent: acetonitrile/water gradient). This gave 326 mg (35% of theory) of the target compound.

LC-MS (method 7): $R_t$=3.24 min; MS (ESIpos): m/z=1334 $[M+H]^+$.

Example 53A (2S)-3-{4-[2-Amino-6-({[2-(4-chlorophenyl)-1,3-oxazol-4-yl]methyl}sulfanyl)-3,5-dicyanopyridin-4-yl]phenoxy}propane-1,2-diyl (2S,3R,2'S,3'R)-bis{3-tert-butoxy-2-[(tert-butoxycarbonyl)amino]butanoate

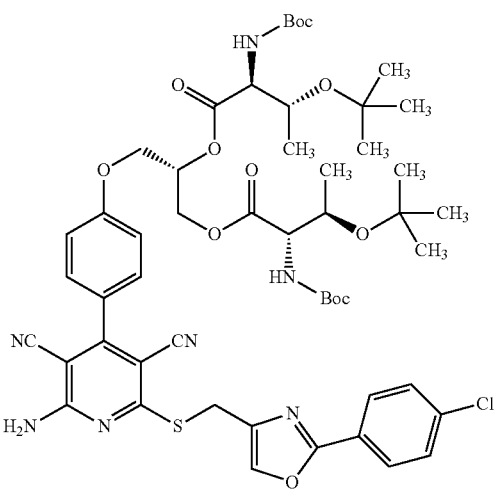 [SMILES: C[C@@H](OC(C)(C)C)[C@H](NC(=O)OC(C)(C)C)C(=O)OC[C@H](COc1ccc(-c2c(C#N)c(N)nc(SCc3coc(-c4ccc(Cl)cc4)n3)c2C#N)cc1)OC(=O)[C@@H](NC(=O)OC(C)(C)C)[C@@H](C)OC(C)(C)C]

An amount of 800 mg (1.50 mmol) of the compound from example 8A was introduced in 16 ml of DMF/dichloromethane (1:1) and admixed in succession with 1.237 g (4.49 mmol) of N-(tert-butoxycarbonyl)-O-tert-butyl-L-threonine, 1.005 g (5.24 mmol) of 1-(3-dimethylaminopropyl)-3-ethylcarbodiimide hydrochlorid and 36 mg (0.30 mmol) of 4-N,N-dimethylaminopyridine. The reaction mixture was then stirred at RT overnight and subsequently concentrated under reduced pressure. The residue was admixed with a little acetonitrile and purified by means of preparative HPLC (eluent: acetonitrile/water+0.1% TFA). This gave 916 mg (58% of theory) of the target compound.

LC-MS (method 5): $R_t$=1.92 min; MS (ESIpos): m/z=1048 [M+H]$^+$.

Example 54A (2S)-3-{4-[2-Amino-6-({[2-(4-chlorophenyl)-1,3-oxazol-4-yl]methyl}sulfanyl)-3,5-dicyanopyridin-4-yl]phenoxy}propane-1,2-diyl(2S,3R,2'S,3'R)-bis(2-amino-3-hydroxybutanoate)bis(trifluoroacetic acid) salt

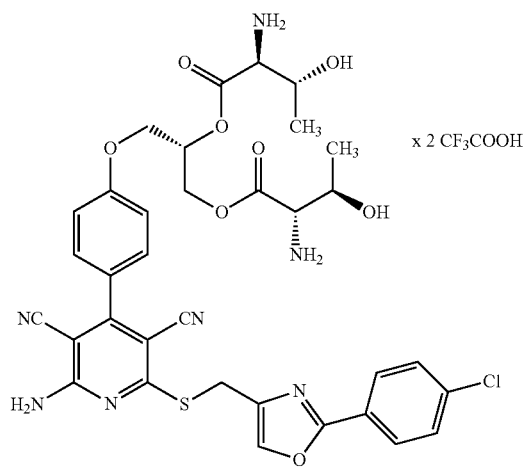 [SMILES: C[C@@H](O)[C@H](N)C(=O)OC[C@H](COc1ccc(-c2c(C#N)c(N)nc(SCc3coc(-c4ccc(Cl)cc4)n3)c2C#N)cc1)OC(=O)[C@@H](N)[C@@H](C)O]

An amount of 916 mg (0.873 mmol) of the compound from example 53A was introduced in 10 ml of dichloromethane, admixed dropwise with 1.35 ml (17.47 mmol) of trifluoroacetic acid and stirred at RT overnight. The reaction mixture was subsequently concentrated under reduced pressure and the residue was purified by means of preparative HPLC (eluent: acetonitrile/water+0.1% TFA). This gave 574 mg (68% of theory) of the target compound.

$^1$H-NMR (400 MHz, DMSO-d$_6$): δ=8.42-8.25 (m, 5H), 8.15 (br. s, 2H), 7.98 (d, 2H), 7.61 (d, 2H), 7.51 (d, 2H), 7.12 (d, 2H), 5.68 (br. s, 1H), 5.50 (quint, 1H), 4.50 (d, 2H), 4.42 (s, 2H), 4.38-4.32 (m, 2H), 4.24-3.95 (m, 5H), 1.24-1.18 (m, 6H).

LC-MS (method 7): $R_t$=1.45 min; MS (ESIpos): m/z=736 [M+H]$^+$.

Example 55A (9S,13S)-14-{4-[2-Amino-6-({[2-(4-chlorophenyl)-1,3-oxazol-4-yl]methyl}sulfanyl)-3,5-dicyanopyridin-4-yl]phenoxy}-9-[(1R)-1-hydroxyethyl]-2,2-dimethyl-4,7,10-trioxo-3,11-dioxa-5,8-diazatetradecan-13-yl (2S,3R)-2-({[(tert-butoxycarbonyl)amino]acetyl}amino)-3-hydroxybutanoate

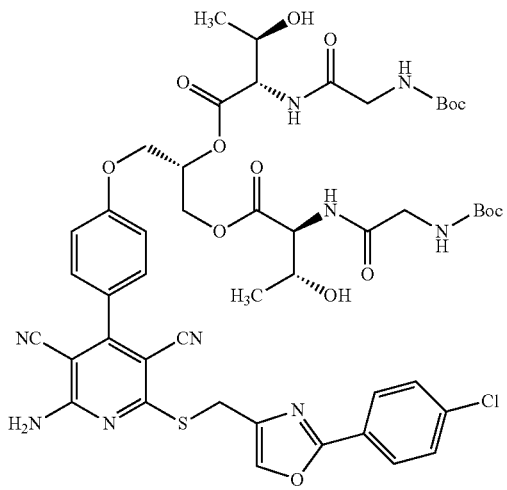 [SMILES: C[C@@H](O)[C@H](NC(=O)CNC(=O)OC(C)(C)C)C(=O)OC[C@H](COc1ccc(-c2c(C#N)c(N)nc(SCc3coc(-c4ccc(Cl)cc4)n3)c2C#N)cc1)OC(=O)[C@@H](NC(=O)CNC(=O)OC(C)(C)C)[C@@H](C)O]

An amount of 94 mg (0.54 mmol) of N-(tert-butoxycarbonyl)glycine was introduced in 0.95 ml of DMF at 0° C. and admixed with 154 mg (0.40 mmol) of N-[(dimethylamino)(3H-[1,2,3]triazolo[4,5-b]pyridin-3-yloxy)methylidene]-N-methylmethanaminium hexafluorophosphate (HATU). After 20 minutes of stirring, at 0° C., 130 mg (0.14 mmol) of the compound from example 54A and 0.07 ml (0.40 mmol) of N,N-diisopropylethylamine were added. The reaction mixture was then stirred at 60° C. overnight. Thereafter it was admixed with a little water/THF and the mixture was purified directly by means of preparative HPLC (eluent: acetonitrile/water+0.1% TFA). This gave 100 mg (61% of theory) of the target compound.

LC-MS (method 7): $R_t$=2.72 min; MS (ESIpos): m/z=1051 [M+H]$^+$.

Example 56A (6S,9S,13S)-14-{4-[2-Amino-6-({[2-(4-chlorophenyl)-1,3-oxazol-4-yl]methyl}sulfanyl)-3,5-dicyanopyridin-4-yl]phenoxy}-9-[(1R)-1-hydroxyethyl]-2,2,6-trimethyl-4,7,10-trioxo-3,11-dioxa-5,8-diazatetradecan-13-yl (2S,3R)-2-({(2S)-2-[(tert-butoxycarbonyl)amino]propanoyl}amino)-3-hydroxybutanoate

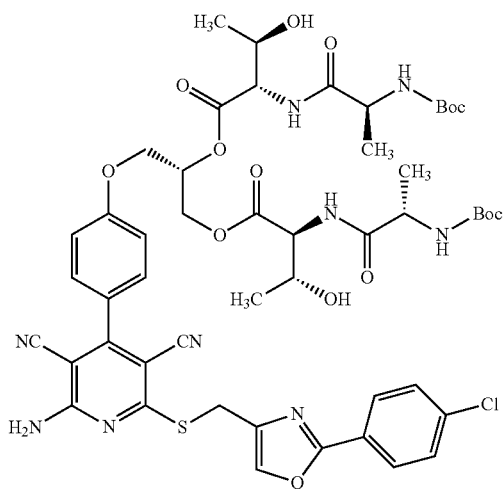 [SMILES: C[C@H](NC(=O)OC(C)(C)C)C(=O)N[C@H](C(=O)OC[C@H](COc1ccc(-c2c(C#N)c(N)nc(SCc3coc(-c4ccc(Cl)cc4)n3)c2C#N)cc1)OC(=O)[C@@H](NC(=O)[C@H](C)NC(=O)OC(C)(C)C)[C@@H](C)O)[C@@H](C)O]

An amount of 212 mg (1.12 mmol) of N-(tert-butoxycarbonyl)-L-alanine was introduced in 1.97 ml of DMF at 0° C. and admixed with 319 mg (0.84 mmol) of N-[(dimethylamino)(3H-[1,2,3]triazolo[4,5-b]pyridin-3-yloxy)methylidene]-N-methylmethanaminium hexafluorophosphate (HATU). After 20 minutes of stirring, at 0° C., 270 mg (0.28 mmol) of the compound from example 54A and 0.15 ml (0.84 mmol) of N,N-diisopropylethylamine were added. The reaction mixture was subsequently stirred at 60° C. overnight. Thereafter it was admixed with a little water/THF and the mixture was purified directly by means of preparative HPLC (eluent: acetonitrile/water+0.1% TFA). This gave 188 mg (62% of theory) of the target compound.

LC-MS (method 5): $R_t$=1.44 min; MS (ESIpos): m/z=1079 [M+H]$^+$.

Example 57A (6S,14S)-15-{4-[2-Amino-6-({[2-(4-chlorophenyl)-1,3-oxazol-4-yl]methyl}sulfanyl)-3,5-dicyanopyridin-4-yl]phenoxy}-6-[(1R)-1-tert-butoxyethyl]-2,2-dimethyl-4,7,11-trioxo-3,12-dioxa-5,8-diazapentadecan-14-yl 3-({(2S,3R)-3-tert-butoxy-2-[(tert-butoxycarbonyl)amino]butanoyl}amino)propanoate

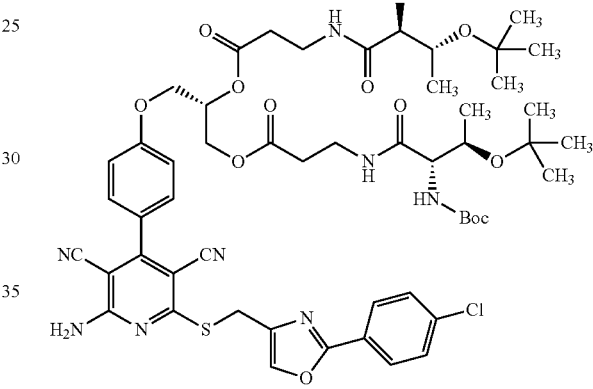

An amount of 134 mg (0.49 mmol) of N-(tert-butoxycarbonyl)-O-tert-butyl-L-threonine was introduced in 3 ml of DMF and admixed with 102 mg (0.53 mmol) of 1-(3-dimethylaminopropyl)-3-ethylcarbodiimide hydrochloride, 90 mg (0.66 mmol) of 1-hydroxy-1H-benzotriazole hydrate and 0.29 ml (1.66 mmol) of N,N-diisopropylethylamine. After 15 minutes of stirring at RT, 200 mg (0.22 mmol) of the compound from example 30A were added. The reaction mixture was subsequently stirred at RT overnight. Thereafter it was admixed with a little water/THF and the mixture was purified directly by means of preparative HPLC (eluent: acetonitrile/water+0.1% TFA). This gave 106 mg (40% of theory) of the target compound.

LC-MS (method 5): $R_t$=1.76 min; MS (ESIpos): m/z=1190 [M+H]$^+$.

EXEMPLARY EMBODIMENTS

Example 1

(2S)-3-{4-[2-Amino-6-({[2-(4-chlorophenyl)-1,3-oxazol-4-yl]methyl}sulfanyl)-3,5-dicyanopyridin-4-yl]phenoxy}propane-1,2-diyl (2S,2'S)-bis(2-{[(2S)-2-amino-4-methylpentanoyl]amino}propanoate)bis(trifluoroacetic acid) salt

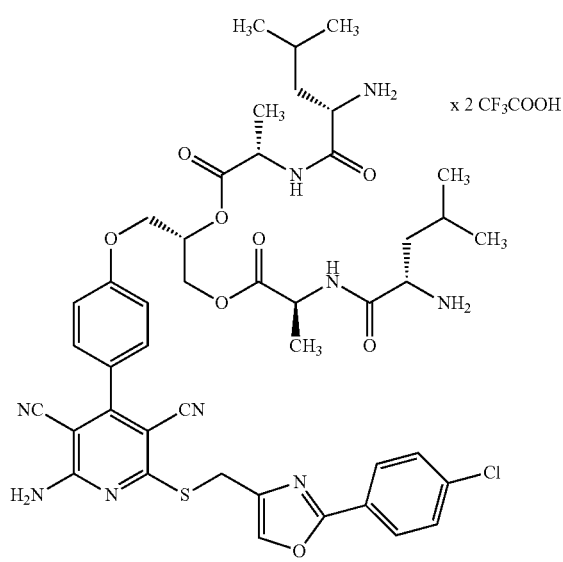 [SMILES: CC(C)C[C@H](N)C(=O)N[C@@H](C)C(=O)OC[C@H](COc1ccc(-c2c(C#N)c(N)nc(SCc3coc(-c4ccc(Cl)cc4)n3)c2C#N)cc1)OC(=O)[C@H](C)NC(=O)[C@@H](N)CC(C)C]

An amount of 185 mg (0.168 mmol) of the compound from example 13A was introduced in 2 ml of dichloromethane and admixed dropwise with 1.68 ml (3.36 mmol) of a 2M solution of hydrogen chloride in diethyl ether. After one hour of stirring at RT, the precipitated solid was isolated by suction filtration, washed with diethyl ether and dried under a high vacuum. This crude product was subsequently purified by means of preparative HPLC (eluent gradient: acetonitrile/water 10:90→95:5 with addition of 0.1% TFA). This gave 40 mg (21% of theory) of the target compound.

$^1$H-NMR (400 MHz, DMSO-d$_6$): δ=8.92 (d, 2H), 8.37 (s, 1H), 8.30-8.04 (m, 8H), 7.96 (d, 2H), 7.61 (d, 2H), 7.50 (d, 2H), 7.11 (d, 2H), 5.37 (m, 1H), 4.42-4.21 (m, 8H), 3.75 (br. s, 2H), 1.70 (br. m, 2H), 1.62-1.46 (br. m, 4H), 1.35 (q, 6H), 0.92-0.86 (m, 12H).

LC-MS (method 7): R$_t$=1.55 min; MS (ESIpos): m/z=902 [M+H]$^+$.

Example 2

(2S)-3-{4-[2-Amino-6-({[2-(4-chlorophenyl)-1,3-oxazol-4-yl]methyl}sulfanyl)-3,5-dicyanopyridin-4-yl]phenoxy}propane-1,2-diyl (2S,2'S)-bis(2-{[(2S,3S)-2-amino-3-methylpentanoyl]amino}propanoate) dihydrochloride

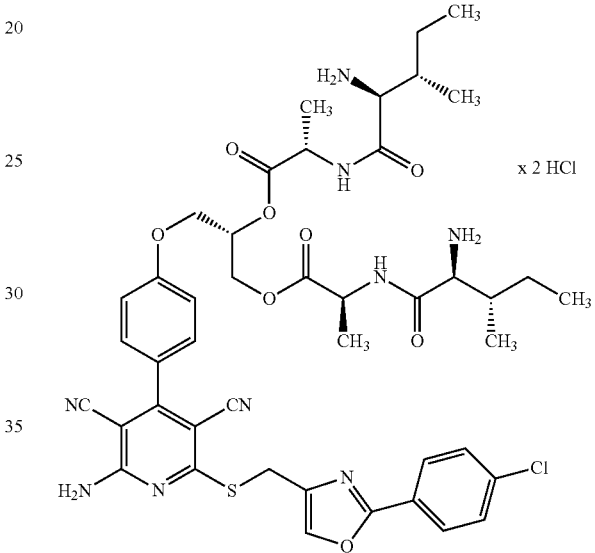

An amount of 177 mg (0.161 mmol) of the compound from example 14A was introduced in 2 ml of dichloromethane and admixed dropwise with 1.61 ml (3.21 mmol) of a 2M solution of hydrogen chloride in diethyl ether. After one hour of stirring at RT, the precipitated solid was isolated by suction filtration, washed with diethyl ether and dried under a high vacuum. This gave 128 mg (78% of theory) of the target compound.

$^1$H-NMR (400 MHz, DMSO-d$_6$): δ=8.90 (d, 2H), 8.41 (s, 1H), 8.17 (m, 6H), 7.97 (d, 2H), 7.61 (d, 2H), 7.49 (d, 2H), 7.10 (d, 2H), 5.40 (m, 1H), 4.42-4.21 (m, 8H), 3.64 (m, 2H), 1.84 (m, 2H), 1.56-1.51 (m, 4H), 1.34 (q, 6H), 1.16 (m, 2H), 0.92 (d, 6H), 0.88-0.83 (m, 6H).

LC-MS (method 5): R$_t$=1.04 min; MS (ESIpos): m/z=902 [M+H]$^+$.

Example 3

(2S)-3-{4-[2-Amino-6-({[2-(4-chlorophenyl)-1,3-oxazol-4-yl]methyl}sulfanyl)-3,5-dicyanopyridin-4-yl]phenoxy}propane-1,2-diyl (2S,2'S)-bis(2-{[(2S)-2,4-diaminobutanoyl]amino}propanoate) tetrahydrochloride

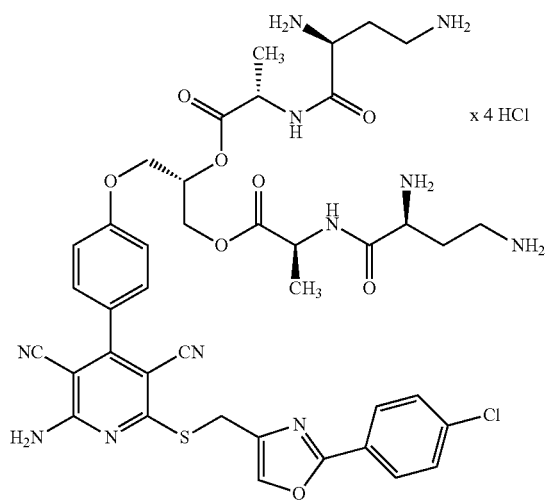 [SMILES: C[C@H](NC(=O)[C@@H](N)CCN)C(=O)OC[C@H](COc1ccc(-c2c(C#N)c(N)nc(SCc3coc(-c4ccc(Cl)cc4)n3)c2C#N)cc1)OC(=O)[C@H](C)NC(=O)[C@@H](N)CCN]

An amount of 163 mg (0.128 mmol) of the compound from example 15A was introduced in 2 ml of dichloromethane and admixed dropwise with 1.28 ml (2.55 mmol) of a 2M solution of hydrogen chloride in diethyl ether. After one hour of stirring at RT, the precipitated solid was isolated by suction filtration, washed with diethyl ether and dried under a high vacuum. This gave 117 mg (90% of theory) of the target compound.

$^1$H-NMR (400 MHz, DMSO-$d_6$): δ=9.44-9.39 (m, 2H), 8.55-8.39 (m, 7H), 8.38 (s, 1H), 8.29-8.13 (m, 7H), 7.97 (d, 2H), 7.60 (d, 2H), 7.50 (d, 2H), 7.14 (d, 2H), 5.40 (m, 1H), 4.49-4.26 (m, 8H), 4.15-4.02 (m, 2H), 3.09-2.95 (m, 4H), 2.15-2.02 (m, 4H), 1.37 (m, 6H).

LC-MS (method 8): $R_t$=0.70 min; MS (ESIneg): m/z=874 [M−H]$^−$.

Example 4

(2S)-3-{4-[2-Amino-6-({[2-(4-chlorophenyl)-1,3-oxazol-4-yl]methyl}sulfanyl)-3,5-dicyanopyridin-4-yl]phenoxy}propane-1,2-diyl (2S,2'S)-bis(2-{[(2S)-2,5-diaminopentanoyl]amino}propanoate) tetrahydrochloride

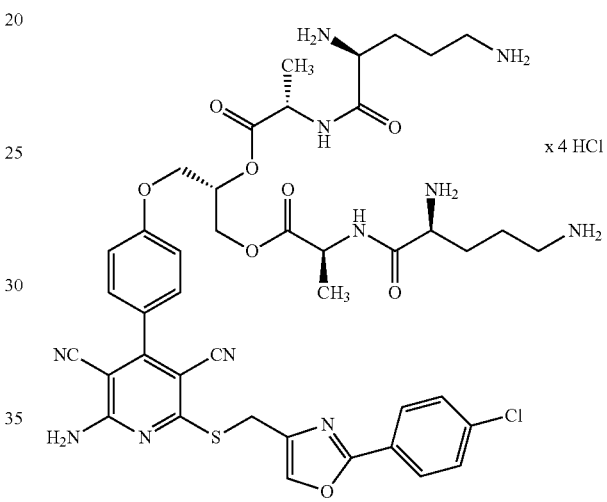

An amount of 184 mg (0.141 mmol) of the compound from example 16A was introduced in 2 ml of dichloromethane and admixed dropwise with 1.41 ml (2.82 mmol) of a 2M solution of hydrogen chloride in diethyl ether. After one hour of stirring at RT, the precipitated solid was isolated by suction filtration, washed with diethyl ether and dried under reduced pressure at 40° C. for 2 days. This gave 98 mg (66% of theory) of the target compound.

$^1$H-NMR (400 MHz, DMSO-$d_6$): δ=9.25 (m, 2H), 8.46-8.37 (m, 8H), 8.20-8.05 (m, 7H), 7.96 (d, 2H), 7.61 (d, 2H), 7.50 (d, 2H), 7.14 (d, 2H), 5.38 (m, 1H), 4.51-4.25 (m, 8H), 3.90 (m, 2H), 2.92 (m, 4H), 1.91-1.70 (m, 8H), 1.37 (m, 6H).

LC-MS (method 6): $R_t$=0.86 min; MS (ESIpos): m/z=904 [M+H]$^+$.

Example 5

(2S)-3-{4-[2-Amino-6-({[2-(4-chlorophenyl)-1,3-oxazol-4-yl]methyl}sulfanyl)-3,5-dicyanopyridin-4-yl]phenoxy}propane-1,2-diyl (2S,2'S)-bis(2-{[(2S)-2-amino-3-hydroxypropanoyl]amino}propanoate)bis(trifluoroacetic acid) salt

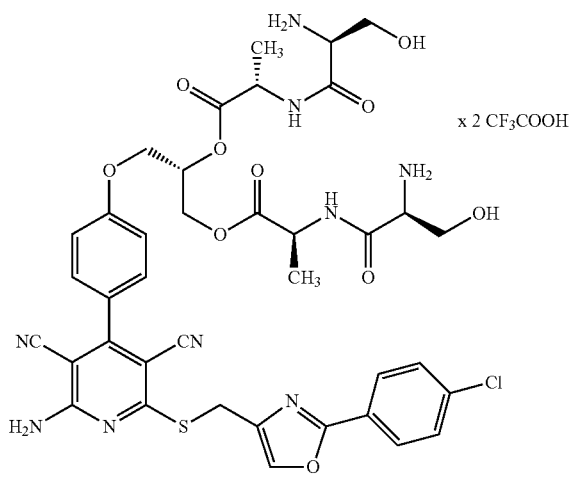 [SMILES: C[C@H](NC(=O)[C@@H](N)CO)C(=O)OC[C@H](COc1ccc(-c2c(C#N)c(N)nc(SCc3coc(-c4ccc(Cl)cc4)n3)c2C#N)cc1)OC(=O)[C@H](C)NC(=O)[C@@H](N)CO]

x 2 CF$_3$COOH

An amount of 158 mg (0.136 mmol) of the compound from example 17A was introduced in 2 ml of dichloromethane and admixed dropwise with 1.36 ml (2.72 mmol) of a 2M solution of hydrogen chloride in diethyl ether. After two hours of stirring at RT, the precipitated solid was isolated by suction filtration, washed with dichloromethane and dried under a high vacuum. Of the resulting crude product (yield: 100 mg), a portion of 50 mg was purified by means of preparative HPLC (eluent gradient: acetonitrile/water 10:90→95:5 with addition of 0.1% TFA). This gave 33 mg (22% of theory) of the target compound.

$^1$H-NMR (400 MHz, DMSO-d$_6$): δ=8.87 (m, 2H), 8.37 (s, 1H), 8.30-8.02 (m, 8H), 7.97 (d, 2H), 7.61 (d, 2H), 7.49 (d, 2H), 7.14 (d, 2H), 5.52 (br. m, 2H), 5.36 (m, 1H), 4.42-4.23 (m, 8H), 3.84-3.79 (m, 4H), 3.61 (m, 2H), 1.33 (m, 6H).

LC-MS (method 7): R$_t$=1.41 min; MS (ESIpos): m/z=850 [M+H]$^+$.

Example 6

(2S)-3-{4-[2-Amino-6-({[2-(4-chlorophenyl)-1,3-oxazol-4-yl]methyl}sulfanyl)-3,5-dicyanopyridin-4-yl]phenoxy}propane-1,2-diyl (2S,2'S)-bis(2-{[(2S)-2-amino-3-phenylpropanoyl]amino}propanoate)bis(trifluoroacetic acid) salt

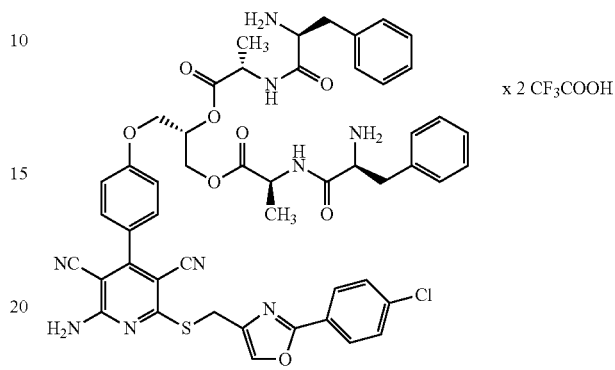

x 2 CF$_3$COOH

An amount of 160 mg (0.137 mmol) of the compound from example 18A was introduced in 2 ml of dichloromethane and admixed dropwise with 1.37 ml (2.73 mmol) of a 2M solution of hydrogen chloride in diethyl ether. After one hour of stirring at RT, the precipitated solid was isolated by suction filtration, washed with diethyl ether and dried under reduced pressure. Of the crude product thus obtained (yield: 102 mg), a portion of 50 mg was purified by means of preparative HPLC (eluent gradient: acetonitrile/water 10:90→95:5 with addition of 0.1% TFA). This gave 41 mg (25% of theory) of the target compound.

$^1$H-NMR (400 MHz, DMSO-d$_6$): δ=8.97 (m, 2H), 8.37 (s, 1H), 8.27-8.05 (m, 8H), 7.97 (d, 2H), 7.60 (d, 2H), 7.45 (d, 2H), 7.35-7.12 (m, 10H), 7.07 (d, 2H), 5.40 (m, 1H), 4.46-4.37 (m, 6H), 4.28 (m, 2H), 4.02 (br. s, 2H), 3.15 (m, 2H), 2.92 (m, 2H), 1.34 (m, 6H).

LC-MS (method 7): R$_t$=1.59 min; MS (ESIpos): m/z=970 [M+H]$^+$.

Example 7

(2S)-3-{4-[2-Amino-6-({[2-(4-chlorophenyl)-1,3-oxazol-4-yl]methyl}sulfanyl)-3,5-dicyanopyridin-4-yl]phenoxy}propane-1,2-diyl (2S,2'S)-bis{2-[(aminoacetyl)amino]propanoate}dihydrochloride

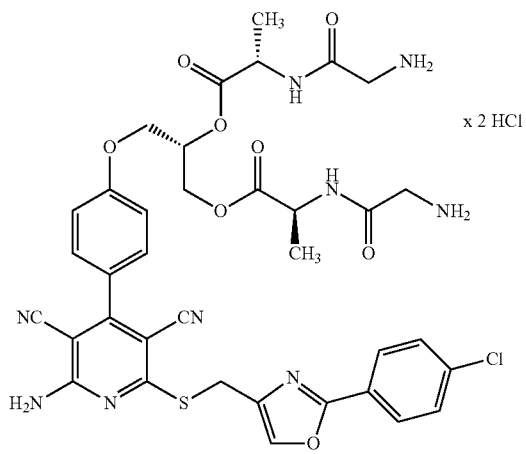 [SMILES: C[C@H](NC(=O)CN)C(=O)OC[C@H](COc1ccc(-c2c(C#N)c(N)nc(SCc3coc(-c4ccc(Cl)cc4)n3)c2C#N)cc1)OC(=O)[C@H](C)NC(=O)CN]

x 2 HCl

An amount of 2.37 g (2.393 mmol) of the compound from example 19A was dissolved in 200 ml of dichloromethane. Subsequently, with stirring, hydrogen chloride gas was passed through the solution at 15° C. for one hour. The precipitated solid was isolated by filtration, washed with dichloromethane and dried under reduced pressure. This gave 1.89 g (88% of theory) of the target compound.

$^1$H-NMR (400 MHz, DMSO-$d_6$): δ=8.94 (m, 2H), 8.39 (s, 1H), 8.32-8.00 (m, 8H), 7.96 (d, 2H), 7.61 (d, 2H), 7.49 (d, 2H), 7.14 (d, 2H), 5.40 (m, 1H), 4.42-4.24 (m, 8H), 3.64-3.51 (m, 4H), 1.33 (m, 6H).

LC-MS (method 7): $R_t$=1.46 min; MS (ESIpos): m/z=790 [M+H]$^+$.

Example 8

(2S)-3-{4-[2-Amino-6-({[2-(4-chlorophenyl)-1,3-oxazol-4-yl]methyl}sulfanyl)-3,5-dicyanopyridin-4-yl]phenoxy}propane-1,2-diyl (2S,2'S)-bis(2-{[(2S)-pyrrolidin-2-ylcarbonyl]amino}propanoate)bis(trifluoroacetic acid) salt

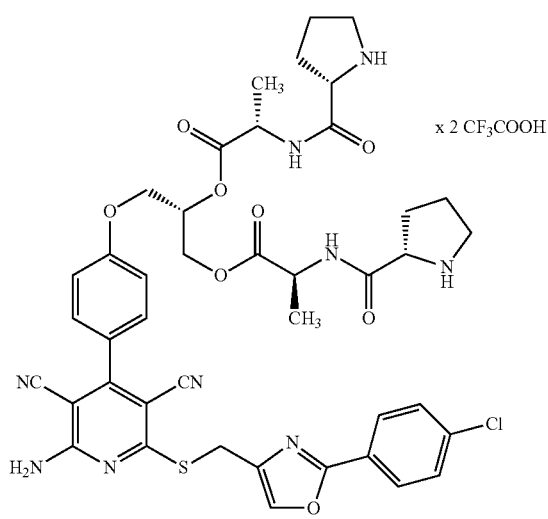 [SMILES: C[C@H](NC(=O)[C@@H]1CCCN1)C(=O)OC[C@H](COc1ccc(-c2c(C#N)c(N)nc(SCc3coc(-c4ccc(Cl)cc4)n3)c2C#N)cc1)OC(=O)[C@H](C)NC(=O)[C@@H]1CCCN1]

An amount of 180 mg (0.168 mmol) of the compound from example 20A was introduced in 1 ml of dichloromethane, admixed with 0.26 ml (3.362 mmol) of trifluoroacetic acid and stirred at RT for 2 h. Then the reaction mixture was concentrated and the residue was purified by means of preparative HPLC (eluent gradient: acetonitrile/water 10:90→95:5 with addition of 0.1% TFA). This gave 150 mg (81% of theory) of the target compound.

$^1$H-NMR (400 MHz, DMSO-$d_6$): δ=9.31 (m, 2H), 8.97 (m, 2H), 8.65-8.49 (m, 2H), 8.37 (s, 1H), 8.28-8.03 (br. s, 2H), 7.97 (d, 2H), 7.61 (d, 2H), 7.50 (d, 2H), 7.11 (d, 2H), 5.38 (m, 1H), 4.42-4.37 (m, 6H), 4.31-4.19 (m, 4H), 3.23 (m, 2H), 2.29 (m, 2H), 1.91-1.76 (m, 8H), 1.36-1.33 (d, 6H).

LC-MS (method 5): $R_t$=1.04 min; MS (ESIpos): m/z=870 [M+H]$^+$.

Example 9

(2S)-3-{4-[2-Amino-6-({[2-(4-chlorophenyl)-1,3-oxazol-yl]methyl}sulfanyl)-3,5-dicyanopyridin-4-yl]phenoxy}propane-1,2-diyl (2S,2'S)-bis(2-{[(2S)-2,4-diamino-4-oxobutanoyl]amino}propanoate)bis(trifluoroacetic acid) salt

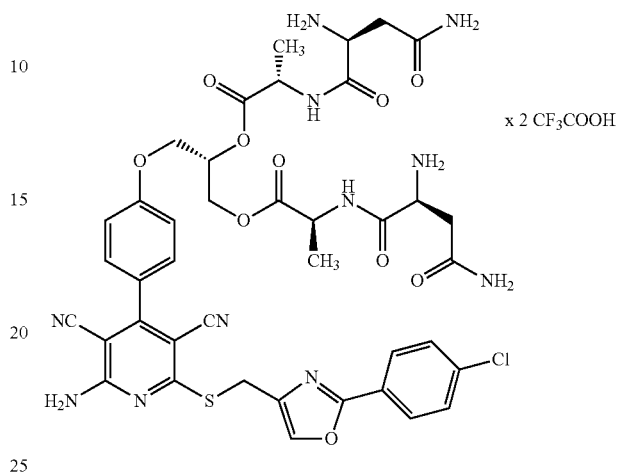

An amount of 64 mg (0.042 mmol) of the compound from example 23A was introduced in 1 ml of dichloromethane, admixed with 0.033 ml (0.423 mmol) of trifluoroacetic acid and stirred at RT overnight. The reaction mixture was then concentrated and the residue was purified by means of preparative HPLC (eluent gradient: acetonitrile/water 10:90→95:5 with addition of 0.1% TFA). This gave 18 mg (37% of theory) of the target compound.

$^1$H-NMR (400 MHz, DMSO-$d_6$): δ=8.86 (m, 2H), 8.36 (s, 1H), 8.28-7.99 (m, 8H), 7.97 (d, 2H), 7.71 (br. s, 2H), 7.61 (d, 2H), 7.50 (d, 2H), 7.30 (br. s, 2H), 7.13 (d, 2H), 5.38 (m, 1H), 4.45-4.24 (m, 8H), 4.10 (m, 2H), 2.76-2.67 (m, 2H), 2.61-2.56 (m, 2H), 1.32 (m, 6H).

LC-MS (method 6): $R_t$=1.20 min; MS (ESIpos): m/z=904 [M+H]$^+$.

Example 10

(3S,6S,9S,13S,16S)-3,16-Diamino-9-({4-[2-amino-6-({[2-(4-chlorophenyl)-1,3-oxazol-4-yl]methyl}sulfanyl)-3,5-dicyanopyridin-4-yl]phenoxy}methyl)-6,13-dimethyl-4,7,12,15-tetraoxo-8,11-dioxa-5,14-diazaoctadecane-1,18-dioic acid bis(trifluoroacetic acid) salt

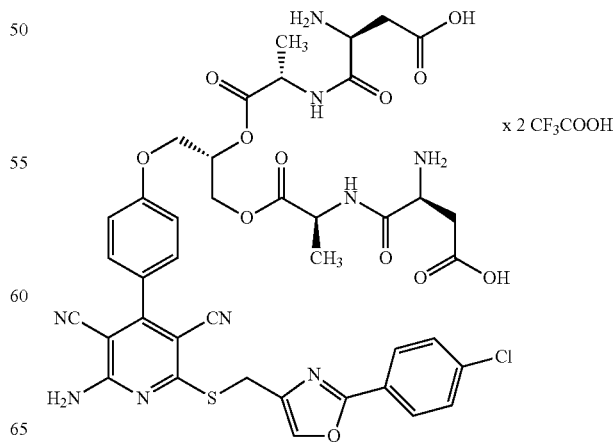

An amount of 410 mg (0.336 mmol) of the compound from example 24A was introduced in 2 ml of dichloromethane, admixed with 0.259 ml (3.364 mmol) of trifluoroacetic acid and stirred at RT overnight. The reaction mixture was then concentrated and the residue was purified by means of preparative HPLC (eluent gradient: acetonitrile/water 10:90→95:5 with addition of 0.1% TFA). This gave 191 mg (50% of theory) of the target compound.

$^1$H-NMR (400 MHz, DMSO-d$_6$): δ=13.40-12.77 (br. s, 2H), 8.90-8.88 (m, 2H), 8.37 (s, 1H), 8.21 (m, 6H), 7.97 (d, 2H), 7.61 (d, 2H), 7.49 (d, 2H), 7.13 (d, 2H), 5.38 (m, 1H), 4.42-4.23 (m, 8H), 4.12 (m, 2H), 2.89-2.82 (m, 2H), 2.79-2.66 (m, 2H), 1.33 (m, 6H). LC-MS (method 7): R$_t$=1.80 min; MS (ESIpos): m/z=906 [M+H]$^+$.

Example 11

(4S,7S,10S,14S,17S)-4,17-Diamino-10-({4-[2-amino-6-({[2-(4-chlorophenyl)-1,3-oxazol-4-yl]methyl}sulfanyl)-3,5-dicyanopyridin-4-yl]phenoxy}methyl)-7,14-dimethyl-5,8,13,16-tetraoxo-9,12-dioxa-6,15-diazaicosane-1,20-dioic acid bis(trifluoroacetic acid) salt

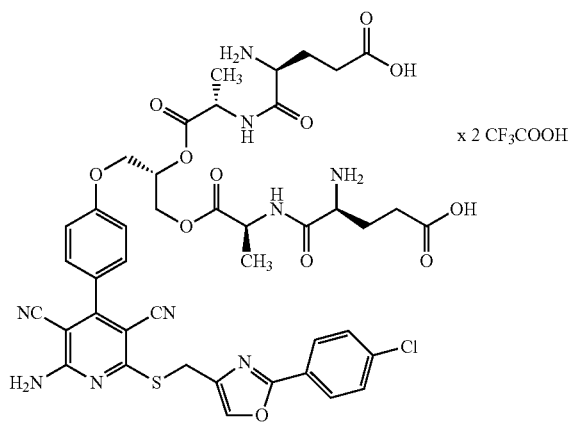 [SMILES: C[C@H](NC(=O)[C@@H](N)CCC(=O)O)C(=O)OC[C@H](COc1ccc(-c2c(C#N)c(N)nc(SCc3coc(-c4ccc(Cl)cc4)n3)c2C#N)cc1)OC(=O)[C@H](C)NC(=O)[C@@H](N)CCC(=O)O]

An amount of 410 mg (0.336 mmol) of the compound from example 25A was introduced in 2 ml of dichloromethane, admixed with 0.222 ml (2.887 mmol) of trifluoroacetic acid and stirred at RT overnight. The reaction mixture was then concentrated and the residue was purified by means of preparative HPLC (eluent gradient: acetonitrile/water 10:90→95:5 with addition of 0.1% TFA). This gave 234 mg (68% of theory) of the target compound.

$^1$H-NMR (400 MHz, DMSO-d$_6$): δ=12.95-11.82 (m, 2H), 8.95-8.89 (m, 2H), 8.37 (s, 1H), 8.23-8.19 (m, 6H), 7.97 (d, 2H), 7.61 (d, 2H), 7.48 (d, 2H), 7.13 (d, 2H), 5.41 (m, 1H), 4.46-4.24 (m, 8H), 3.84 (br. s, 2H), 2.45-2.33 (m, 4H), 2.08-1.90 (m, 4H), 1.33 (m, 6H).

LC-MS (method 7): R$_t$=1.59 min; MS (ESIpos): m/z=934 [M+H]$^+$.

Example 12

(2S)-3-{4-[2-Amino-6-({[2-(4-chlorophenyl)-1,3-oxazol-4-yl]methyl}sulfanyl)-3,5-dicyanopyridin-4-yl]phenoxy}propane-1,2-diyl (2S,2'S)-bis(2-{[(2S)-2-amino-3-(1H-imidazol-4-yl)propanoyl]amino}propanoate)bis(trifluoroacetic acid) salt

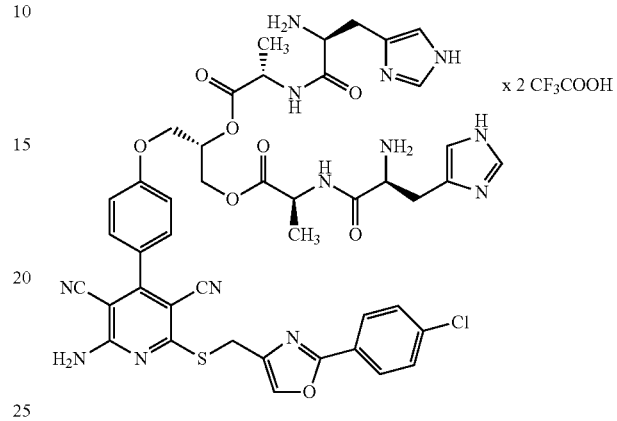

An amount of 275 mg (0.239 mmol) of the compound from example 26A was introduced in 2 ml of dichloromethane, admixed with 0.184 ml (2.390 mmol) of trifluoroacetic acid and stirred at RT for 3 hours. Subsequently the reaction mixture was concentrated and the residue was purified by means of preparative HPLC (eluent gradient: acetonitrile/water 10:90→95:5 with addition of 0.1% TFA). This gave 190 mg (66% of theory) of the target compound.

$^1$H-NMR (400 MHz, DMSO-d$_6$): δ=14.61-13.61 (m, 2H), 9.01-8.90 (m, 4H), 8.81-8.04 (m, 4H), 8.37 (s, 1H), 8.01 (d, 2H), 7.61 (d, 2H), 7.56 (d, 2H), 7.43 (s, 2H), 7.11 (d, 2H), 5.38 (m, 1H), 4.46-4.33 (m, 6H), 4.28 (m, 2H), 4.15 (m, 2H), 3.34-3.05 (m, 4H), 1.34 (m, 6H).

LC-MS (method 7): R$_t$=1.16 min; MS (ESIpos): m/z=950 [M+H]$^+$.

Example 13

(2S)-3-{4-[2-Amino-6-({[2-(4-chlorophenyl)-1,3-oxazol-4-yl]methyl}sulfanyl)-3,5-dicyanopyridin-4-yl]phenoxy}propane-1,2-diyl(2S,2'S)-bis(2-{[(methylamino)acetyl]amino}propanoate)bis(trifluoroacetic acid) salt

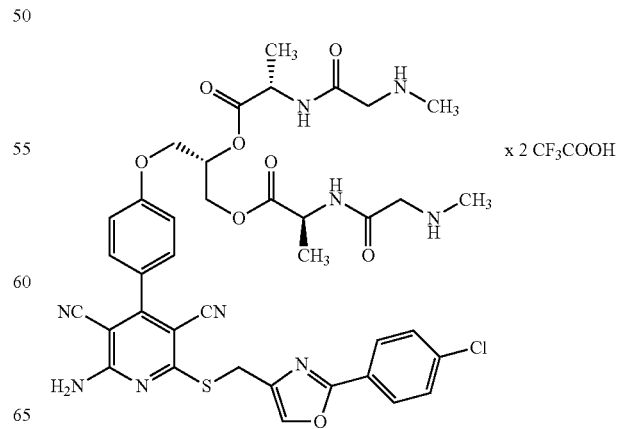

An amount of 134 mg (0.132 mmol) of the compound from example 21A was introduced in 2 ml of dichloromethane, admixed with 0.101 ml (1.316 mmol) of trifluoroacetic acid and stirred at RT for 2 hours. Subsequently the reaction mixture was concentrated and the residue was purified by means of preparative HPLC (eluent gradient: acetonitrile/water 10:90→95:5 with addition of 0.1% TFA). This gave 103 mg (72% of theory) of the target compound.

$^1$H-NMR (400 MHz, DMSO-$d_6$): δ=8.95 (d, 2H), 8.89-8.69 (m, 4H), 8.37 (s, 1H), 8.26-8.02 (br. s, 2H), 7.97 (d, 2H), 7.61 (d, 2H), 7.50 (d, 2H), 7.13 (d, 2H), 5.40 (m, 1H), 4.42-4.24 (m, 8H), 3.75 (s, 6H), 2.56 (m, 4H), 1.33 (m, 6H).

LC-MS (method 5): $R_t$=1.00 min; MS (ESIpos): m/z=818 μM+H]$^+$.

Example 14

(2S,6S,9S,13S,17S)-2,17-Diamino-9-({4-[2-amino-6-({[2-(4-chlorophenyl)-1,3-oxazol-4-yl]methyl}sulfanyl)-3,5-dicyanopyridin-4-yl]phenoxy}methyl)-6,13-dimethyl-4,7,12,15-tetraoxo-8,11-dioxa-5,14-diazaoctadecane-1,18-dioic acid bis(trifluoroacetic acid) salt

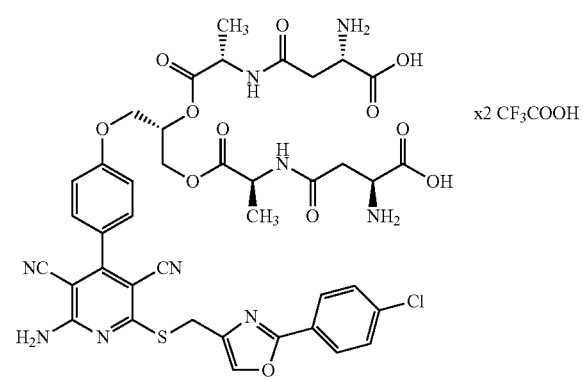 [SMILES: C[C@H](NC(=O)C[C@H](N)C(=O)O)C(=O)OC[C@H](COc1ccc(-c2c(C#N)c(N)nc(SCc3coc(-c4ccc(Cl)cc4)n3)c2C#N)cc1)OC(=O)[C@H](C)NC(=O)C[C@H](N)C(=O)O]

An amount of 190 mg (0.156 mmol) of the compound from example 22A was introduced in 1 ml of dichloromethane, admixed with 0.120 ml (1.559 mmol) of trifluoroacetic acid and stirred at RT overnight. The reaction mixture was then concentrated and the residue was purified by means of preparative HPLC (eluent gradient: acetonitrile/water 10:90→95:5 with addition of 0.1% TFA). This gave 76 mg (43% of theory) of the target compound.

$^1$H-NMR (400 MHz, DMSO-$d_6$): δ=14.20-13.53 (m, 2H), 8.69 (d, 2H), 8.37 (s, 1H), 8.26-8.02 (m, 6H), 7.97 (d, 2H), 7.61 (d, 2H), 7.49 (d, 2H), 7.12 (d, 2H), 5.36 (m, 1H), 4.45-4.18 (m, 10H), 2.81-2.72 (m, 4H), 1.30 (m, 6H).

LC-MS (method 6): $R_t$=1.00 min; MS (ESIpos): m/z=906 [M+H]$^+$.

Example 15

(2S,7S,10S,14S,19S)-2,19-Diamino-10-({4-[2-amino-6-({[2-(4-chlorophenyl)-1,3-oxazol-4-yl]methyl}sulfanyl)-3,5-dicyanopyridin-4-yl]phenoxy}methyl)-7,14-dimethyl-5,8,13,16-tetraoxo-9,12-dioxa-6,15-diazaicosane-1,20-dioic acid bis(trifluoroacetic acid) salt

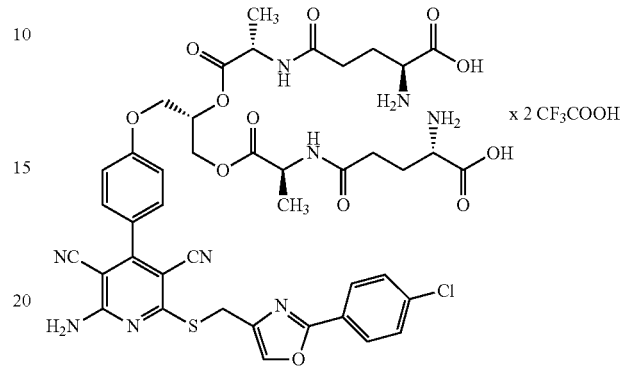

An amount of 120 mg (0.096 mmol) of the compound from example 27A was introduced in 1 ml of dichloromethane, admixed with 0.074 ml (0962 mmol) of trifluoroacetic acid and stirred at RT overnight. The reaction mixture was then concentrated and the residue was purified by means of preparative HPLC (eluent gradient: acetonitrile/water 10:90→95:5 with addition of 0.1% TFA). This gave 20 mg (18% of theory) of the target compound.

$^1$H-NMR (400 MHz, DMSO-$d_6$): δ=14.11-13.62 (m, 2H), 8.44 (d, 2H), 8.37 (s, 1H), 8.35-8.06 (m, 8H), 7.97 (d, 2H), 7.61 (d, 2H), 7.49 (d, 2H), 7.12 (d, 2H), 5.35 (m, 1H), 4.39-4.20 (m, 8H), 3.93 (br. s, 2H), 2.38-2.24 (m, 4H), 2.06-1.90 (m, 4H), 1.28 (m, 6H).

LC-MS (method 7): $R_t$=1.00 min; MS (ESIpos): m/z=934 [M+H]$^+$.

Example 16

(2S)-3-{4-[2-Amino-6-({[2-(4-chlorophenyl)-1,3-oxazol-4-yl]methyl}sulfanyl)-3,5-dicyanopyridin-4-yl]phenoxy}propane-1,2-diyl (2S,2'S)-bis(2-{[(2S)-pyrrolidin-2-ylcarbonyl]amino}propanoate) dihydrochloride

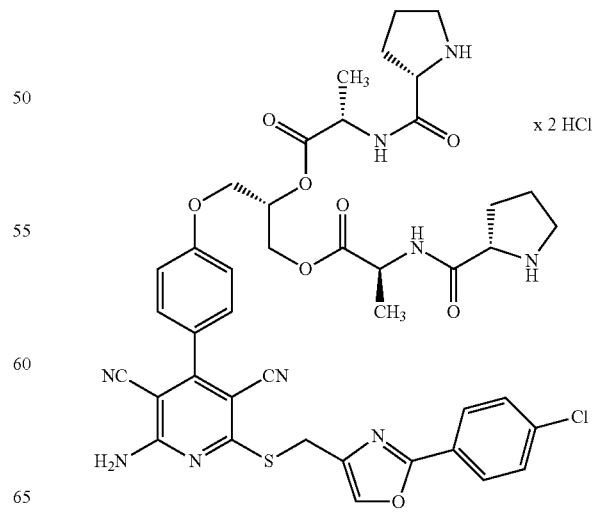

An amount of 339 mg (0.317 mmol) of the compound from example 20A was introduced in 4 ml of dichloromethane and admixed dropwise with 3.166 ml (6.333 mmol) of a 2M solution of hydrogen chloride in diethyl ether. It was subsequently stirred at RT overnight. The precipitated solid was isolated by filtration, washed with diethyl ether and dried under reduced pressure. This gave 277 mg (91% of theory) of the target compound.

$^1$H-NMR (400 MHz, DMSO-$d_6$): δ=9.73 (m, 2H), 9.04 (m, 2H), 8.54 (m, 2H), 8.38 (s, 1H), 8.31-8.03 (br. s, 2H), 7.96 (d, 2H), 7.60 (d, 2H), 7.49 (d, 2H), 7.11 (d, 2H), 5.37 (m, 1H), 4.41-4.17 (m, 10H), 3.20-3.16 (m, 4H), 2.29 (m, 2H), 1.86-1.80 (m, 6H), 1.34 (m, 6H).

LC-MS (method 5): $R_t$=0.96 min; MS (ESIpos): m/z=870 [M+H]$^+$.

Example 17

(2S)-3-{4-[2-Amino-6-({[2-(4-chlorophenyl)-1,3-oxazol-4-yl]methyl}sulfanyl)-3,5-dicyanopyridin-4-yl]phenoxy}propane-1,2-diyl(2S,2'S)-bis(2-{[(2S)-2-aminopropanoyl)amino}propanoate)bis(4-methylbenzenesulfonic acid) salt

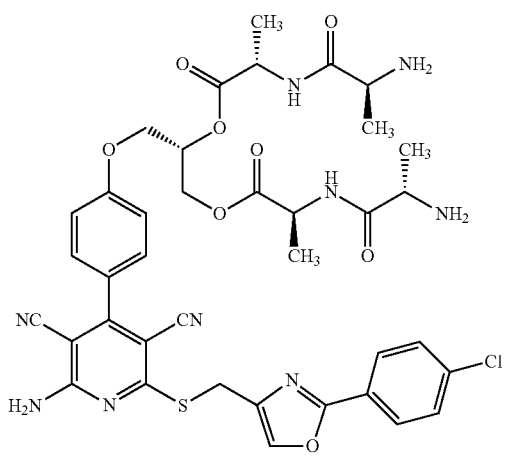

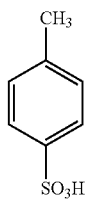

x 2

An amount of 220 mg (0.216 mmol) of the compound from example 48A was introduced in 20 ml of dichloromethane, admixed with 82 mg (0.475 mmol) of 4-methylbenzenesulfonic acid and stirred at 60° C. for 24 hours. The reaction mixture was then concentrated and the residue was purified by means of preparative HPLC (eluent gradient: acetonitrile/water 10:90→95:5 with addition of 0.1% 4-methylbenzenesulfonic acid). This gave 158 mg (57% of theory) of the target compound.

$^1$H-NMR (400 MHz, DMSO-$d_6$): δ=8.79-8.75 (m, 2H), 8.37 (s, 1H), 8.31-8.01 (m, 8H), 7.97 (d, 2H), 7.61 (d, 2H), 7.53-7.43 (m, 6H), 7.11 (d, 6H), 5.40-5.32 (m, 1H), 4.45-4.34 (m, 4H), 4.32-3.98 (m, 4H), 3.89-3.77 (m, 2H), 2.29 (s, 6H), 1.37-1.29 (m, 12H).

LC-MS (method 6): $R_t$=1.25 min; MS (ESIpos): m/z=818 [M+H]$^+$.

Example 18

(2S)-3-{4-[2-Amino-6-({[2-(4-chlorophenyl)-1,3-oxazol-4-yl]methyl}sulfanyl)-3,5-dicyanopyridin-4-yl]phenoxy}propane-1,2-diyl bis(3-{[(2S)-2,6-diaminohexanoyl]amino}propanoate)tetrakis(trifluoroacetic acid) salt

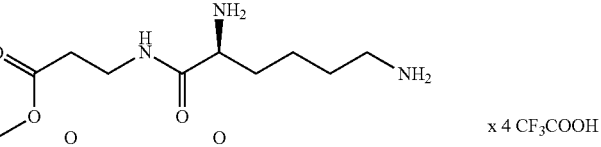

x 4 CF$_3$COOH

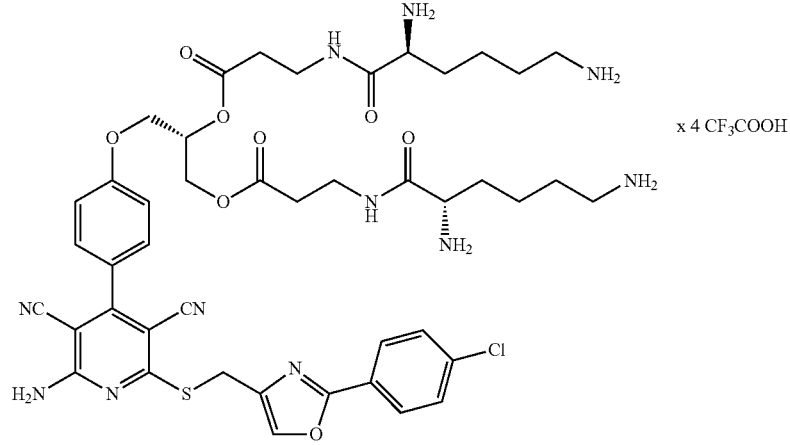 [SMILES: N#Cc1c(N)nc(SCc2coc(-c3ccc(Cl)cc3)n2)c(C#N)c1-c1ccc(OC[C@@H](COC(=O)CCNC(=O)[C@@H](N)CCCCN)OC(=O)CCNC(=O)[C@@H](N)CCCCN)cc1]

An amount of 70 mg (0.058 mmol) of the compound from example 31A was introduced in 0.5 ml of dichloromethane, admixed with 0.045 ml (0.578 mmol) of trifluoroacetic acid and stirred at RT. After 3 hours, again, the same amount of trifluoroacetic acid was added and the mixture was stirred at RT overnight. The reaction mixture was then concentrated and the residue was purified by means of preparative HPLC (eluent gradient: acetonitrile/water 10:90→95:5 with addition of 0.1% TFA). This gave 45 mg (55% of theory) of the target compound.

$^1$H-NMR (400 MHz, DMSO-$d_6$): δ=8.61-8.57 (m, 2H), 8.37 (s, 1H), 8.33-8.01 (m, 8H), 7.98 (d, 2H), 7.86-7.37 (m, 6H), 7.61 (d, 2H), 7.50 (d, 2H), 7.12 (d, 2H), 5.36 (m, 1H), 4.42 (s, 2H), 4.41-4.24 (m, 4H), 3.67 (m, 2H), 3.38 (m, 4H), 2.75 (m, 4H), 2.61-2.57 (m, 4H), 1.67 (m, 4H), 1.51 (m, 4H), 1.29 (m, 4H).

LC-MS (method 6): $R_t$=0.90 min; MS (ESIpos): m/z=932 [M+H]$^+$.

Example 19

(2S)-3-{4-[2-Amino-6-({[2-(4-chlorophenyl)-1,3-oxazol-4-yl]methyl}sulfanyl)-3,5-dicyanopyridin-4-yl]phenoxy}propane-1,2-diyl bis{3-[(aminoacetyl)amino]propanoate}bis(trifluoroacetic acid) salt

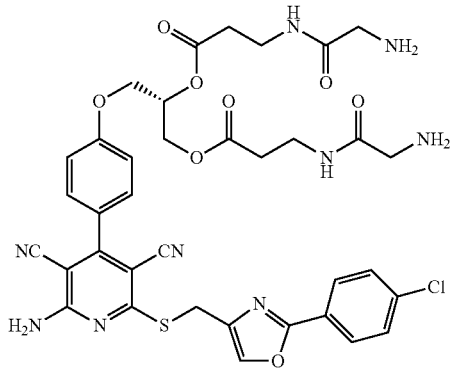

An amount of 79 mg (0.080 mmol) of the compound from example 32A was introduced in 0.5 ml of dichloromethane, admixed with 0.061 ml (0.798 mmol) of trifluoroacetic acid and stirred at RT. After 3 hours, again, the same amount of trifluoroacetic acid was added and the mixture was stirred at RT overnight. The reaction mixture was then concentrated and the residue was purified by means of preparative HPLC (eluent gradient: acetonitrile/water 10:90→95:5 with addition of 0.1% TFA). This gave 54 mg (65% of theory) of the target compound.

$^1$H-NMR (400 MHz, DMSO-$d_6$): δ=8.44 (m, 2H), 8.37 (s, 1H), 8.32-7.66 (br. m, 8H), 7.97 (d, 2H), 7.61 (d, 2H), 7.49 (d, 2H), 7.13 (d, 2H), 5.37 (m, 1H), 4.42 (s, 2H), 4.41-4.24 (m, 4H), 3.52 (m, 4H), 3.38 (m, 4H), 2.58-2.53 (m, 4H).

LC-MS (method 6): $R_t$=1.19 min; MS (ESIpos): m/z=790 [M+H]$^+$.

Example 20

(2S)-3-{4-[2-Amino-6-({[2-(4-chlorophenyl)-1,3-oxazol-4-yl]methyl}sulfanyl)-3,5-dicyanopyridin-4-yl]phenoxy}propane-1,2-diyl bis(3-{[(2S)-2-amino-4-methylpentanoyl]amino}propanoate)bis(trifluoroacetic acid) salt

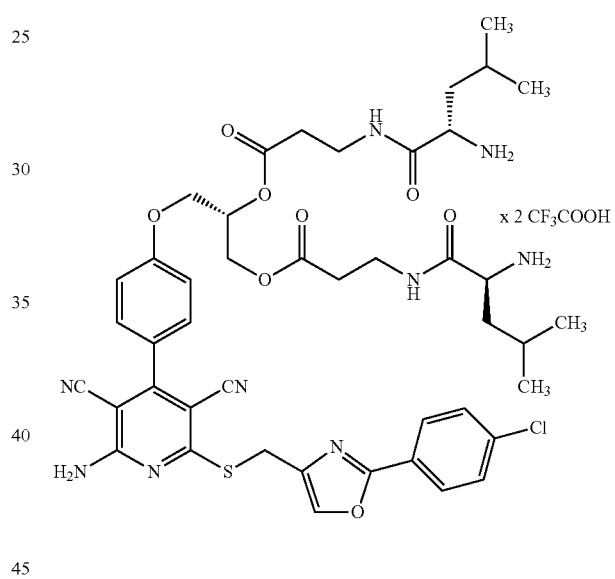

An amount of 85 mg (0.077 mmol) of the compound from example 33A was introduced in 0.5 ml of dichloromethane, admixed with 0.059 ml (0.771 mmol) of trifluoroacetic acid and stirred at RT overnight. The reaction mixture was then concentrated and the residue was purified by means of preparative HPLC (eluent gradient: acetonitrile/water 10:90→95:5 with addition of 0.1% TFA). This gave 47 mg (51% of theory) of the target compound.

$^1$H-NMR (400 MHz, DMSO-$d_6$): δ=8.60 (m, 2H), 8.37 (s, 1H), 8.18-8.04 (m, 6H), 7.97 (d, 2H), 7.61 (d, 2H), 7.49 (d, 2H), 7.12 (d, 2H), 5.35 (m, 1H), 4.42 (s, 2H), 4.41-4.24 (m, 4H), 3.67 (m, 2H), 3.45 (m, 2H), 3.29 (m, 2H), 2.59-2.54 (m, 4H), 1.64-1.45 (m, 6H), 0.89-0.84 (m, 12H).

LC-MS (method 6): $R_t$=1.31 min; MS (ESIpos): m/z=902 [M+H]$^+$.

Example 21

(2S)-3-{4-[2-Amino-6-({[2-(4-chlorophenyl)-1,3-oxazol-4-yl]methyl}sulfanyl)-3,5-dicyanopyridin-4-yl]phenoxy}propan-1,2-diyl bis(3-{[(2S)-2-amino-3-methylbutanoyl]amino}propanoate)bis(trifluoroacetic acid) salt

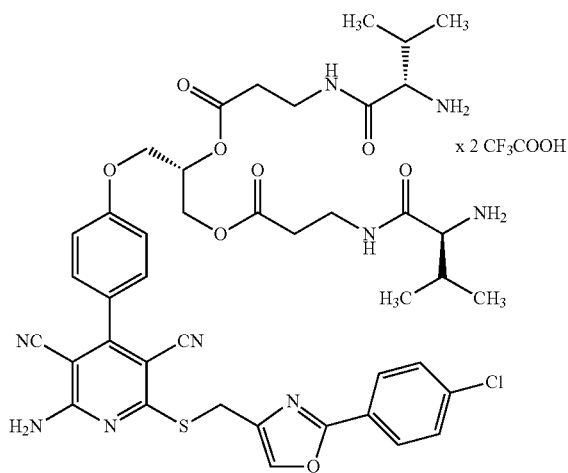 [SMILES: CC(C)[C@H](N)C(=O)NCCC(=O)OC[C@H](COc1ccc(-c2c(C#N)c(N)nc(SCc3coc(-c4ccc(Cl)cc4)n3)c2C#N)cc1)OC(=O)CCNC(=O)[C@@H](N)C(C)C]

An amount of 74 mg (0.070 mmol) of the compound from example 34A was introduced in 0.5 ml of dichloromethane, admixed with 0.054 ml (0.698 mmol) of trifluoroacetic acid and stirred at RT overnight. The reaction mixture was then concentrated and the residue was purified by means of preparative HPLC (eluent gradient: acetonitrile/water 10:90→95:5 with addition of 0.1% TFA). This gave 20 mg (26% of theory) of the target compound.

$^1$H-NMR (400 MHz, DMSO-$d_6$): δ=8.51 (dd, 2H), 8.36 (s, 1H), 8.33-8.01 (m, 6H), 7.97 (d, 2H), 7.61 (d, 2H), 7.49 (d, 2H), 7.11 (d, 2H), 5.35 (m, 1H), 4.42 (s, 2H), 4.39-4.23 (m, 4H), 3.50-3.39 (m, 4H), 3.26 (m, 2H), 2.59-2.54 (m, 4H), 1.99 (m, 2H), 0.90-0.84 (m, 12H).

LC-MS (method 6): $R_t$=1.31 min; MS (ESIpos): m/z=874 [M+H]$^+$.

Example 22

(2S)-3-{4-[2-Amino-6-({[2-(4-chlorophenyl)-1,3-oxazol-4-yl]methyl}sulfanyl)-3,5-dicyanopyridin-4-yl]phenoxy}propane-1,2-diyl(2S,2'S)-bis{2-[(3-aminopropanoyl)amino]-4-methylpentanoate}bis(trifluoroacetic acid) salt

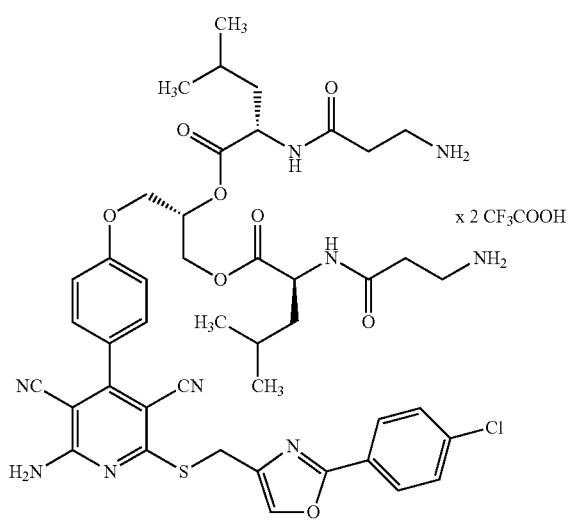 [SMILES: CC(C)C[C@H](NC(=O)CCN)C(=O)OC[C@H](COc1ccc(-c2c(C#N)c(N)nc(SCc3coc(-c4ccc(Cl)cc4)n3)c2C#N)cc1)OC(=O)[C@H](CC(C)C)NC(=O)CCN]

An amount of 240 mg (0.118 mmol) of the compound from example 37A was introduced in 1 ml of dichloromethane, admixed with 0.091 ml (1.175 mmol) of trifluoroacetic acid and stirred at RT. After 3 hours, again, the same amount of trifluoroacetic acid was added and the mixture was stirred at RT overnight. The reaction mixture was then concentrated and the residue was purified by means of preparative HPLC (eluent gradient: acetonitrile/water 10:90→95:5 with addition of 0.1% TFA). This gave 119 mg (88% of theory) of the target compound.

$^1$H-NMR (400 MHz, DMSO-$d_6$): δ=8.53 (m, 2H), 8.37 (s, 1H), 8.26-8.03 (m, 2H), 7.97 (d, 2H), 7.70 (br. m, 4H), 7.61 (d, 2H), 7.50 (d, 2H), 7.11 (d, 2H), 5.35 (m, 1H), 4.42 (s, 2H), 4.39-4.20 (m, 6H), 4.00-3.50 (m, 4H), 2.97 (m, 4H), 1.71-1.35 (m, 6H), 0.95-0.83 (m, 12H).

LC-MS (method 7): $R_t$=1.67 min; MS (ESIpos): m/z=902 [M+H]$^+$.

Example 23

(2S)-3-{4-[2-Amino-6-({[2-(4-chlorophenyl)-1,3-oxazol-4-yl]methyl}sulfanyl)-3,5-dicyanopyridin-4-yl]phenoxy}propane-1,2-diyl (2S,2'S)-bis{2-[(3-aminopropanoyl)amino]-3-methylbutanoate}bis(trifluoroacetic acid) salt

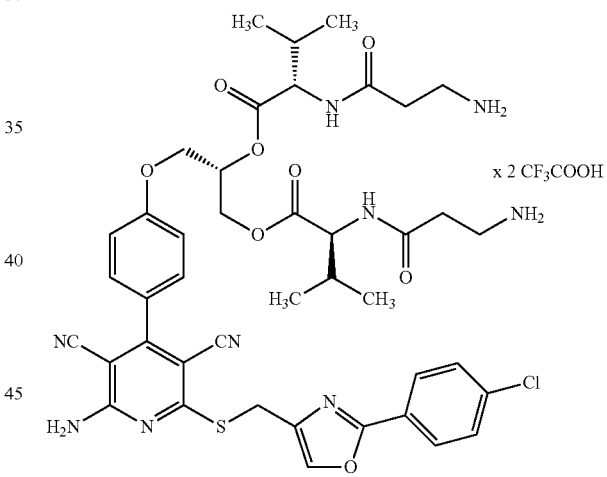

An amount of 216 mg (0.201 mmol) of the compound from example 40A was introduced in 1 ml of dichloromethane, admixed with 0.155 ml (2.010 mmol) of trifluoroacetic acid and stirred at RT. After 3 hours, again, the same amount of trifluoroacetic acid was added and the mixture was stirred at RT overnight. The reaction mixture was then concentrated and the residue was purified by means of preparative HPLC (eluent gradient: acetonitrile/water 10:90→95:5 with addition of 0.1% TFA). This gave 92 mg (42% of theory) of the target compound.

$^1$H-NMR (400 MHz, DMSO-$d_6$): δ=8.44 (br. d, 2H), 8.37 (s, 1H), 8.34-8.07 (m, 2H), 7.97 (d, 2H), 7.86-7.66 (m, 6H), 7.61 (d, 2H), 7.50 (d, 2H), 7.12 (d, 2H), 5.40-5.35 (m, 1H), 4.42 (s, 2H), 4.41-4.23 (m, 6H), 3.05-2.96 (m, 4H), 2.61-2.56 (m, 4H), 2.13-2.00 (m, 2H), 0.93-0.86 (m, 12H).

LC-MS (method 5): $R_t$=1.04 min; MS (ESIpos): m/z=874 [M+H]$^+$.

Example 24

(2S)-3-{4-[2-Amino-6-({[2-(4-chlorophenyl)-1,3-oxazol-4-yl]methyl}sulfanyl)-3,5-dicyanopyridin-4-yl]phenoxy}propane-1,2-diyl(2S,2'S)-bis(2-{[(2R)-2-aminopropanoyl]amino}propanoate) dihydrochloride

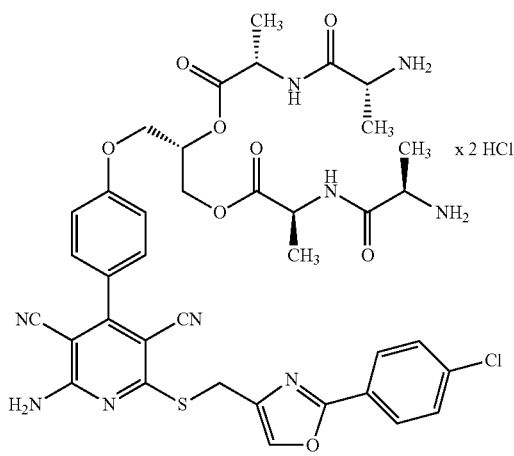 [SMILES: C[C@H](NC(=O)[C@@H](C)N)C(=O)OC[C@H](COc1ccc(-c2c(C#N)c(N)nc(SCc3coc(-c4ccc(Cl)cc4)n3)c2C#N)cc1)OC(=O)[C@H](C)NC(=O)[C@@H](C)N]

An amount of 315 mg (0.309 mmol) of the compound from example 41A was introduced in 5 ml of dichloromethane and admixed dropwise, with stirring, with 6.185 ml (6.185 mmol) of a 1M solution of hydrogen chloride in diethyl ether. It was subsequently stirred at RT overnight. The precipitated solid was isolated by filtration, washed first with dichloromethane and then with diethyl ether, and finally dried under reduced pressure. This gave 256 mg (93% of theory) of the target compound.

$^1$H-NMR (400 MHz, DMSO-$d_6$): δ=8.95 (m, 2H), 8.38 (s, 1H), 8.20 (br. m, 8H), 7.97 (d, 2H), 7.61 (d, 2H), 7.50 (d, 2H), 7.13 (d, 2H), 5.39 (m, 1H), 4.42 (s, 2H), 4.41-4.24 (m, 6H), 3.87 (m, 2H), 1.39-1.30 (m, 12H).

LC-MS (method 8): $R_t$=0.85 min; MS (ESIpos): m/z=818 [M+H]$^+$.

Example 25

(2S)-3-{4-[2-Amino-6-({[2-(4-chlorophenyl)-1,3-oxazol-4-yl]methyl}sulfanyl)-3,5-dicyanopyridin-4-yl]phenoxy}propane-1,2-diyl(2R,2'R)-bis(2-{[(2R)-2-aminopropanoyl]amino}propanoate) dihydrochloride

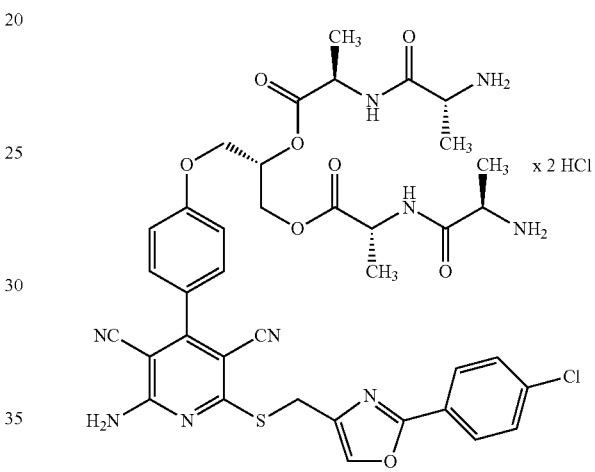

An amount of 435 mg (0.427 mmol) of the compound from example 44A was introduced in 8 ml of dichloromethane and admixed dropwise, with stirring, with 8.542 ml (8.542 mmol) of a 1M solution of hydrogen chloride in diethyl ether. It was subsequently stirred at RT for 6 hours. The precipitated solid was isolated by filtration, washed first with dichloromethane and then with diethyl ether, and finally dried under reduced pressure. This gave 348 mg (92% of theory) of the target compound.

$^1$H-NMR (400 MHz, DMSO-$d_6$): δ=8.95 (d, 2H), 8.38 (s, 1H), 8.34-8.02 (br. m, 8H), 7.97 (d, 2H), 7.61 (d, 2H), 7.49 (d, 2H), 7.11 (d, 2H), 5.38 (m, 1H), 4.47-4.22 (m, 8H), 3.86 (m, 2H), 1.39-1.30 (m, 12H).

LC-MS (method 8): $R_t$=0.88 min; MS (ESIpos): m/z=818 [M+H]$^+$.

Example 26

(2S)-3-{4-[2-Amino-6-({[2-(4-chlorophenyl)-1,3-oxazol-4-yl]methyl}sulfanyl)-3,5-dicyanopyridin-4-yl]phenoxy}propane-1,2-diyl (2S,2'S)-bis(2-{[(2S)-2-amino-3-methylbutanoyl]amino}propanoate) dihydrochloride

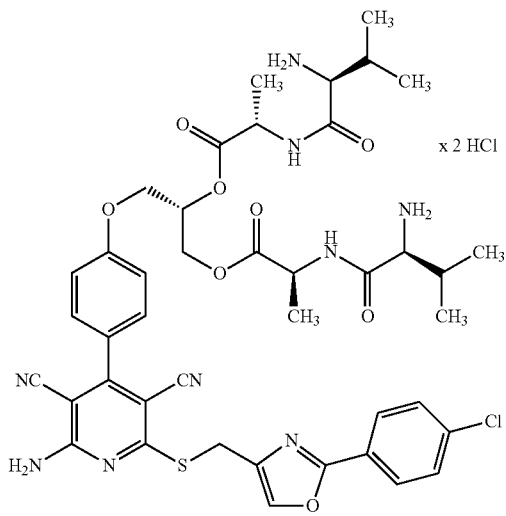 [SMILES: CC(C)[C@H](N)C(=O)N[C@@H](C)C(=O)OC[C@H](COc1ccc(-c2c(C#N)c(N)nc(SCc3coc(-c4ccc(Cl)cc4)n3)c2C#N)cc1)OC(=O)[C@H](C)NC(=O)[C@@H](N)C(C)C]

An amount of 240 mg (0.223 mmol) of the compound from example 45A was dissolved in 250 ml of dichloromethane. Hydrogen chloride gas was passed into this solution. After one hour of stirring at RT, the solution was concentrated under reduced pressure to a volume of approximately 50 ml and was admixed with 200 ml of ethyl acetate. The precipitated solid was isolated by suction filtration, washed with ethyl acetate and dried under a high vacuum. This gave 175 mg (83% of theory) of the target compound.

$^1$H-NMR (400 MHz, DMSO-d$_6$): δ=8.95 (d, 2H), 8.4 (s, 1H), 8.3-8.1 (m, 6H), 7.97 (d, 2H), 7.61 (d, 2H), 7.49 (d, 2H), 7.10 (d, 2H), 5.40 (m, 1H), 4.4-4.2 (m, 8H), 3.64 (m, 2H), 2.1 (m, 2H), 1.4-1.3 (2d, 6H), 0.95 (d, 12H).

LC-MS (method 6): R$_t$=1.22 min; MS (ESIpos): m/z=874 [M+H]$^+$.

Example 27

(2S)-3-{4-[2-Amino-6-({[2-(4-chlorophenyl)-1,3-oxazol-4-yl]methyl}sulfanyl)-3,5-dicyanopyridin-4-yl]phenoxy}propane-1,2-diyl (2S,2'S)-bis{2-[(aminoacetyl)amino]-3-methylbutanoate} dihydrochloride

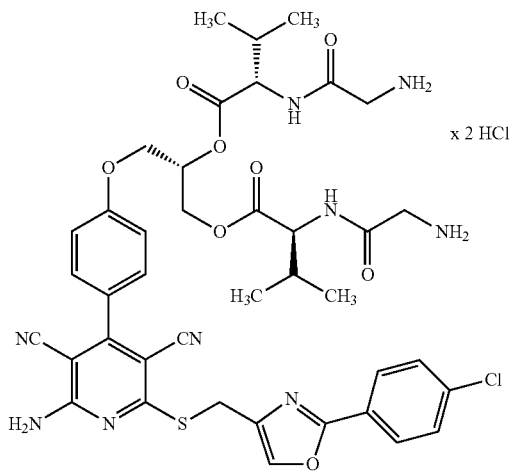 [SMILES: CC(C)[C@H](NC(=O)CN)C(=O)OC[C@H](COc1ccc(-c2c(C#N)c(N)nc(SCc3coc(-c4ccc(Cl)cc4)n3)c2C#N)cc1)OC(=O)[C@@H](NC(=O)CN)C(C)C]

An amount of 55 mg (0.312 mmol) of N-(tert-butoxycarbonyl)glycine was introduced in 2 ml of DMF and admixed with 57.5 mg (0.3 mmol) of 1-(3-dimethylaminopropyl)-3-ethylcarbodiimide hydrochloride and 51 mg (0.375 mmol) of 1-hydroxy-1H-benzotriazole hydrate. After 30 minutes of stirring at RT, 120 mg (0.125 mmol) of the compound from example 39A and 0.044 ml (0.25 mmol) of N,N-diisopropylethylamine were added. The mixture was subsequently stirred at RT overnight. Thereafter the batch was concentrated under reduced pressure and the residue was taken up in 50 ml of dichloromethane. It was washed in each case four times with 10 ml of 0.5M citric acid solution and 10 ml of 10% strength sodium hydrogencarbonate solution, and the organic phase was dried over magnesium sulfate and then concentrated. The residue was purified by preparative HPLC. Drying of the product fraction under a high vacuum left 90 mg (69% of theory) of the Boc-protected intermediate, which was immediately reacted further.

An amount of 90 mg (0.086 mmol) of the resultant intermediate was taken up in 50 ml of dichloromethane, and hydrogen chloride gas was passed into this solution. After one hour of stirring at RT, the solution was concentrated under reduced pressure to a volume of approximately 25 ml and was admixed with dethyl ether. The precipitated solid was isolated by suction filtration, washed with dichloromethane and diethyl ether and dried under a high vacuum. This gave 51 mg (65% of theory) of the target compound.

$^1$H-NMR (400 MHz, DMSO-d$_6$): δ=8.75 (d, 2H), 8.39 (s, 1H), 8.25-8.10 (m, 6H), 7.97 (d, 2H), 7.61 (d, 2H), 7.49 (d, 2H), 7.12 (d, 2H), 5.40-5.35 (m, 1H), 4.40-4.25 (m, 8H), 3.75-3.55 (m, 4H), 2.15-2.05 (m, 2H), 0.93 (d, 6H), 0.88 (d, 3H), 0.86 (d, 3H).

LC-MS (method 10): R$_t$=1.86 min; MS (ESIpos): m/z=846 [M+H]$^+$.

Example 28

(2S)-3-{4-[2-Amino-6-({[2-(4-chlorophenyl)-1,3-oxazol-4-yl]methyl}sulfanyl)-3,5-dicyanopyridin-4-yl]phenoxy}propane-1,2-diyl(2S,2'S)-bis(2-{[(2S)-2-aminopropanoyl]amino}-3-methylbutanoate) dihydrochloride

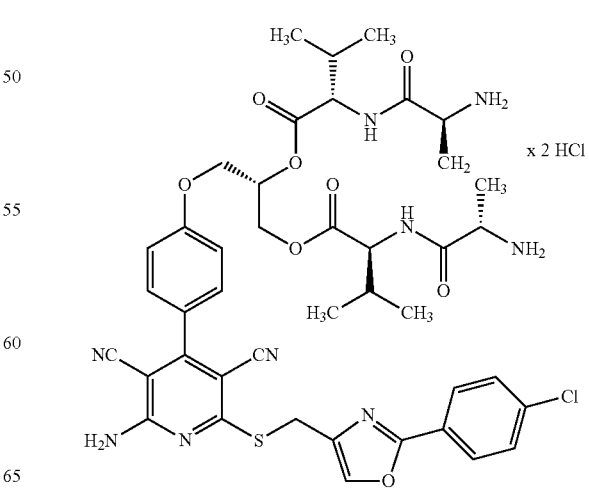

The title compound was prepared in the same way as for the preparation of example 27, starting from the compound from example 39A and commercial N-(tert-butoxycarbonyl)-L-alanine.

Yield: 37% of theory $^1$H-NMR (400 MHz, DMSO-d$_6$): δ=8.7 (d, 2H), 8.4 (s, 1H), 8.30-8.15 (m, 6H), 7.97 (d, 2H), 7.63 (d, 2H), 7.5 (d, 2H), 7.1 (d, 2H), 5.45-5.35 (m, 1H), 4.45-4.20 (m, 8H), 4.05-3.90 (m, 2H), 2.15-2.05 (m, 2H), 1.35 (d, 6H), 0.94 (d, 6H), 0.91 (d, 3H), 0.89 (d, 3H).

LC-MS (method 7): R$_t$=1.56 min; MS (ESIpos): m/z=874 [M+H]$^+$.

Example 29

(2S)-3-{4-[2-Amino-6-({[2-(4-chlorophenyl)-1,3-oxazol-4-yl]methyl}sulfanyl)-3,5-dicyanopyridin-4-yl]phenoxy}propane-1,2-diyl(2S,2'S)-bis(2-{[aminoacetyl]amino}-4-methylpentanoate) dihydrochloride

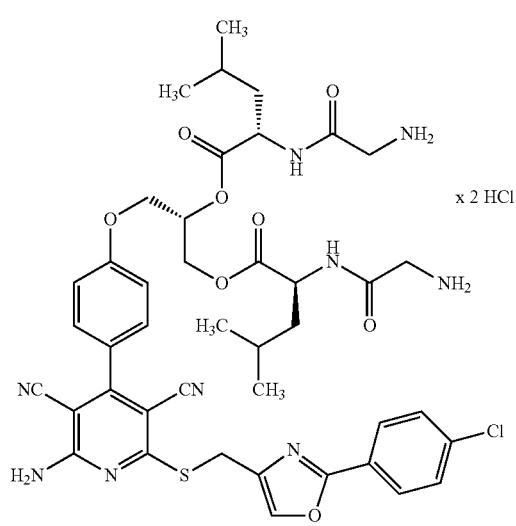 [SMILES: CC(C)C[C@H](NC(=O)CN)C(=O)OC[C@H](COc1ccc(-c2c(C#N)c(N)nc(SCc3coc(-c4ccc(Cl)cc4)n3)c2C#N)cc1)OC(=O)[C@H](CC(C)C)NC(=O)CN]

The title compound was prepared in the same way as for the preparation of example 27, starting from the compound from example 36A and commercial N-(tert-butoxycarbonyl)glycine.

Yield: 54% of theory $^1$H-NMR (400 MHz, DMSO-d$_6$): δ=8.9 (m, 2H), 8.39 (s, 1H), 8.2-8.1 (m, 6H), 7.97 (d, 2H), 7.61 (d, 2H), 7.50 (d, 2H), 7.13 (d, 2H), 5.40-5.35 (m, 1H), 4.45-4.20 (m, 8H), 3.70-3.55 (m, 4H), 1.75-1.45 (m, 6H), 0.92 (d, 3H), 0.90 (d, 3H), 0.87 (d, 3H), 0.85 (d, 3H).

LC-MS (method 7): R$_t$=1.64 min; MS (ESIpos): m/z=874 [M+H]$^+$.

Example 30

(2S)-3-{4-[2-Amino-6-({[2-(4-chlorophenyl)-1,3-oxazol-4-yl]methyl}sulfanyl)-3,5-dicyanopyridin-4-yl]phenoxy}propane-1,2-diyl (2S,2'S)-bis(2-{[(2S)-2-aminopropanoyl]amino}-4-methylpentanoate) dihydrochloride

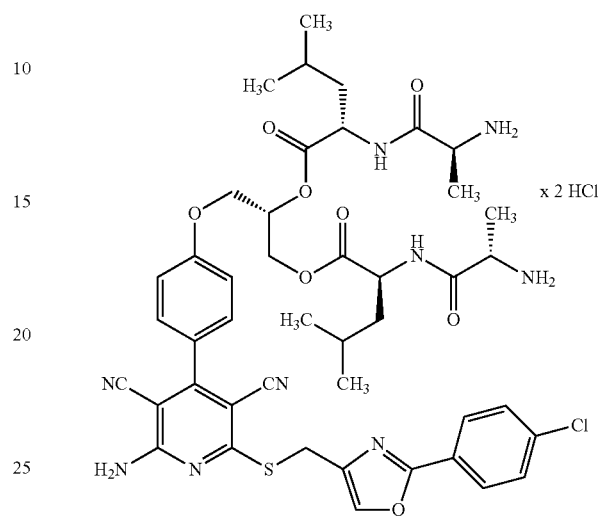

The title compound was prepared in the same way as for the preparation of example 27, starting from the compound from example 36A and commercial N-(tert-butoxycarbonyl)-L-alanine.

Yield: 54% of theory $^1$H-NMR (400 MHz, DMSO-d$_6$): δ=8.9 (m, 2H), 8.39 (s, 1H), 8.30-8.15 (m, 4H), 7.97 (d, 2H), 7.6 (d, 2H), 7.50 (d, 2H), 7.1 (d, 2H), 5.40-5.30 (m, 1H), 4.45-4.20 (m, 8H), 3.9 (br. m, 2H), 1.75-1.50 (m, 6H), 1.37 (d, 6H), 0.92 (d, 3H), 0.90 (d, 3H), 0.87 (d, 3H), 0.06 (d, 3H).

LC-MS (method 6): R$_t$=1.37 min; MS (ESIpos): m/z=902 [M+H]$^+$.

Example 31

(2S)-3-{4-[2-Amino-6-({[2-(4-chlorophenyl)-1,3-oxazol-4-yl]methyl}sulfanyl)-3,5-dicyanopyridin-4-yl]phenoxy}propane-1,2-diyl bis(3-{[(2S)-2-aminopropanoyl)amino}propanoate)dihydrochloride

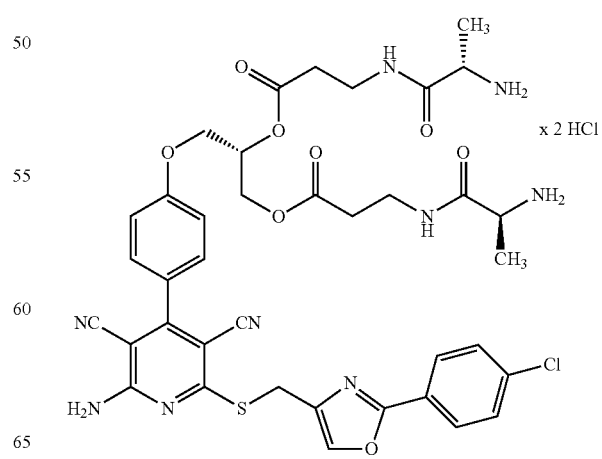

An amount of 200 mg (0.196 mmol) of the compound from example 46A was introduced in 60 ml of dichloromethane, and hydrogen chloride gas was passed into this solution. After one hour of stirring at RT, the solution was concentrated under reduced pressure to a volume of approximately 30 ml and was admixed with 50 ml of ethyl acetate. The precipitated solid was isolated by suction filtration, washed with ethyl acetate and dried under a high vacuum at 100° C. for 5 hours. This gave 151 mg (86% of theory) of the target compound.

LC-MS (method 6): $R_t$=1.16 min; MS (ESIpos): m/z=818 [M+H]$^+$.

Example 32

(2S)-3-{4-[2-Amino-6-({[2-(4-chlorophenyl)-1,3-oxazol-4-yl]methyl}sulfanyl)-3,5-dicyanopyridin-4-yl]phenoxy}propane-1,2-diyl (2S,2'S)-bis{2-[(3-aminopropanoyl)amino]propanoate}dihydrochloride

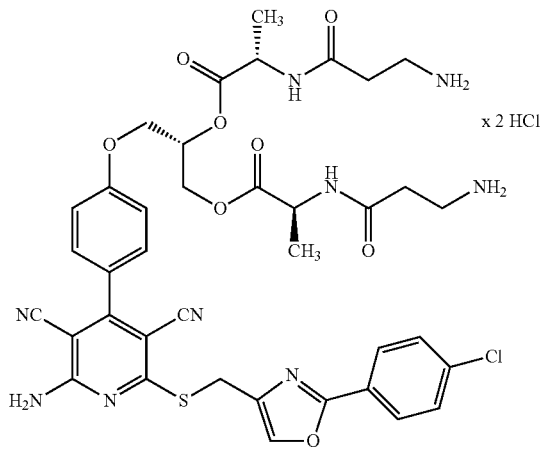 [SMILES: C[C@H](NC(=O)CCN)C(=O)OC[C@H](COc1ccc(-c2c(C#N)c(N)nc(SCc3coc(-c4ccc(Cl)cc4)n3)c2C#N)cc1)OC(=O)[C@H](C)NC(=O)CCN]

An amount of 3740 mg (3.672 mmol) of the compound from example 47A was introduced in 800 ml of dichloromethane, and hydrogen chloride gas was passed into this solution. After one hour of stirring at RT, the solution was concentrated under reduced pressure to a volume of approximately 100 ml, admixed with 100 ml of ethyl acetate and stirred at RT for 10 minutes. The precipitated solid was isolated by suction filtration, washed three times with diethyl ether and then dried under a high vacuum at 90° C. for 20 hours. This gave 3290 mg (quantitative) of the target compound.

$^1$H-NMR (400 MHz, DMSO-d$_6$): δ=8.64 (d, 2H), 8.4 (s, 1H), 8.05-7.90 (m, 8H), 7.63 (d, 2H), 7.50 (d, 2H), 7.13 (d, 2H), 5.40-5.30 (m, 1H), 4.43 (s, 2H), 4.4-4.2 (m, 6H), 3.0-2.9 (m, 4H), 2.55 (m, 4H), 1.3 (t, 6H).

LC-MS (method 6): $R_t$=1.15 min; MS (ESIpos): m/z=818 [M+H]$^+$.

Example 33

(2S)-3-{4-[2-Amino-6-({[2-(4-chlorophenyl)-1,3-oxazol-4-yl]methyl}sulfanyl)-3,5-dicyanopyridin-4-yl]phenoxy}propane-1,2-diyl(2S,2'S)-bis(2-{[(2S)-2-aminopropanoyl]amino}propanoate)dihydrochloride

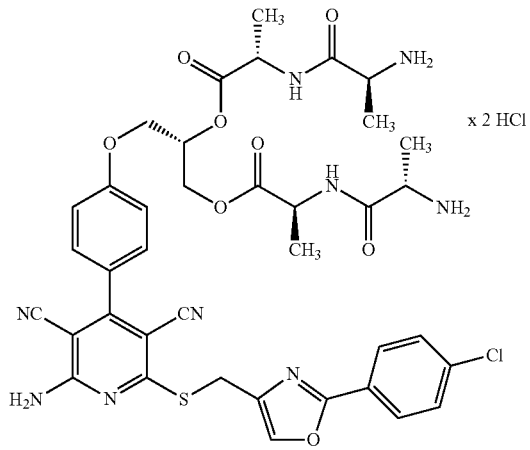 [SMILES: C[C@H](N)C(=O)N[C@@H](C)C(=O)OC[C@H](COc1ccc(-c2c(C#N)c(N)nc(SCc3coc(-c4ccc(Cl)cc4)n3)c2C#N)cc1)OC(=O)[C@H](C)NC(=O)[C@H](C)N]

An amount of 2484 mg (2.439 mmol) of the compound from example 48A was taken up in 300 ml of dichloromethane, and hydrogen chloride gas was passed into this solution. After one hour of stirring at RT, the solution was concentrated under reduced pressure to a volume of approximately 250 ml, admixed with 250 ml of ethyl acetate and stirred at RT for 10 minutes. The precipitated solid was isolated by suction filtration, washed three times with ethyl acetate and then dried under a high vacuum at 100° C. for 18 hours. This gave 2110 mg (97% of theory) of the target compound.

$^1$H-NMR (400 MHz, DMSO-d$_6$): δ=8.95 (m, 2H), 8.4 (s, 1H), 8.25-8.15 (m, 6H), 7.97 (d, 2H), 7.6 (d, 2H), 7.50 (d, 2H), 7.13 (d, 2H), 5.40-5.30 (m, 1H), 4.42 (s, 2H), 4.4-4.2 (m, 6H), 4.3-4.2 (m, 2H), 1.4-1.3 (m, 12H).

LC-MS (method 6): $R_t$=1.18 min; MS (ESIpos): m/z=818 [M+H]$^+$.

Example 34

(2R)-3-{4-[2-Amino-6-({[2-(4-chlorophenyl)-1,3-oxazol-4-yl]methyl}sulfanyl)-3,5-dicyanopyridin-4-yl]phenoxy}propane-1,2-diyl(2S,2'S)-bis(2-{[(2S)-2,6-diaminohexanoyl]amino}propanoate) tetrahydrochloride

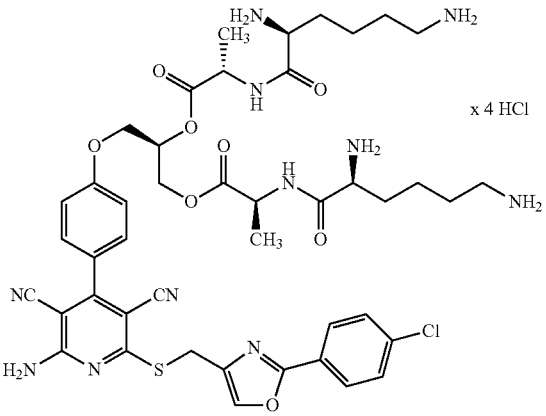 [SMILES: C[C@H](NC(=O)[C@@H](N)CCCCN)C(=O)OC[C@@H](COc1ccc(-c2c(C#N)c(N)nc(SCc3coc(-c4ccc(Cl)cc4)n3)c2C#N)cc1)OC(=O)[C@H](C)NC(=O)[C@@H](N)CCCCN]

An amount of 297 mg (0.22 mmol) of the compound from example 51A was introduced in 2.1 ml of dichloromethane and admixed dropwise with 2.2 ml (4.45 mmol) of a 2M solution of hydrogen chloride in diethyl ether. The mixture was stirred at room temperature for four hours and then concentrated under reduced pressure. The residue was admixed with 5 ml of acetonitrile and the mixture was subsequently concentrated again. This procedure was repeated once more. Drying of the residue under reduced pressure gave 230 mg (96% of theory) of the target compound.

$^1$H-NMR (400 MHz, DMSO-d$_6$): δ=9.13 (dd, 2H), 8.41-8.26 (m, 5H), 8.12-7.89 (m, 6H), 7.62 (d, 2H), 7.49 (d, 2H), 7.12 (d, 2H), 5.42-5.36 (m, 1H), 4.49-4.22 (m, 8H), 3.89-3.78 (m, 2H), 2.81-2.69 (m, 4H), 1.82-1.71 (m, 4H), 1.65-1.53 (m, 4H), 1.49-1.30 (m, 10H).

LC-MS (method 6): R$_t$=0.91 min; MS (ESIpos): m/z=932 [M+H]$^+$.

Example 35

(2S)-3-{4-[2-Amino-6-({[2-(4-chlorophenyl)-1,3-oxazol-4-yl]methyl}sulfanyl)-3,5-dicyanopyridin-4-yl]phenoxy}propane-1,2-diyl(2S,2'S)-bis(2-{[(2S)-2,6-diaminohexanoyl)amino}propanoate) tetrahydrochloride

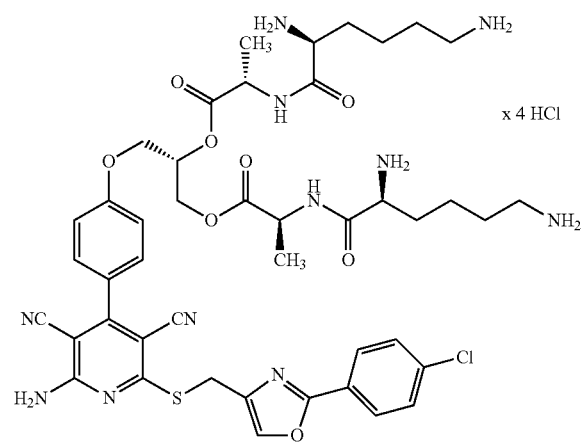 [SMILES: C[C@H](NC(=O)[C@@H](N)CCCCN)C(=O)OC[C@H](COc1ccc(-c2c(C#N)c(N)nc(SCc3coc(-c4ccc(Cl)cc4)n3)c2C#N)cc1)OC(=O)[C@H](C)NC(=O)[C@@H](N)CCCCN]

An amount of 325 mg (0.24 mmol) of the compound from example 52A was introduced in 2.3 ml of dichloromethane and admixed dropwise with 2.4 ml (4.89 mmol) of a 2M solution of hydrogen chloride in diethyl ether. The mixture was stirred at room temperature for 4 hours and then concentrated under reduced pressure. The residue was admixed with 5 ml of acetonitrile and the mixture was subsequently concentrated again. This procedure was repeated once more. Drying of the residue under reduced pressure gave 250 mg (95% of theory) of the target compound.

$^1$H-NMR (400 MHz, DMSO-d$_6$): δ=9.13 (t, 2H), 8.41-8.26 (m, 5H), 8.12-7.89 (m, 6H), 7.62 (d, 2H), 7.49 (d, 2H), 7.12 (d, 2H), 5.42-5.36 (m, 1H), 4.49-4.22 (m, 8H), 3.89-3.78 (m, 2H), 2.81-2.69 (m, 4H), 1.82-1.71 (m, 4H), 1.65-1.53 (m, 4H), 1.49-1.30 (m, 10H).

LC-MS (method 5): R$_t$=0.79 min; MS (ESIpos): m/z=932 [M+H]$^+$.

Example 36

(2S)-3-{4-[2-Amino-6-({[2-(4-chlorophenyl)-1,3-oxazol-4-yl]methyl}sulfanyl)-3,5-dicyanopyridin-4-yl]phenoxy}propane-1,2-diyl (2S,3R,2'S,3'R)-bis{2-[(aminoacetyl)amino]-3-hydroxybutanoate}bis (trifluoroacetic acid) salt

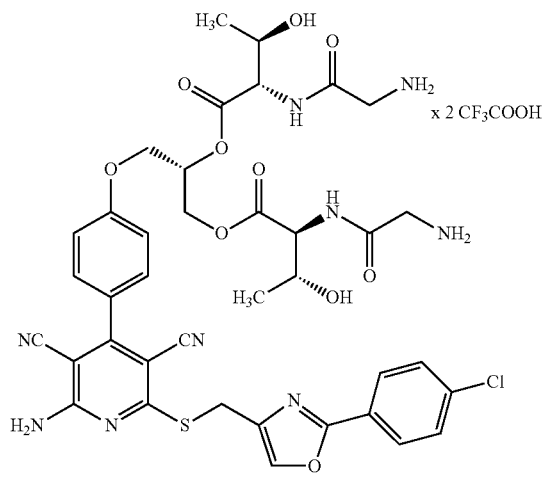 [SMILES: C[C@@H](O)[C@H](NC(=O)CN)C(=O)OC[C@H](COc1ccc(-c2c(C#N)c(N)nc(SCc3coc(-c4ccc(Cl)cc4)n3)c2C#N)cc1)OC(=O)[C@@H](NC(=O)CN)[C@@H](C)O]

An amount of 92 mg (0.09 mmol) of the compound from example 55A was introduced in 2.0 ml of dichloromethane and admixed dropwise with 0.27 ml (3.50 mmol) of trifluoroacetic acid. The mixture was stirred at room temperature overnight and then concentrated under reduced pressure. The residue was purified by means of preparative HPLC (eluent: acetonitrile/water+0.1% TFA). This gave 67 mg (70% of theory) of the target compound.

$^1$H-NMR (400 MHz, DMSO-d$_6$): δ=8.68 (d, 2H), 8.38 (s, 1H), 8.30-7.91 (m, 8H), 7.62 (d, 2H), 7.49 (d, 2H), 7.11 (d, 2H), 5.39 (quint, 1H), 5.32-5.12 (br. s, 1H), 4.50-4.15 (m, 11H), 3.78-3.58 (m, 4H), 1.11 (dd, 6H).

LC-MS (method 5): R$_t$=0.96 min; MS (ESIpos): m/z=850 [M+H]$^+$.

Example 37

(2S)-3-{4-[2-Amino-6-({[2-(4-chlorophenyl)-1,3-oxazol-4-yl]methyl}sulfanyl)-3,5-dicyanopyridin-4-yl]phenoxy}propane-1,2-diyl (2S,3R,2'S,3'R)-bis{2-[(aminoacetyl)amino]-3-hydroxybutanoate}dihydrochloride

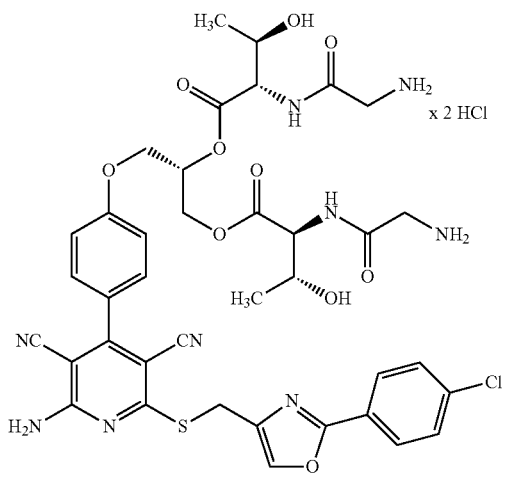 [SMILES: C[C@@H](O)[C@H](NC(=O)CN)C(=O)OC[C@H](COc1ccc(-c2c(C#N)c(N)nc(SCc3coc(-c4ccc(Cl)cc4)n3)c2C#N)cc1)OC(=O)[C@@H](NC(=O)CN)[C@@H](C)O]

An amount of 190 mg (0.18 mmol) of the compound from example 55A was introduced in 2.5 ml of THF and admixed dropwise with 1.8 ml of a 2M solution of hydrogen chloride and diethyl ether. The mixture was stirred at room temperature overnight and then concentrated under reduced pressure. The residue was purified by means of preparative HPLC (eluent: acetonitrile/water+0.15% hydrochloric acid). This gave 123 mg (64% of theory) of the target compound.

$^1$H-NMR (400 MHz, DMSO-$d_6$): δ=8.72 (dd, 2H), 8.38 (s, 1H), 8.30-8.00 (m, 6H), 7.97 (d, 2H), 7.62 (d, 2H), 7.49 (d, 2H), 7.11 (d, 2H), 5.39 (quint, 1H), 5.32-5.12 (br. s, 1H), 4.50-4.15 (m, 11H), 3.78-3.58 (m, 4H), 1.11 (dd, 6H).

LC-MS (method 5): $R_t$=0.92 min; MS (ESIpos): m/z=850 [M+H]$^+$.

Example 38

(2S)-3-{4-[2-Amino-6-({[2-(4-chlorophenyl)-1,3-oxazol-4-yl]methyl}sulfanyl)-3,5-dicyanopyridin-4-yl]phenoxy}propane-1,2-diyl (2S,3R,2'S,3'R)-bis(2-{[(2S)-2-aminopropanoyl]amino}-3-hydroxybutanoate)bis(trifluoroacetic acid) salt

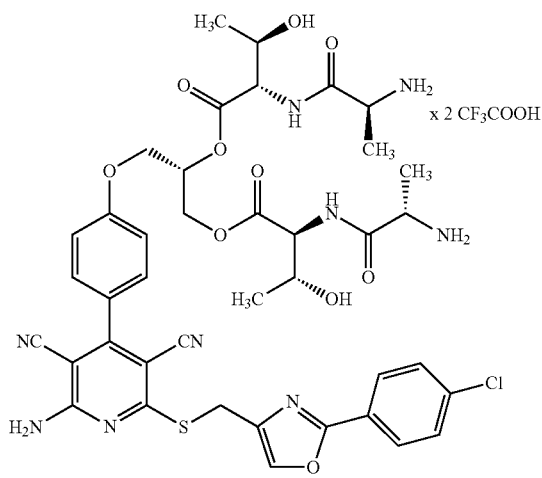 [SMILES: C[C@H](N)C(=O)N[C@H](C(=O)OC[C@H](COc1ccc(-c2c(C#N)c(N)nc(SCc3coc(-c4ccc(Cl)cc4)n3)c2C#N)cc1)OC(=O)[C@@H](NC(=O)[C@H](C)N)[C@@H](C)O)[C@@H](C)O]

An amount of 188 mg (0.17 mmol) of the compound from example 56A was introduced in 5 ml of dichloromethane and admixed dropwise with 0.54 ml (6.97 mmol) of trifluoroacetic acid. The mixture was stirred at room temperature overnight and then concentrated under reduced pressure. The residue was purified by means of preparative HPLC (eluent: acetonitrile/water+0.1% TFA). This gave 162 mg (84% of theory) of the target compound.

$^1$H-NMR (400 MHz, DMSO-$d_6$): δ=8.68 (d, 2H), 8.38 (s, 1H), 8.30-8.00 (m, 6H), 7.97 (d, 2H), 7.62 (d, 2H), 7.49 (d, 2H), 7.11 (d, 2H), 5.39 (quint, 1H), 5.32-5.12 (br. s, 1H), 4.45-4.18 (m, 11H), 4.09-3.98 (m, 2H), 1.39 (t, 6H), 1.12 (dd, 6H).

LC-MS (method 6): $R_t$=1.17 min; MS (ESIpos): m/z=878 [M+H]$^+$.

Example 39

(2S)-3-{4-[2-Amino-6-({[2-(4-chlorophenyl)-1,3-oxazol-4-yl]methyl}sulfanyl)-3,5-dicyanopyridin-4-yl]phenoxy}propane-1,2-diyl bis(3-{[(2S,3R)-2-amino-3-hydroxybutanoyl]amino}propanoate)bis(trifluoroacetic acid) salt

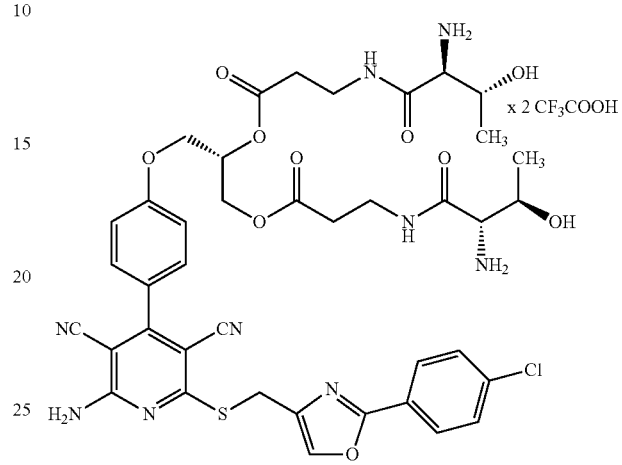

An amount of 106 mg (0.09 mmol) of the compound from example 57A was introduced in 2.5 ml of dichloromethane and admixed dropwise with 0.27 ml (3.56 mmol) of trifluoroacetic acid. The mixture was stirred at room temperature overnight and then concentrated under reduced pressure. The residue was purified by means of preparative HPLC (eluent: acetonitrile/water+0.1% TFA). This was followed by a further purification by preparative HPLC [column: Waters Sunfire C18, 5 μm, 250×20 mm; eluent: acetonitrile/0.2% strength aqueous TFA (50:50); flow rate: 25 ml/min; temperature 30° C.]. The product obtained in this way was stirred up with 2.5 ml of cold acetonitrile, and the solid was isolated by filtration and dried under a high vacuum. This gave 20 mg (21% of theory) of the target compound.

$^1$H-NMR (400 MHz, DMSO-$d_6$): δ=8.60-8.51 (m, 2H), 8.38 (s, 1H), 8.30-7.94 (m, 8H), 7.62 (d, 2H), 7.49 (d, 2H), 7.12 (d, 2H), 5.52 (br. s, 1H), 5.37 (quint, 1H), 4.47-4.20 (m, 6H), 3.86-3.77 (m, 2H), 3.52-3.38 (m, 4H), 2.60-2.51 (m, 7H), 1.11 (dd, 6H).

LC-MS (method 6): $R_t$=1.24 min; MS (ESIpos): m/z=878 [M+H]$^+$.

B. DETERMINATION OF SOLUBILITY, STABILITY AND LIBERATION BEHAVIOR a) Determination of the Solubility:

The test substance is suspended in 5% strength aqueous dextrose solution. This suspension is shaken at room temperature for 24 h. After ultracentrifugation at 224 000 g for 30 min, the supernatant is diluted with DMSO and analysed by HPLC. A two-point calibration plot of the test compound in DMSO is used for quantification.

HPLC Method for Acids:

Agilent 1100 with DAD (G1315A), quat. Pump (G1311A), autosampler CTC HTS PAL, degasser (G1322A) and column thermostat (G1316A); column: Phenomenex Gemini C18, 5 μm, 50 mm×2 mm; temperature: 40° C.; eluent A: water/phosphoric acid pH 2, eluent B: acetonitrile; flow rate: 0.7 ml/min; gradient: 0-0.5 min 85% A, 15% B; ramp 0.5-3 min 10% A, 90% B; 3-3.5 min 10% A, 90% B; ramp 3.5-4 min 85% A, 15% B; 4-5 min 85% A, 15% B.

HPLC Method for Bases:

Agilent 1100 with DAD (G1315A), quat. pump (G1311A), autosampler CTC HTS PAL, degasser (G1322A) and column thermostat (G1316A); column: VDSoptilab Kromasil 100 C18, 3.5 μm, 60 mm×2.1 mm; temperature: 30° C.; eluent A: water+5 ml of perchloric acid/liter, eluent B: acetonitrile; flow rate: 0.75 ml/min; gradient: 0-0.5 min 98% A, 2% B; ramp 0.5-4.5 min 10% A, 90% B; 4.5-6 min 10% A, 90% B; ramp 6.5-6.7 min 98% A, 2% B; 6.7-7.5 min 98% A, 2% B.

The solubilities of representative exemplary embodiments in 5% strength aqueous dextrose solution are shown in Table 1:

TABLE 1

| Example No. | Solubility [mg/Liter] |
| --- | --- |
| 2 | 670 |
| 3 | 590 |
| 4 | 860 |
| 31 | 220 |
| 33 | 620 |
| 35 | 610 |
| 36 | 700 |
| 38 | 750 |
| 39 | 490 |

No decomposition of the examplary compounds in these solutions was observed.

The solubility of the active substance from example 8A was determined in this test to be <1.2 mg/liter.

b) Stability in Buffer at Various pH Values:

0.3 mg of the test substance is weighed into a 2 ml HPLC vial and 0.5 ml of acetonitrile or acetonitrile/DMSO (9:1) is added. The substance is dissolved by putting the sample vessel in an ultrasonic bath for about 10 seconds. Then 0.5 ml of the respective buffer solution is added, and the sample is again treated in the ultrasonic bath.

(Buffer) Solutions Employed:

pH 2: 0.03 mol of citric acid, 0.061 mol of sodium chloride and 0.0082 mol of hydrochoric acid ad 1 liter of water;

pH 4: 1 liter of Millipore water is adjusted to pH 4.0 with 1 N hydrochloric acid;

pH 5: 0.096 mol of citric acid and 0.2 mol of sodium hydroxide ad 1 liter of water;

pH 6: 0.06 mol of citric acid and 0.16 mol of sodium hydroxide ad 1 liter of water;

pH 7.4: 90.0 g of sodium chloride, 13.61 g of potassium dihydrogen phosphate and 83.35 g of 1 N sodium hydroxide solution are made up to 1 liter with water; this solution is then further diluted 1:10 with Millipore water.

pH 8: 0.013 mol of borax and 0.021 mol of hydrochloric acid ad 1 liter of water.

5 μl portions of the test solution are analyzed by HPLC for their content of unchanged test substance, and of active substance (A) formed, every hour over a period of 24 hours at 37° C. The percentage areas of the appropriate peaks are used for quantification.

HPLC Method for Example 2

Agilent 1100 with DAD (G1315B), binary pump (G1312A), autosampler (G1329A), column oven (G1316A), thermostat (G1330B); column: Kromasil 100 C18, 125 mm×4 mm, 5 μm; column temperature: 30° C.; eluent A: water+5 ml perchloric acid/liter, eluent B: acetonitrile; gradient: 0 min 90% A→6.0 min 61% A→18.0 min 61% A→20.0 min 10% A→21.0 min 10% A→23.0 min 90% A→26.0 min 90% A; flow rate: 2.0 ml/min; UV detection: 294 nm.

HPLC Method for Example 7

Agilent 1100 with DAD (G1314A), binary pump (G1312A), autosampler (G1329A), column oven (G1316A), thermostat (G1330A); column: Kromasil 100 C18, 250 mm×4 mm, 5 μm; column temperature: 30° C.; eluent A: water+5 ml perchloric acid/liter, eluent B: acetonitrile; gradient: 0 min 90% A→5.0 min 55% A→18.0 min 55% A→20.0 min 10% A→21.0 min 10% A→22.5 min 90% A→25.0 min 90% A; flow rate: 2.0 ml/min; UV detection: 288 nm.

HPLC Method for Example 8

Agilent 1100 with DAD (G1315B), binary pump (G1312A), autosampler (G1329A), column oven (G1316A), thermostat (G1330B); column: Kromasil 100 C18, 250 mm×4 mm, 5 μm; column temperature: 30° C.; eluent A: water+5 ml perchloric acid/liter, eluent B: acetonitrile; gradient: 0 min 90% A→3.0 min 55.5% A→14.0 min 55.5% A→20.0 min 10% A→23.0 min 10% A→26.0 min 90% A; flow rate: 2.0 ml/min; UV detection: 294 nm.

HPLC Method for Example 14

Agilent 1100 with DAD (G1315A), binary pump (G1312A), autosampler (G1329A), column oven (G1316A), thermostat (G1330A); column: Kromasil 100 C18, 125 mm×4 mm, 5 μm; column temperature: 30° C.; eluent A: water+5 ml perchloric acid/liter, eluent B: acetonitrile; gradient: 0 min 90% A→4.0 min 56% A→18.0 min 56% A→20.0 min 10% A→21.0 min 10%→23.0 min 90% A→25.0 min 90% A; flow rate: 2.0 ml/min; UV detection: 294 nm.

HPLC Method for Example 26

Agilent 1100 with DAD (G1315A), binary pump (G1312A), autosampler (G1329A), column oven (G1316A), thermostat (G1330A); column: Kromasil 100 C18, 125 mm×4 mm, 5 μm; column temperature: 30° C.; eluent A: water+5 ml perchloric acid/liter, eluent B: acetonitrile; gradient: 0 min 90% A→8.0 min 47% A→18.0 min 47% A→20.0 min 10% A→21.0 min 10%→22.5 min 98% A→25.0 min 98% A; flow rate: 2.0 ml/min; UV detection: 294 nm.

HPLC Method for Example 28 and example 32

Agilent 1100 with DAD (G1314A), binary pump (G1312A), autosampler (G1329A), column oven (G1316A), thermostat (G1330A); column: Kromasil 100 C18, 125 mm×4 mm, 5 μm; column temperature: 30° C.; eluent A: water+5 ml of perchloric acid/liter, eluent B: acetonitrile; gradient: 0 min 90% A→6.0 min 61% A→18.0 min 61% A 20.0 min 10% A→21.0 min 10% A→23.0 min 90% A→26.0 min 90% A; flow rate: 2.0 ml/min; UV detection: 294 nm.

HPLC Method for Example 33

Agilent 1100 with DAD (G1314A), binary pump (G1312A), autosampler (G1329A), column oven (G1316A), thermostat (G1330A); column: Kromasil 100 C18, 125 mm×4 mm, 5 µm; column temperature: 30° C.; eluent A: water+5 ml of perchloric acid/liter, eluent B: acetonitrile; gradient: 0 min 90% A→4.0 min 56% A→18.0 min 56% A→20.0 min 10% A→21.0 min 10% A→23.0 min 90% A→25.0 min 90% A; flow rate: 2.0 ml/min; UV detection: 294 nm.

HPLC Method for Example 34

Agilent 1100 with DAD (G1314A), binary pump (G1312A), autosampler (G1329A), column oven (G1316A), thermostat (G1330A); column: Kromasil 100 C18, 60 mm×2.1 mm, 3.5 µm; column temperature: 30° C.; eluent A: water+5 ml of perchloric acid/liter, eluent B: acetonitrile; gradient: 0 min 98% A→1.0 min 98% A 9.0 min 2% A→13.0 min 2% A→13.5 min 98% A→15.0 min 98% A; flow rate: 0.75 ml/min; UV detection: 210 nm.

HPLC Method for Example 35

Agilent 1100 with DAD (G1314A), binary pump (G1312A), autosampler (G1329A), column oven (G1316A), thermostat (G1330A); column: Kromasil 100 C18, 125 mm×4 mm, 5 µm; column temperature: 30° C.; eluent A: water+5 ml of perchloric acid/liter, eluent B: acetonitrile; gradient: 0 min 90% A→2.0 min 64% A 18.0 min 64% A→20.0 min 10% A→21.0 min 10% A→23.0 min 90% A→26.0 min 90% A; flow rate: 2.0 ml/min; UV detection: 294 nm.

The ratios of the peak areas (F) at the respective time points in relation to the peak areas at the starting time are shown in Table 2 for representative exemplary embodiments:

TABLE 2

| Example No. | pH | % test substance after 4 h [F(t = 4 h) × 100/F(t = 0 h)] | % test substance after 24 h [F(t = 24 h) × 100/F(t = 0 h)] |
|---|---|---|---|
| 2 | 4 | 100 | 100 |
| 2 | 7.4 | 100 | 68 |
| 7 | 4 | 100 | 100 |
| 7 | 5 | 98 | 83 |
| 7 | 7.4 | 0 | 0 |
| 8 | 4 | 100 | 100 |
| 8 | 7.4 | 82 | 34 |
| 14 | 4 | 96 | 95 |
| 14 | 7.4 | 100 | 91 |
| 26 | 4 | 100 | 99 |
| 26 | 5 | 97 | 92 |
| 26 | 7.4 | 84 | 34 |
| 28 | 4 | 100 | 99 |
| 28 | 7.4 | 99 | 88 |
| 32 | 4 | 100 | 100 |
| 32 | 5 | 100 | 100 |
| 32 | 6 | 99 | 98 |
| 32 | 7.4 | 96 | 81 |
| 33 | 4 | 100 | 100 |
| 33 | 5 | 100 | 97 |
| 33 | 6 | 78 | 28 |
| 33 | 7.4 | 29 | 0 |
| 34 | 4 | 100 | 99 |
| 34 | 7.4 | 0 | 0 |
| 35 | 4 | 98 | 94 |
| 35 | 7.4 | 2 | 0 |

In this test there was found to be a decrease in the content of test substance at the same time as an increase in the active ingredient compound from example 8A and 9A in question.

c) In Vitro Stability in Rat and Human Plasma:

1 mg of the test substance is weighed into a 2 ml HPLC vial, and 1.5 ml of DMSO and 1 ml of water are added. The substance is dissolved by placing the sample vessel in an ultrasonic bath for about 10 seconds. 0.5 ml of rat or human plasma at 37° C. is added to 0.5 ml of this solution. The sample is shaken, and about 10 µl are removed for a first analysis (time point $t_0$). 4-6 further aliquots are removed for quantification in the period up to 2 hours after the start of incubation. The sample is kept at 37° C. during the time of the test. Characterization and quantification take place by HPLC. HPLC Method:

Agilent 1100 with DAD (G1314A), binary pump (G1312A), autosampler (G1329A), column oven (G1316A), thermostat (G1330A); column: Kromasil 100 C18, 250 mm×4 mm, 5 µm; column temperature: 30° C.; eluent A: water+5 ml of perchloric acid/liter, eluent B: acetonitrile; gradient: 0-8.0 min 53% A, 47% B; 8.0-18.0 min 53% A, 47% B; 18.0-20.0 min 90% A, 10% B; 20.0-21.0 min 90% A, 10% B; 21.0-22.5 min 98% A, 2% B; 22.5-25.0 min 98% A, 2% B; flow rate: 2 ml/min; UV detection: 294 nm.

Table 3 indicates the respective times for representative exemplary embodiments at which 50% (example 33: 30%) of the maximum possible amount of active ingredient compound (example 8A and 9A) have been produced ($t_{50\%A}$ or $t_{30\%A}$) after incubation with rat plasma. For the evaluation, the ratio of the peak areas at the individual time points compared with the starting time point was used in each case.

TABLE 3

| Example No. | $t_{50\%A}$ [min] in rat plasma |
|---|---|
| 2 | 5 |
| 7 | 5 |
| 8 | 5 |
| 26 | 3 |
| 31 | 3 |
| 32 | 90 |
| 33 | 17* |
| 34 | 10 |
| 35 | 10 |

*$t_{30\%A}$ value [min]

d) i.v. Pharmacokinetics in Wistar Rats:

On the day before administration of the substance, a catheter for obtaining blood is implanted in the jugular vein of the experimental animals (male Wistar rats, body weight 200-250 g) under Isofluran® anesthesia.

On the day of the experiment, a defined dose of the test substance is administered as solution into the tail vein using a Hamilton® glass syringe (bolus administration, duration of administration <10 s). Blood samples (8-12 time points) are taken through the catheter sequentially over the course of 24 h after administration of the substance. Plasma is obtained by centrifuging the samples in heparinized tubes. Acetonitrile is added to a defined plasma volume per time point to precipitate proteins. After centrifugation, test substance and, where appropriate, known cleavage products of the test substance in the supernatant are determined quantitatively using a suitable LC/MS-MS method.

The measured plasma concentrations are used to calculate pharmacokinetic parameters of the test substance and of the active ingredient compound (A) liberated therefrom, such as AUC, $C_{max}$, $T_{1/2}$ (half-life) and CL (clearance).**

After i.v. administration of the compound from example 32 and example 33, these substances were no longer detectable in plasma even at the first measurement point. Only the active ingredient (example 8A) was detectable up to the 24-hour time point too.

e) Oral Pharmacokinetics in Wistar Rats:

On the day before administration of the substance, a catheter for obtaining blood is implanted in the jugular vein of the experimental animals (male Wistar rats, body weight 200-250 g) under Isofluran® anesthesia.

On the day of the experiment, a defined dose of the test substance is administered as solution into the stomach by gavage. Blood samples (8-12 time points) are taken through the catheter sequentially over the course of 24 h after administration of the substance. Plasma is obtained by centrifuging the samples in heparinized tubes. Acetonitrile is added to a defined plasma volume per time point to precipitate proteins. After centrifugation, test substance and, where appropriate, known cleavage products of the test substance in the supernatant are determined quantitatively using a suitable LC/MS-MS method.

The measured plasma concentrations are used to calculate pharmacokinetic parameters of the test substance and of the active ingredient compound (A) liberated therefrom, such as AUC, $C_{max}$, $T_{1/2}$ (half-life).

After oral administration of the compound from example 2, example 7, example 8 and example 33 respectively, these substances were no longer detectable in plasma even at the first measurement point. Only the active ingredient (example 8A) was detectable up to the 24-hour time point too.

f) Hemodynamic Measurements on Anesthetized Rats:

Wistar rats (250-300 g body weight; from Harlan-Winkelmann) are anesthetized with 5% Isofluran®. Anesthesia is maintained with 2% Isofluran® and pressurized air in an anesthesia mask. The carotid artery is exposed, and a tip catheter (Millar micro-tip transducer, 2 French; from HSE) is inserted and advanced into the left ventricle. A second catheter is then inserted into the jugular vein. Through this catheter, placebo solution and test substance solutions in increasing concentration are infused into the animals. At the same time, the cardiac function (such as heart rate, left ventricular pressure, contractility (dp/dt), left ventricular end-diastolic pressure) is measured via the left ventricular catheter. By withdrawing the catheter from the left ventricle into the aorta, it is also possible to measure the systemic blood pressure as well.

g) Blood Pressure and Heart Rate Measurements on Awake Rats:

Awake rats which are spontaneously hypertensive (SH rats) and which carry an internal transmitter capable of continual measurement both of blood pressure and also heart rate (telemetric capture of hemodynamic parameters) are administered test substances orally in various doses. Subsequently, blood pressure and heart rate, and their changes, are recorded over 24 hours.

Table 4 shows the maximum lowering of heart rate after per oral administration of 3 mg/kg of the compound from example 32 or example 33 in comparison to the active substance (example 8A):

TABLE 4

| Example No. | Dose | Heart rate reduction |
| --- | --- | --- |
| 8A | 3 mg/kg | 10% |
| 32 | 3 mg/kg | 10% |
| 33 | 3 mg/kg | 10% |

C. EXEMPLARY EMBODIMENTS OF PHARMACEUTICAL COMPOSITIONS

The compounds of the invention can be converted into pharmaceutical preparations in the following ways:

Tablet:

Composition:

100 mg of the compound of the invention, 50 mg of lactose (monohydrate), 50 mg of corn starch (native), 10 mg of polyvinylpyrrolidone (PVP 25) (BASF, Ludwigshafen, Germany) and 2 mg of magnesium stearate.

Tablet weight 212 mg. Diameter 8 mm, radius of curvature 12 mm.

Production:

The mixture of the compound of the invention, lactose and starch is granulated with a 5% strength solution (m/m) of PVP in water. The granules are dried and then mixed with the magnesium stearate for 5 min. This mixture is compressed with a conventional tablet press (see above for format of the tablet). As guideline, a compressive force of 15 kN is used for the compression.

Oral Suspension:

Composition:

1000 mg of the compound of the invention, 1000 mg of ethanol (96%), 400 mg of Rhodigel® (xanthan gum from FMC, Pennsylvania, USA) and 99 g of water.

10 ml of oral suspension are equivalent to a single dose of 100 mg of the compound of the invention.

Production:

The Rhodigel is suspended in ethanol, and the compound of the invention is added to the suspension. The water is added while stirring. The mixture is stirred for about 6 hours until the swelling of the Rhodigel is complete.

Oral Solution:

Composition:

500 mg of the compound of the invention, 2.5 g of polysorbate and 97 g of polyethylene glycol 400. A single dose of 100 mg of the compound of the invention corresponds to 20 g oral solution.

Production:

The compound of the invention is suspended in a mixture of polyethylene glycol and polysorbate with stirring. The stirring is continued until the compound of the invention has completely dissolved.

i.v. Solution:

The compound of the invention is dissolved in a concentration below the saturation solubility in a physiologically tolerated solvent (e.g. isotronic saline solution, 5% glucose solution and/or 30% PEG 400 solution, in each case adjusted to a pH of 3-5). The solution is optionally filtered sterile and/or dispensed into sterile and pyrogen-free injection containers.

The invention claimed is:
1. A compound of the formula (I)

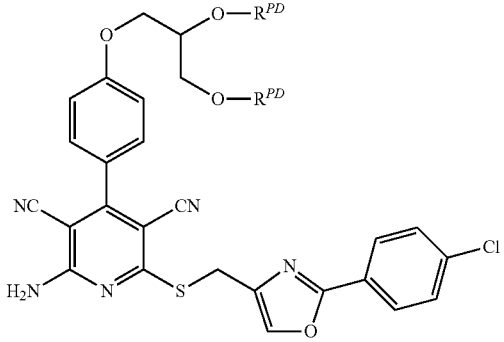

in which
R$^{PD}$ is a group of the formula

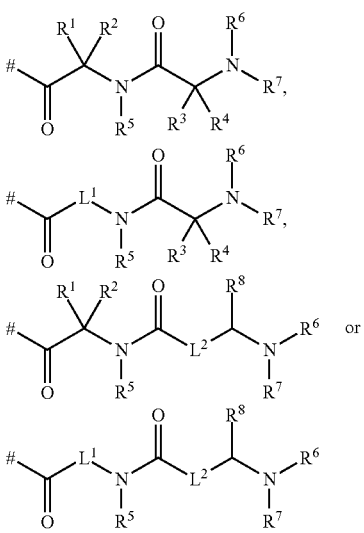

in which
# means the point of linkage to the respective O atom,
L$^1$ is straight-chain (C2-C4)-alkanediyl,
L$^2$ is straight-chain (C1-C3)-alkanediyl,
R$^1$ and R$^3$ are identical or different and are independently of one another hydrogen or the side group of a natural α-amino acid or its homologs or isomers,
R$^2$ and R$^4$ are independently of one another hydrogen or methyl
or
R$^1$ and R$^2$ or R$^3$ and R$^4$ are in each case linked to one another and, together with the carbon atom to which they are jointly attached, form a 3- to 6-membered saturated carbocycle,
R$^5$ is hydrogen or (C1-C4)-alkyl
or
R$^5$ is linked to R$^1$ and both, together with the atoms to which they are attached, form a pyrrolidine or piperidine ring,
R$^6$ and R$^7$ are identical or different and independently of one another are hydrogen or (C$_1$-C$_4$)-alkyl which may be substituted by hydroxyl, (C$_1$-C$_4$)-alkoxy, amino, mono-(C$_1$-C$_4$)-alkylamino or di-(C$_1$-C$_4$)-alkylamino
or
R$^6$ and R$^7$ are linked to one another and, together with the nitrogen atom to which they are attached, form a 5- or 6-membered saturated heterocycle which may comprise a further ring heteroatom from the series consisting of N and O, and may be substituted one or two times, identically or differently, by (C$_1$-C$_4$)-alkyl, amino, hydroxyl and/or (C$_1$-C$_4$)-alkoxy,
or
R$^6$ is linked to R$^3$ and both, together with the atoms to which they are attached, form a pyrrolidine or piperidine ring
and
R$^8$ is hydrogen or carboxyl,
and the salts thereof.

2. The compound of the formula (I) as claimed in claim 1, in which
R$^{PD}$ is a group of the formula

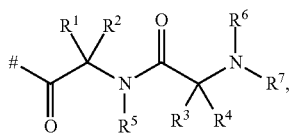

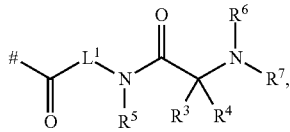

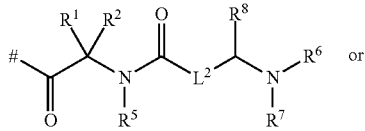

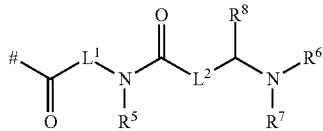

in which
# means the point of linkage to the respective O atom,
L$^1$ is ethane-1,2-diyl,
L$^2$ is methanediyl or ethane-1,2-diyl,
R$^1$ is hydrogen, methyl, propan-2-yl, 1-methylpropan-1-yl, 2-methylpropan-1-yl, benzyl, p-hydroxybenzyl, hydroxymethyl or 1-hydroxyethyl,
R$^2$ is hydrogen,
R$^3$ is hydrogen, methyl, propan-2-yl, 1-methylpropan-1-yl, 2-methylpropan-1-yl, benzyl, imidazol-4-ylmethyl, hydroxymethyl, 1-hydroxyethyl, carbamoylmethyl, 2-carbamoylethyl, carboxymethyl, 2-carboxyethyl, 4-aminobutan-1-yl, 3-aminopropan-1-yl, 2-aminoethyl, aminomethyl or 3-guanidinopropan-1-yl,
R$^4$ is hydrogen,
R$^5$ is hydrogen or methyl
or
R$^5$ is linked to R$^1$ and both, together with the atoms to which they are attached, form a pyrrolidine ring, $R^6$ is hydrogen or methyl or $R^6$ is linked to $R^3$ and both, together with the atoms to which they are attached, form a pyrrolidine ring, $R^7$ is hydrogen or methyl and $R^8$ is hydrogen or carboxyl, and the salts thereof.

3. The compound of the formula (I) as claimed in claim 1, in which $R^{PD}$ is a group of the formula

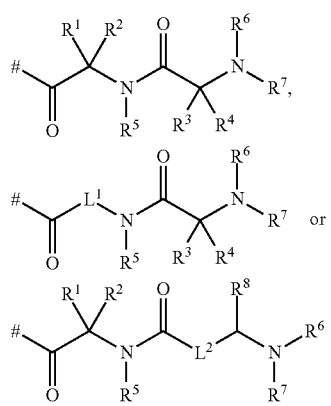

in which

\# means the point of linkage to the respective O atom, $L^1$ is ethane-1,2-diyl, $L^2$ is methanediyl, $R^1$ is hydrogen, methyl, propan-2-yl, 1-methylpropan-1-yl, 2-methylpropan-1-yl, hydroxymethyl or 1-hydroxyethyl, $R^2$ is hydrogen, $R^3$ is hydrogen, methyl, propan-2-yl, 1-methylpropan-1-yl, 2-methylpropan-1-yl, imidazol-4-ylmethyl, hydroxymethyl, 1-hydroxyethyl, 2-carboxyethyl, 4-aminobutan-1-yl, 3-aminopropan-1-yl or 2-aminoethyl, $R^4$ is hydrogen, $R^5$ is hydrogen $R^6$ is hydrogen or methyl or $R^6$ is linked to $R^3$ and both, together with the atoms to which they are attached, form a pyrrolidine ring, $R^7$ is hydrogen and $R^8$ is hydrogen, and the salts thereof.

4. The compound of the formula (I) as claimed in claim 1, in which the two groups $R^{PD}$ are identical, and the salts thereof.

5. The compound as claimed in claim 1, with the formula (I-A)

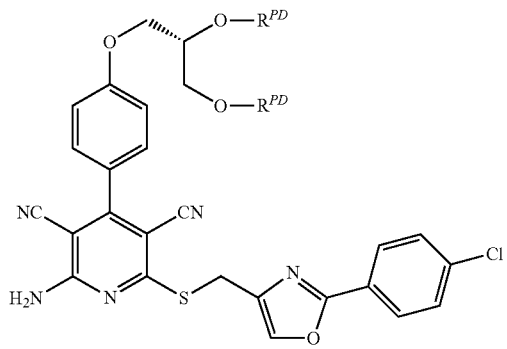

and the salts thereof.

6. A process for preparing compounds of the formula (I) as defined in claim 1, in which the two groups $R^{PD}$ are each identical, characterized in that the compound (A)

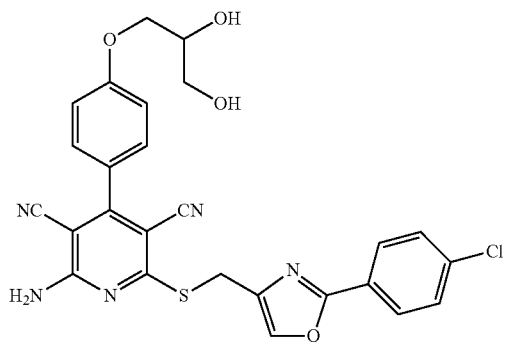

either

[A] is esterified in an inert solvent in the presence of a condensing agent initially with two or more equivalents of an amino acid of the formula (II) or (III)

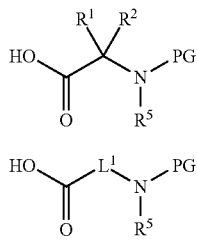

in which $L^1$, $R^1$, $R^2$ and $R^5$ have the meanings indicated in claim 1, and PG is a temporary amino protective group such as, for example, tert-butoxycarbonyl to give a compound of the formula (IV) or (V), (IV)

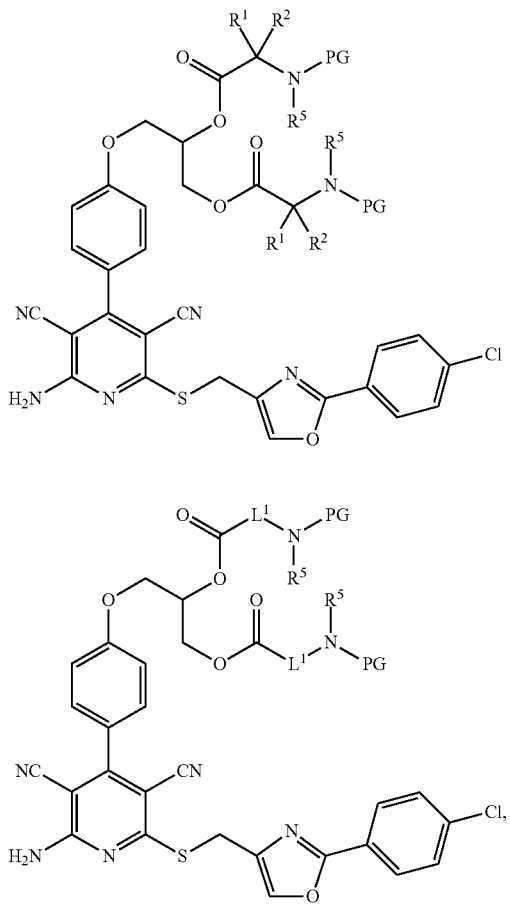

(V)

in which $L^1$, PG, $R^1$, $R^2$ and $R^5$ have the meanings indicated above, then, after elimination of the protective groups PG, said compound (A) is coupled in an inert solvent in the presence of a condensing agent with two or more equivalents of an amino acid of the formula (VI) or (VII)

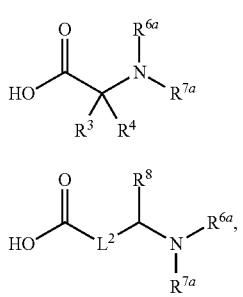

(VI)

(VII)

in which $L^2$, $R^3$, $R^4$ and $R^8$ have the meanings indicated in claim 1, and $R^{6a}$ and $R^{7a}$ are identical or different and have the meanings of respectively $R^6$ and $R^7$ indicated in claim 1, or are a temporary amino protective group, to give a compound of the formula (VIII), (IX), (X) or (XI)

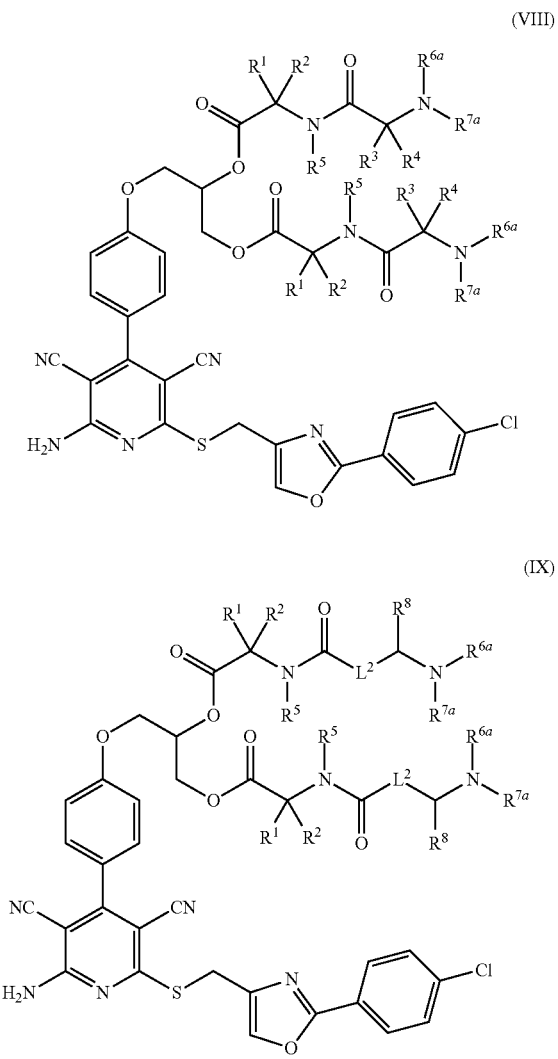

(VIII)

(IX)

(X)

-continued (XI)

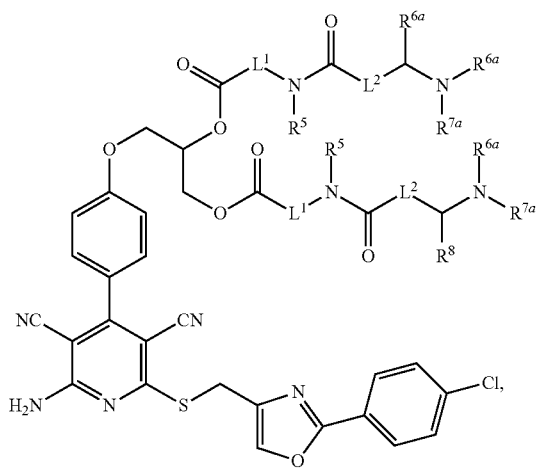

in which $L^1$, $L^2$, $R^1$, $R^2$, $R^3$, $R^4$, $R^5$, $R^{6a}$, $R^{7a}$ and $R^8$ each have the meanings indicated above, and subsequently protective groups which are present where appropriate are removed again, or

[B] is coupled in an inert solvent in the presence of a condensing agent with two or more equivalents of a carboxylic acid of the formula (XII), (XIII), (XIV) or (XV)

(XII)

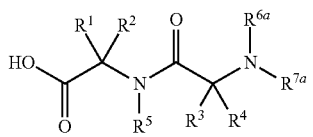

(XIII)

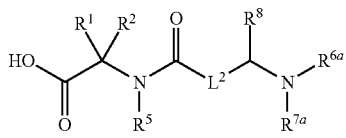

(XIV)

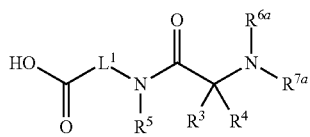

(XV)

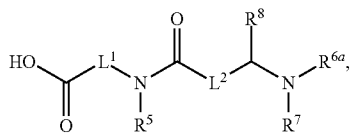

in which $L^1$, $L^2$, $R^1$, $R^2$, $R^3$, $R^4$, $R^5$ and $R^8$ have the meanings indicated in claim 1, and $R^{6a}$ and $R^{7a}$ are identical or different and have the meanings of respectively $R^6$ and $R^7$ indicated in claim 1, or are a temporary amino protective group, to give one of the compounds (VIII), (IX), (X) or (XI) indicated in variant [A] and subsequently protective groups which are present where appropriate are removed again, and the compounds of the formula (I) resulting in each case are optionally converted with the appropriate (i) solvents and/or (ii) acids or bases into the salts thereof.

7. A medicament comprising a compound as defined in claim 1 and an inert, non-toxic, pharmaceutically suitable excipient.

8. A method of treating or reducing the risk of angina pectoris, atrial fibrillation, hypertension, acute coronary syndrome, coronary heart disease, heart failure, ischemic damage to the heart, post myocardial infarction angina pectoris, secondary myocardial infarction, or worsening heart failure, comprising the step of administering a compound as define in claim 1 to a patient.

\* \* \* \* \*